United States Patent
Singh et al.

(10) Patent No.: US 7,714,017 B2
(45) Date of Patent: May 11, 2010

(54) CARBOXYLIC ACID PERI-SUBSTITUTED BICYCLICS FOR OCCLUSIVE ARTERY DISEASE

(75) Inventors: Jasbir Singh, Naperville, IL (US); Mark Gurney, Grand Rapids, MI (US); Georgeta Hategan, Naperville, IL (US); Peng Yu, Lisle, IL (US); David Zembower, LaGrange, IL (US); Nian Zhou, Naperville, IL (US); Alexandre Mikhaylovich Polozov, Naperville, IL (US); Wayne Edward Zeller, Viroqua, WI (US)

(73) Assignee: Decode Genetics, EHF, Reykjavic (IS)

( * ) Notice: Subject to any disclaimer, the term of this patent is extended or adjusted under 35 U.S.C. 154(b) by 28 days.

(21) Appl. No.: 11/247,431

(22) Filed: Oct. 11, 2005

(65) Prior Publication Data
US 2006/0142355 A1  Jun. 29, 2006

Related U.S. Application Data

(60) Provisional application No. 60/618,203, filed on Oct. 12, 2004.

(51) Int. Cl.
*A61K 31/403* (2006.01)
*A61K 31/404* (2006.01)
*A61K 31/405* (2006.01)
*C07D 209/02* (2006.01)
*C07D 209/04* (2006.01)
*A61K 31/19* (2006.01)
*A61K 31/192* (2006.01)
*C07C 61/12* (2006.01)

(52) U.S. Cl. .................. 514/412; 514/415; 514/419; 514/569; 548/452; 548/469; 548/494; 562/400; 562/405

(58) Field of Classification Search .................. 514/366, 514/393, 406; 548/154, 302.1, 360.5
See application file for complete search history.

(56) References Cited

U.S. PATENT DOCUMENTS

| | | | |
|---|---|---|---|
| 4,677,112 A | 6/1987 | Butler et al. | 514/312 |
| 5,239,083 A | 8/1993 | Kumazawa et al. | 548/465 |
| 5,281,593 A * | 1/1994 | Gilmore et al. | 514/249 |
| 5,451,688 A | 9/1995 | Kogen et al. | |
| 5,468,898 A | 11/1995 | Huang et al. | 560/41 |
| 5,744,488 A | 4/1998 | Cross et al. | 514/339 |
| 6,166,219 A | 12/2000 | Yamasaki et al. | 548/309 |
| 6,235,777 B1 | 5/2001 | Ohuchida et al. | 514/510 |
| 6,242,493 B1 | 6/2001 | Gareau et al. | 514/569 |
| 6,303,593 B1 | 10/2001 | Bao et al. | 514/210 |
| 6,380,249 B1 * | 4/2002 | Young et al. | 514/530 |
| 2006/0079520 A1 * | 4/2006 | Singh et al. | 514/230.5 |

FOREIGN PATENT DOCUMENTS

| | | | |
|---|---|---|---|
| BE | 649166 A * | 12/1964 | |
| DE | 911 063 | 5/1954 | |
| EP | 1375486 A1 | 1/2004 | |
| EP | 1 431 267 A1 | 6/2004 | |
| JP | 04059743 | 2/1992 | |

OTHER PUBLICATIONS

Singh, et al. U.S. Appl. No. 11/169,161.*
Patent BE 649,166, abstract and structure from STN search.*
Patent BE 649,166, (1964), Abstract and structures from STN search report.*
Singh, et al. U.S. Appl. No. 11/169,161, (2005).*
Juteau et al., "Structure-Activity Relationship of Cinnamic Acylsulfonamide Analogues on the Human $EP_3$ Prostanoid Receptor," Bioorganic & Medicinal Chemistry 9, 1977-1984 (2001).
Gallant et al., "Structure-Activity Relationship of Biaryl Acylsulfonamide Analogues on the Human $EP_3$ Prostanoid Receptor," Bioorganic & Medicinal Chemistry Letters 12, 2583-2586 (2002).
Thierin et al., "Synthesis and Biological Evaluation of 5,6-Diarylimidazo[2.1-b] Thiazole As Selective Cox-2 Inhibitors", Bioorganic & Medicinal Chemistry Letters, vol. 7 (1), pp. 47-52 (1997).
Weidenau, et al., "Total Synthesis of (+)(−)-*cis*-Trikentrin A", Tetrahedron, vol. 51(4), pp. 1167-1176 (1995).
Database Beilstein Reg. No. 8708720 & 8709004, Kochergin et al., Chemical Abstract XP-002365685, Chem. Heterocycl. Compd., vol. 36(4), pp. 455-458, 2000.
Confalone et al., "Stereospecific Total Synthesis of *d*-Biotin from L(+)-Cysteine[1]", Journal of the American Chemical Society, vol. 99(21), pp. 7020-7026 (1997).
Chemical Abstract for 77313337-2 registry, *Rare Chemicals Catalogue* (Sep. 27, 2004).
International Search Report and Written Opinion for PCT/US2005/036574, (2006).

* cited by examiner

*Primary Examiner*—Yong Chu
(74) *Attorney, Agent, or Firm*—Heslin Rothenberg Farley & Mesiti P.C.

(57) ABSTRACT

Peri-substituted, fused bicyclic ring carboxylic acids useful for the treatment or prophylaxis of a prostaglandin-mediated disease or condition are disclosed. The compounds are of the general formula

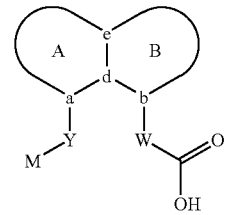

A representative example is:

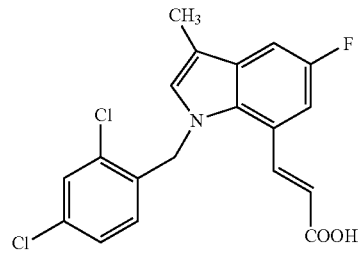

13 Claims, No Drawings

CARBOXYLIC ACID PERI-SUBSTITUTED BICYCLICS FOR OCCLUSIVE ARTERY DISEASE

CROSS REFERENCE TO RELATED APPLICATIONS

This application claims benefit of U.S. provisional application 60/618,203, filed Oct. 12, 2004, the entire contents of which are incorporated herein by reference.

FIELD OF THE INVENTION

The invention relates to a chemical genus of peri-substituted, bicyclic acids useful for the treatment and prophylaxis of occlusive artery disease and related prostaglandin-mediated disorders.

BACKGROUND OF THE INVENTION

Atherosclerosis is the pathology underlying several of mankind's most lethal diseases, such as myocardial infarction and peripheral arterial occlusive disease (PAOD). PAOD represents atherosclerosis of the large and medium arteries of the limbs, particularly to the lower extremities, and includes the aorta and iliac arteries. It often coexists with coronary artery disease and cerebrovascular disease. Persons with PAOD are at increased risk of other vascular events such as myocardial infarction or stroke [Waters, R E, Terjung R L, Peters K G & Annex B H. J. Appl. Physiol. 2004; Ouriel K. Lancet, 2001, 258:1257-64; Kroger, K. Angiology, 2004, 55:135-138]. Clinically significant lesions may gradually narrow the peripheral arteries leading to pain on walking usually relieved by rest (claudication), ischemic ulcers, gangrene, and sometimes limb amputation. Medical therapy is generally ineffective but operations bypassing or replacing the lesion with artificial or venous grafts improve blood flow distally, at least until they become restenosed [Haustein, K. O., *Int. J. Clin. Pharmacol. Ther.,* 35:266 (1997)]. Recently, it has been discovered through human genetic linkage studies that DNA variants of the PTGER3 gene that encodes the prostaglandin $E_2$ receptor subtype 3 (known as EP3) increase the risk of an individual developing PAOD (see US published application 2003/0157599). Thus, antagonists of prostaglandin $E_2$ ($PGE_2$) binding to the EP3 receptor may provide effective treatment or prophylaxis for PAOD.

In response to various extracellular stimuli, prostaglandins are rapidly generated from free arachidonic acid through the consecutive action of the cyclo-oxygenases and synthases. The prostaglandins exert their action in close proximity to the site of their synthesis. To date, eight prostanoid receptors have been cloned and characterized. These receptors are members of the growing class of G-protein-coupled receptors. $PGE_2$ binds preferentially to the EP1, EP2, EP3, and EP4 receptors; $PGD_2$ to the DP and FP receptors; $PGF_{2\alpha}$ to the FP and EP3 receptors; $PGI_2$ to the IP receptor and $TXA_2$ to the TP receptor. $PGE_2$ binding to the EP3 receptor has been found to play a key role in the regulation of ion transport, smooth muscle contraction of the GI tract, acid secretion, uterine contraction during fertilization and implantation, fever generation and hyperalgesia. The EP3 receptor has been detected in many organs such as the kidney, the gastrointestinal tract, the uterus and the brain. In the cardiovascular system, EP3 is expressed by vascular endothelium and smooth muscle, and at least four isoforms of EP3 are expressed on human platelets [Paul, B. Z., B. Ashby, and S. B. Sheth, Distribution of prostaglandin IP and EP receptor subtypes and isoforms in platelets and human umbilical artery smooth muscle cells. British Journal of Haematology, 1998. 102(5): p. 1204-11.]

Prostanoids, acting through specific membrane receptors belonging to the superfamily of G protein-coupled receptors (GPCRs) have an essential role in vascular homeostasis, including platelet function regulation. Among the prostanoids, thomboxane A2 ($TxA_2$) is a potent stimulator of platelet aggregation, whereas prostaglandin (PG) $I_2$ inhibits their activation. On the other hand, prostaglandin $E_2$ ($PGE_2$) has been reported to have a biphasic effect on platelet response, potentiating their aggregation at low concentrations and inhibiting it at higher concentrations. It has been shown that the stimulatory effects of $PGE_2$ on platelet aggregation are exerted mainly through EP3 receptor, one of the four subtypes of receptors activated by $PGE_2$.

Local synthesis of prostaglandins in the arterial vessel wall may play a profound role in atherosclerosis. While only COX-1 is present in the healthy vessel wall, both COX-1 and COX-2 are present in arteriosclerotic plaque [Schonbeck, U., et al., Augmented expression of cyclooxygenase-2 in human atherosclerotic lesions. Am J Pathol, 1999. 155(4): p. 1281-91; Cipollone, F., et al., Overexpression of functionally coupled cyclooxygenase-2 and prostaglandin E synthase in symptomatic atherosclerotic plaques as a basis of $PGE_2$-dependent plaque instability. Circulation, 2001. 104(8): p. 921-7]. Their increased expression, together with increased expression of prostaglandin E synthase, may account for the increased production of $PGE_2$ noted above. In genetically modified mice lacking the low density lipoprotein receptor (LDL-R), formation of atherosclerotic plaque can be reduced by treatment with rofecoxib, a selective inhibitor of COX-2, through reducing production of $PGE_2$ and other prostaglandins [Burleigh M E, Babaev V R, Oates J A, Harris R C, Gautam S, Riendeau D, Marnett L J, Morrow J D, Fazio S, Linton M F. Cyclooxygenase-2 promotes early atherosclerotic lesion formation in LDL receptor-deficient mice. Circulation. Apr. 16, 2002;105(15):1816-23].

Within the atherosclerotic plaque, vascular smooth muscle cells have been shown to express EP3 receptors and $PGE_2$ stimulates their proliferation and migration, a hallmark of atherosclerotic plaque formation [Blindt R, Bosserhoff A K, vom Dahl J, Hanrath P, Schror K, Hohlfeld T, Meyer-Kirchrath J. Activation of IP and EP(3) receptors alters cAMP-dependent cell migration. Eur J Pharmacol. May 24, 2002; 444(1-2):31-7]. It is, therefore, plausible that chronically inflamed vessels produce sufficient quantities of $PGE_2$ to activate $EP_3$ receptors on vascular smooth muscles cells (contributing to atherosclerotic lesion formation) and on platelets (contributing to thrombosis). Locally produced $PGE_2$ (from platelets themselves, vessel wall components, and inflammatory cells) potentiates platelet aggregation by suboptimal amounts of prothrombotic tissue factors, which might not cause aggregation by themselves, through priming of protein kinase C. The intracellular events triggered by activation of the $EP_3$ receptor may enhance platelet aggregation by opposing the effect of $PGI_2$ and enhancing the effects of primary aggregating agents such as collagen. $EP_3$ receptor activation may therefore contribute to atherosclerosis and the risk of thrombosis observed in pathological states such as vasculitis and PAOD.

Current treatments for PAOD either address increased risk for cardiovascular events such as myocardial infarction and stroke, or provide symptomatic relief for claudication. All of these treatments affect platelet function. Treatments reducing risk for cardiovascular events include low dose asprin (sufficient to reduce platelet aggregation while still permitting the production of $PGI_2$ by the vessel wall) and inhibitors of the platelet adenosine diphosphate receptor inhibitor (clopidogrel). Binding of adenosine diphosphate to the platelet adenosine diphosphate receptor causes a drop in platelet cAMP with consequent platelet activation and aggregation. Treatments providing symptomatic relief from claudication include platelet phosphodiesterase type 3 inhibitors such as cilostazol which act to increase intracellular levels of cAMP. Inhibitors of the platelet adenosine diphosphate receptor or the platelet phosphodiesterase type 3 act directly or indirectly to increase the content of cAMP in platelets, thereby inhibiting platelet activation and consequent aggregation with thrombus formation. $PGE_2$ binding to EP3 acts to decrease cAMP, therefore an antagonist of $PGE_2$ binding to the EP3 receptor, by opposing the $PGE_2$-dependent decrease in cAMP needed to induce platelet activation and consequent aggregation, or by opposing the $PGE_2$-dependent decrease in vascular smooth muscle cell cAMP needed to stimulate migration, might be expected to provide therapeutic benefit in PAOD. Such an antagonist may also be disease-modifying by inhibiting or reducing atherosclerotic plaque formation.

Prostaglandins furthermore have been implicated in a range of disease states including pain, fever or inflammation associated with rheumatic fever, influenza or other viral infections, common cold, low back and neck pain, skeletal pain, post-partum pain, dysmenorrhea, headache, migraine, toothache, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, pain following surgical and dental procedures, immune and autoimmune diseases; cellular neoplastic transformations or metastic tumor growth; diabetic retinopathy, tumor angiogenesis; prostanoid-induced smooth muscle contraction associated with dysmenorrhea, premature labor, asthma or eosinophil related disorders; Alzheimer's disease; glaucoma; bone loss; osteoporosis; Paget's disease; peptic ulcers, gastritis, regional enteritis, ulcerative colitis, diverticulitis or other gastrointestinal lesions; GI bleeding; coagulation disorders selected from hypoprothrombinemia, hemophilia and other bleeding problems; and kidney disease.

While circulating levels of prostanoids are extremely low in healthy individuals [FitzGerald G A, Brash A R, Falardeau P & Oates J A. JCI 1981 68:12472-1275], the local concentration of $PGE_2$ can dramatically increase in inflammatory states. For example, the local production of $PGE_2$ was shown in vitro to increase more than 30-fold in aortoiliac occlusive disease [Reilly J, Miralles M, Wester W & Sicard G. Surgery, 1999, 126:624-628]. It is, therefore, plausible that chronically inflamed vessels produce sufficient quantities of $PGE_2$ to activate $EP_3$ receptors on platelets. In this environment, the intracellular events triggered by activation of the $EP_3$ receptor may enhance platelet aggregation by opposing the effect of $PGI_2$ and enhancing the effects of primary aggregating agents such as ADP. $EP_3$ receptor activation may therefore contribute to the thrombosis observed in pathological states such as vasculitis and atherosclerosis. Peripheral Arterial Occlusive Disease (PAOD) is an atherosclerotic illness that affects primarily the elderly as a consequence of occlusion of the lumen of peripheral arteries, mainly the femoral artery and it is associated with an increased risk of vascular events as myocardial infraction or stroke [Waters, R E, Terjung R L, Peters K G & Annex B H. J. Appl. Physiol. 2004; Ouriel K. Lancet, 2001, 258:1257-64; Kroger, K. Angiology, 2004, 55:135-138]. Several clinical studies have shown that treatment with prostaglandins improves PAOD symptoms [Reiter M, Bucek R, Stumpflen A & Minar E. Cochrane Database Syst. Rev. 2004, 1:CD000986; Bandiera G, Forletta M, Di Paola F M, Cirielli C. Int. Angiol. 2003, 22:58-63; Matsui K, Ikeda U, Murakami Y, Yoshioka T, Shimada K. Am. Heart J. 2003, 145:330-333] supporting the linkage between PAOD and prostanoid receptor function.

Ortho-substituted phenyl acylsulfonamides and their utility for treating prostaglandin-mediated disorders are described in U.S. Pat. No. 6,242,493 and in two articles by Juteau et al. [BioOrg. Med. Chem. 9, 1977-1984 (2001)] and Gallant et al. [BioOrg. Med. Chem. Let. 12, 2583-2586 (2002)], the disclosures of which are incorporated herein by reference.

SUMMARY OF THE INVENTION

In one aspect the invention relates to compounds of formula I

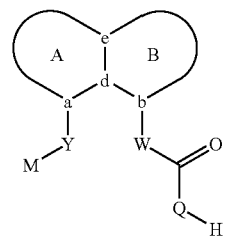

wherein A and B represent a pair of fused 5-, 6- or 7-membered rings. The fused A/B ring system may contain from zero to four heteroatoms chosen from nitrogen, oxygen and sulfur and may be additionally substituted with from zero to four substituents chosen independently from halogen, —OH, loweralkyl, —O-loweralkyl, fluoroloweralkyl, —O-lowerfluoroalkyl, methylenedioxy, ethylenedioxy, alkoxy-loweralkyl, hydroxyloweralkyl, oxo, oxide, —CN, nitro, —S-loweralkyl, amino, loweralkylamino, diloweralkylamino, diloweralkylaminoalkyl, carboxy, carboalkoxy, acyl, carboxamido, loweralkylsulfoxide, acylamino, phenyl, benzyl, spirothiazolidinyl, phenoxy and benzyloxy. The nodes represented by a and b are the points of attachment of residues Y and W respectively, and a and b are in a peri relationship to one another on the fused A/B ring system. The nodes represented by d and e are points of fusion between ring A and ring B in the fused A/B ring system. Each of the nodes a, b, d and e may be either carbon or nitrogen.

W and Y are linkers comprising from zero to 8 atoms in a chain.

M is chosen from aryl, substituted aryl, heterocyclyl, substituted heterocyclyl, $C_6$ to $C_{20}$ alkyl and substituted $C_6$ to $C_{20}$ alkyl.

In one subgenus (Ia), Q is chosen from —N(SO$_2$R$^1$)—, —N(COR$^1$)— and —N[PO(O-alkyl)$_2$]-, and, when W is —CF$_2$—, Q may additionally be —NH—. R$^1$ is chosen from aryl, substituted aryl, heteroaryl, substituted heteroaryl and CF$_3$. In another subgenus (Ib), Q is —O—, and the compounds are carboxylic acids. The claims below relate to subgenus (Ib). The claims in a copending application having the title "Sulfonamide Peri-substituted Bicyclics for Occlusive Artery Disease" and filed on even date herewith, relate to subgenus Ia.

In a further aspect, the invention relates to compounds of formula

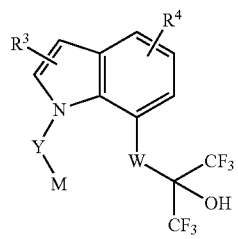

wherein $R^3$ and $R^4$ are chosen independently from hydrogen, halogen, —OH, loweralkyl, —O-loweralkyl, fluorolower-alkyl, —O-lowerfluoroalkyl, methylenedioxy, ethylenedioxy, alkoxy-loweralkyl, hydroxyloweralkyl, oxo, oxide, —CN, nitro, —S-loweralkyl, amino, loweralkylamino, diloweralkylamino, diloweralkylaminoalkyl, carboxy, carboalkoxy, acyl, carboxamido, loweralkylsulfoxide, acylamino, phenyl, benzyl, spirothiazolidinyl, phenoxy and benzyloxy. $R^3$ and $R^4$ may be in either or both rings, that is, both $R^3$ and $R^4$ may be substituents on the six-membered ring, or $R^3$ and $R^4$ may be substituents on the five-membered ring, or each may be in a separate ring. W is a linker comprising from 0 to 8 atoms in a chain. Y is a linker comprising from 1 to 8 atoms in a chain. M is chosen from aryl, substituted aryl, heterocyclyl, substituted heterocyclyl, $C_6$ to $C_{20}$ alkyl and substituted $C_6$ to $C_{20}$ alkyl.

In a further aspect the invention relates to pharmaceutical formulations comprising a pharmaceutically acceptable carrier and a compound as above, or an ester, a pharmaceutically acceptable salt or a hydrate of the compound.

In a further aspect, the invention relates to methods for the treatment or prophylaxis of a prostaglandin-mediated disease or condition. The methods comprise administering to a mammal a therapeutically effective amount of a compound described herein. The disease or condition may be, for example, fever or inflammation associated with rheumatic fever, influenza or other viral infections, migraine, common cold, dysmenorrhea, sprains and strains, myositis, neuralgia, synovitis, arthritis, including rheumatoid arthritis, degenerative joint diseases (osteoarthritis), gout and ankylosing spondylitis, bursitis, burns including radiation and corrosive chemical injuries, sunburns, immune and autoimmune diseases and pain (e.g. low back and neck pain, skeletal pain, post-partum pain, headache, toothache, pain following surgical and dental procedures). EP3 antagonist compounds of the invention that penetrate the CNS are especially suited for pain management.

Compounds of the invention, which inhibit platelet aggregation and increase regional blood flow, are useful for treating primary thromboembolism, thrombosis and occlusive vascular diseases. The compounds can be used advantageously in combination with other platelet aggregation inhibitors and with inhibitors of cholesterol biosynthesis or uptake. The compounds can also be used advantageously in combination with a cyclooxygenase-2 inhibitor to treat inflammatory conditions.

Other diseases or conditions may also be treated, for example, cellular neoplastic transformations or metastic tumor growth; diabetic retinopathy, tumor angiogenesis; prostanoid-induced smooth muscle contraction associated with dysmenorrhea, premature labor, asthma or eosinophil related disorders; Alzheimer's disease; glaucoma; bone loss, osteoporosis or Paget's disease; peptic ulcers, gastritis, regional enteritis, ulcerative colitis, diverticulitis or other gastrointestinal lesions; GI bleeding; coagulation disorders selected from hypoprothrombinemia, hemophilia and other bleeding problems and kidney disease. The method aspect of the invention also includes methods for the promotion of bone formation, for cytoprotection and for reducing plaque in the treatment of atherosclerosis.

In a further aspect, the invention relates to methods for screening for selective prostanoid receptors, particularly EP3 ligands. The screening method may be in vitro screening.

DETAILED DESCRIPTION OF THE INVENTION

Compounds of the genus represented by formula Ib are antagonists at the EP3 receptor. As such they have utility in treating and preventing prostaglandin-mediated conditions, as described above, particularly for such conditions as occlusive vascular disease.

Compositions of the invention comprise an effective dose or a pharmaceutically effective amount or a therapeutically effective amount of a compound described above and may additionally comprise other therapeutic agents, such as platelet aggregation inhibitors (tirofiban, dipyridamole, clopidogrel, ticlopidine and the like) HMG-CoA reductase inhibitors (lovastatin, simvastatin, pravastatin, rosuvastatin, mevastatin, atorvastatin, cerivastatin, pitavastatin, fluvastatin and the like); and cyclooxygenase inhibitors. A further listing of non-limiting examples of antihyperlipidemic agents that may be used in combination with the compounds of the present invention may be found in columns 5-6 of U.S. Pat. No. 6,498,156, the disclosure of which is incorporated herein by reference. Preferred cyclooxygenase-2 inhibitors are those that are selective for cyclooxygenase-2 over cyclooxygenase-1. Preferred cyclooxygenase-2 inhibitors include rofecoxib, meloxicam, celecoxib, etoricoxib, lumiracoxib, valdecoxib, parecoxib, cimicoxib, diclofenac, sulindac, etodolac, ketoralac, ketoprofen, piroxicam and LAS-34475, although the invention is not restricted to these or other known cyclooxygenase-2 inhibitors.

Methods of the invention parallel the compositions and formulations. The methods comprise administering to a patient in need of treatment a therapeutically effective amount of a peri-substituted, fused A/B ring compound according to the invention. The present invention is also directed to methods for screening for selective prostanoid receptor agonists and antagonists. Prostanoid receptors include EP1, EP2, EP3, EP4, IP and FP receptors. Selective EP3 ligands are of great interest, for which the method comprises bringing a labeled compound according to the invention into contact with a cloned human EP3 receptor and measuring its displacement by a test compound.

A genus according to the invention includes compounds of formula Ib:

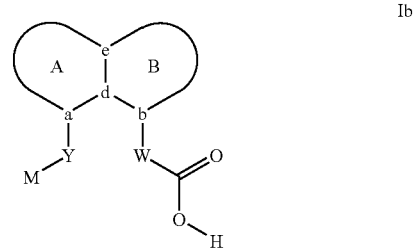

Ib

Each of A and B represents independently a 5-, 6- or 7-membered ring. The fused A/B ring system contains from zero to four heteroatoms chosen from nitrogen, oxygen and sulfur, and the rings are additionally substituted with from zero to four substituents. Suitable substituents include halogen, —OH, loweralkyl, —O-loweralkyl, fluoroloweralkyl, O lowerfluoroalkyl, methylenedioxy, ethylenedioxy, alkoxyloweralkyl, hydroxyloweralkyl, oxo, oxide, —CN, nitro, —S-loweralkyl, amino, loweralkylamino, diloweralkylamino, diloweralkylaminoalkyl, carboxy, carboalkoxy, orthoesters, acyl, carboxamido, loweralkylsulfoxide, acylamino, phenyl, benzyl, spirothiazolidinyl, phenoxy and benzyloxy. Since the fused A/B ring system may include nitrogen or sulfur, the substituents may include oxides, e.g. N→O and S→O. 3-unsubstituted-2-oxo-2,3-dihydro-1H-indole, 3,4-dihydro-2-oxoquinoline and hexahydro-2-oxo-1H-thieno[3,4-d]imidazole ring systems A/B are excluded from the scope of the claims. A smaller genus is that in which 2-oxo-2,3-dihydro-1H-indole is excluded as a ring system A/B. As will be clear from examples A24 et seq below, only ring systems in the specific oxidation states set forth are excluded. a and b represent points of attachment of residues W and Y respectively, and a and b are in a peri relationship to one another on the fused A/B ring system. d and e represent points of fusion between ring A and ring B. W is a linker comprising from 2 to 8 atoms in a chain. Y is a linker comprising from 1 to 8 atoms in a chain. M is chosen from aryl, substituted aryl, heterocyclyl, substituted heterocyclyl, $C_6$ to $C_{20}$ alkyl and substituted $C_6$ to $C_{20}$ alkyl.

In one subgenus, the A/B ring system is a pair of fused 5-membered rings:

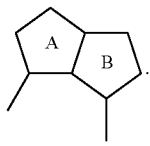

Examples of such 5/5 ring systems are:

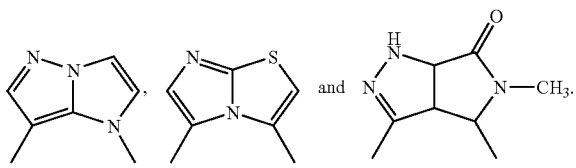

In another subgenus the A/B ring system is a pair of fused 6-membered rings:

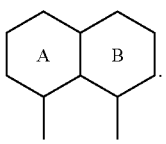

Examples of such 6/6 ring systems are:

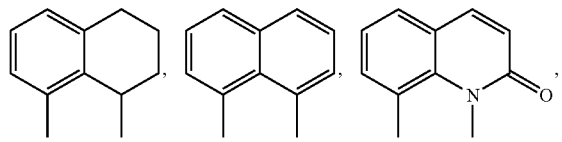

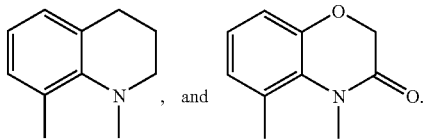

In another subgenus, the A/B ring system is a fused 5-and 6-membered ring pair:

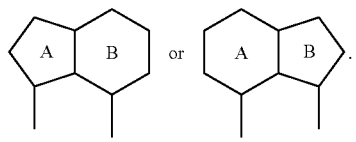

Examples of such 5/6 ring systems are indoles, indolines, isatins, benzimidazoles, benzoxazolinones, benzofurans, pyrrolopyrimidnediones and indazoles:

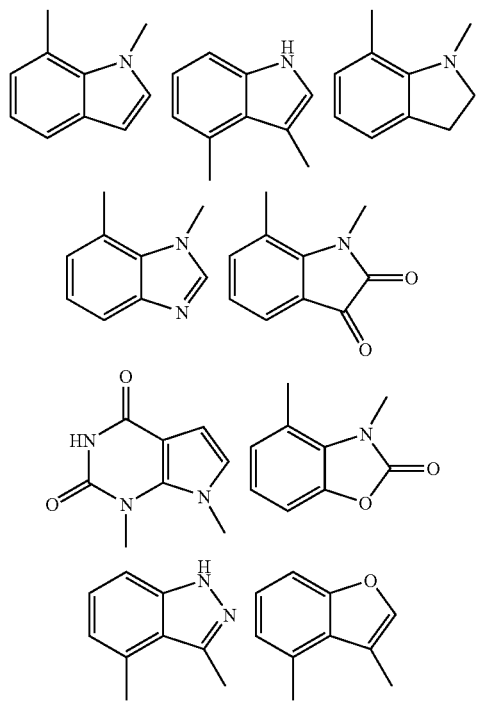

As indicated earlier, the ring system may be substituted, for example, 3-substituted-2-oxoindoles and the following:

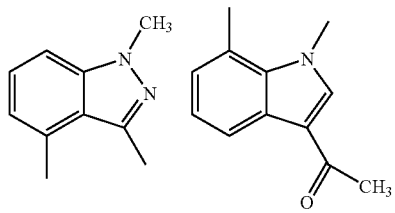

-continued

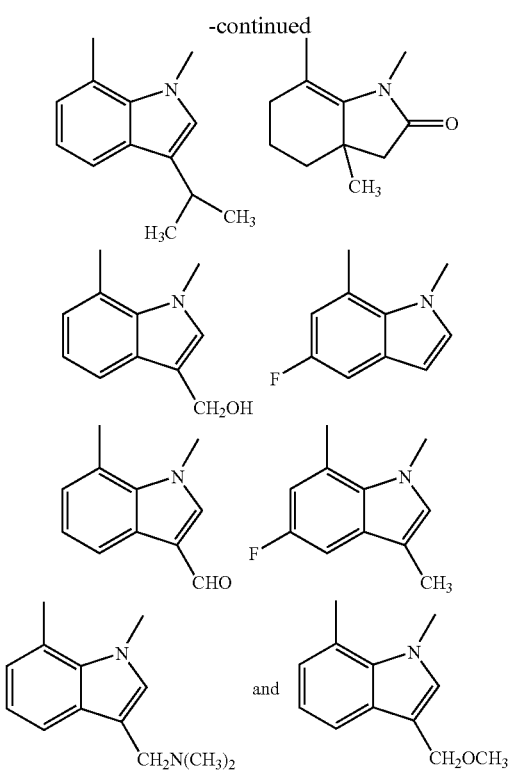

W and Y are linkers. W comprises from 2 to 8 atoms in a chain. Y comprises from 1 to 8 atoms in a chain. The chain may be branched or substituted, but it does not incorporate cyclic structures. W and Y may be $C_1$ or $C_2$ to $C_8$ alkyl in which one or two —$CH_2$— may be replaced by —O—, —C(=O)—, —CH=CH—, —$CF_2$—, —S—, —SO—, —$SO_2$—, —NH— or —N(alkyl)-. In common embodiments, W and Y are two-atom chains, i.e. $C_2$ alkyl in which one or both —$CH_2$— may be replaced by the groups named above. In one embodiment, W is chosen from —$CH_2CH_2$—, —$OCH_2$—, —C(=O)—, —$CH_2O$—, —$OCF_2$—, —OC$(CH_3)_2$—, —$OCH(CH_3)$—, —CH=CH—, —NHC(=O)— and —$NHCH_2$—; and Y is chosen from —$CH_2$—, —O—, —$OCH_2$—, —S—, —SO—, and —$SO_2$—. The left-hand bond indicates the point of attachment to ring A or B.

M is chosen from aryl, substituted aryl, heterocyclyl, substituted heterocyclyl, $C_6$ to $C_{20}$ alkyl and substituted $C_6$ to $C_{20}$ alkyl. In one embodiment, M is chosen from aryl, substituted aryl, heterocyclyl and substituted heteroaryl, more preferably from phenyl, substituted phenyl, naphthyl, substituted naphthyl, heteroaryl and substituted heteroaryl.

The single compound (E)-3-(4-benzyloxy-1H-indol-3-yl)-acrylic acid appears to have been disclosed, without utility, in the Rare Chemicals GmbH catalog. It is therefore excluded from the claims.

The compounds of the invention are acidic, allowing them to be presented as salts. The term "pharmaceutically acceptable salt" refers to salts whose counter ion derives from pharmaceutically acceptable non-toxic acids and bases. Suitable pharmaceutically acceptable base addition salts for the compounds of the present invention include, but are not limited to, metallic salts made from aluminum, calcium, lithium, magnesium, potassium, sodium and zinc or organic salts made from lysine, N,N-dialkyl amino acid derivatives (e.g. N,N-dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine) and procaine. When the compounds contain a basic residue, suitable pharmaceutically acceptable base addition salts for the compounds of the present invention include inorganic acids and organic acids. Examples include acetate, benzenesulfonate (besylate), benzoate, bicarbonate, bisulfate, carbonate, camphorsulfonate, citrate, ethanesulfonate, fumarate, gluconate, glutamate, bromide, chloride, isethionate, lactate, maleate, malate, mandelate, methanesulfonate, mucate, nitrate, pamoate, pantothenate, phosphate, succinate, sulfate, tartrate, p-toluenesulfonate, and the like.

DEFINITIONS

Throughout this specification the terms and substituents retain their definitions.

Alkyl is intended to include linear, branched, and, except when otherwise specified, cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s-and t-butyl and the like. Preferred alkyl and alkylene groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl, adamantyl and the like.

$C_1$ to $C_{20}$ Hydrocarbon includes alkyl, cycloalkyl, alkenyl, alkynyl, aryl and combinations thereof. Examples include benzyl, phenethyl, cyclohexylmethyl, camphoryl and naphthylethyl.

Alkoxy or alkoxyl refers to groups of from 1 to 8 carbon atoms of a straight, branched, cyclic configuration and combinations thereof attached to the parent structure through oxygen. Examples include methoxy, ethoxy, propoxy, isopropoxy, cyclopropyloxy, cyclohexyloxy and the like. Lower-alkoxy refers to groups containing one to four carbons.

Oxaalkyl refers to alkyl residues in which one or more carbons (and their associated hydrogens) have been replaced by oxygen. Examples include methoxypropoxy, 3,6,9-trioxa-decyl and the like. The term oxaalkyl is intended as it is understood in the art [see *Naming and Indexing of Chemical Substances for Chemical Abstracts*, published by the American Chemical Society, ¶196, but without the restriction of ¶127(a)], i.e. it refers to compounds in which the oxygen is bonded via a single bond to its adjacent atoms (forming ether bonds). Similarly, thiaalkyl and azaalkyl refer to alkyl residues in which one or more carbons have been replaced by sulfur or nitrogen, respectively. Examples include ethylaminoethyl and methylthiopropyl. The term "oxo" referring to a substituent intends double-bonded oxygen (carbonyl). Thus, for example, the excluded "oxo" ring systems are:

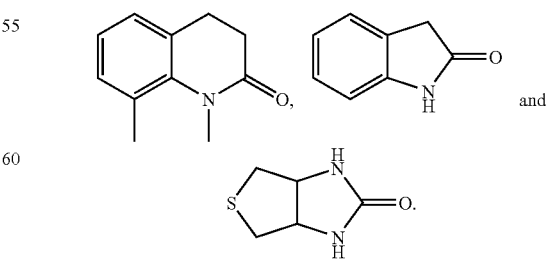

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include formyl, acetyl, propionyl, isobutyryl, t-butoxycarbonyl, benzoyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. Aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl means an alkyl residue attached to an aryl ring. Examples are benzyl, phenethyl and the like.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy. In the claims below, methylenedioxy and ethylenedioxy are mentioned as substituents. While methylenedioxy is attached at adjacent carbons on the ring, ethylenedioxy can be attached either at adjacent carbons on the ring or at the same carbon, forming a spirodioxole (ketal), analogous to the spirothiazolidinyl.

The term "halogen" means fluorine, chlorine, bromine or iodine.

The term "prodrug" refers to a compound that is made more active in vivo. Activation in vivo may come about by chemical action or through the intermediacy of enzymes. Microflora in the GI tract may also contribute to activation in vivo.

In the characterization of the variables, it is recited that A and B represent a pair of fused 5-, 6- or 7-membered rings and that the fused A/B ring system may contain from zero to four heteroatoms chosen from nitrogen, oxygen and sulfur. It is intended that these rings may exhibit various degrees of unsaturation from fully saturated to aromatic. Aromatic and partially unsaturated rings are preferred.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^2H$, $^3H$, $^{13}C$, $^{14}C$, $^{15}N$, $35S$, $^{18}F$, and $^{36}Cl$, respectively. Compounds that contain those radioisotopes and/or other radioisotopes of other atoms are within the scope of this invention. Tritiated, i.e. $^3H$, and carbon-14, i.e., $^{14}C$, radioisotopes are particularly preferred for their ease in preparation and detectability. Radiolabeled compounds of formula Ia of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

As used herein, and as would be understood by the person of skill in the art, the recitation of "a compound" is intended to include salts, solvates, co-crystals and inclusion complexes of that compound.

The term "solvate" refers to a compound of Formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents. Pharmaceutical co-crystals have recently become of considerable interest for improving the solubility, formulation and bioavailability of such drugs as itraconazole [see Remenar et al. *J. Am. Chem. Soc.* 125, 8456-8457 (2003)] and fluoxetine. Inclusion complexes are described in *Remington: The Science and Practice of Pharmacy* 19$^{th}$ Ed. (1995) volume 1, page 176-177. The most commonly employed inclusion complexes are those with cyclodextrins, and all cyclodextrin complexes, natural and synthetic, with or without added additives and polymer(s), as described in U.S. Pat. Nos. 5,324,718 and 5,472,954, are specifically encompassed within the claims. The disclosures of Remington and the '718 and '954 patents are incorporated herein by reference.

The terms "methods of treating or preventing" mean amelioration, prevention or relief from the symptoms and/or effects associated with lipid disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis. Throughout this application, various references are referred to. The disclosures of these publications in their entireties are hereby incorporated by reference as if written herein.

The term "mammal" is used in its dictionary sense. Humans are included in the group of mammals, and humans would be the preferred subjects of the methods of treatment.

The compounds described herein may contain asymmetric centers and may thus give rise to enantiomers, diastereomers, and other stereoisomeric forms. Each chiral center may be defined, in terms of absolute stereochemistry, as (R)- or (S)-. The present invention is meant to include all such possible isomers, as well as, their racemic and optically pure forms. Optically active (R)- and (S)-, or (D)- and (L)- isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr *J. Chem. Ed.* 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration. Thus, the formula II is intended to encompass pure enantiomers as well as racemic mixtures and any intermediate mixture of enantiomers:

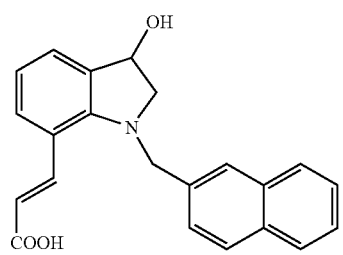

II whereas the formula III is intended to encompass either of the pure enantiomers of that structure:

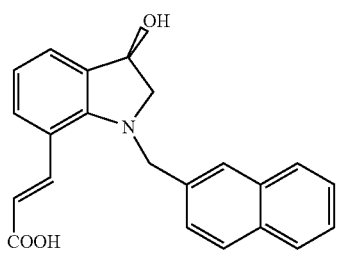

III and IV represents the pure, single, specified (S)-enantiomer:

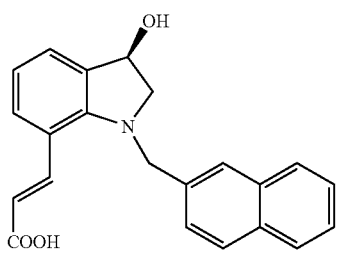

IV

The configuration of any carbon-carbon double bond appearing herein is selected for convenience only and unless explicitly stated, is not intended to designate a particular configuration. Thus the carbon-carbon double bond depicted arbitrarily above as E may be Z, E, or a mixture of the two in any proportion.

Terminology related to "protecting", "deprotecting" and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as *Protective Groups in Organic Synthesis* by T. W. Greene [John Wiley & Sons, New York, 1991], which is incorporated herein by reference. Particular attention is drawn to the chapters entitled "Protection for the Hydroxyl Group, Including 1,2- and 1,3-Diols" (pages 10-86).

The abbreviations Me, Et, Ph, Tf, Ts and Ms represent methyl, ethyl, phenyl, trifluoromethanesulfonyl, toluenesulfonyl and methanesulfonyl respectively. A comprehensive list of abbreviations utilized by organic chemists (i.e. persons of ordinary skill in the art) appears in the first issue of each volume of the *Journal of Organic Chemistry*. The list, which is typically presented in a table entitled "Standard List of Abbreviations" is incorporated herein by reference. In one embodiment, there are from one to three substituents and they are chosen independently from halogen, trifluoromethyl, methyl, methoxy, trifluoromethoxy, methanesulfonyl, methylenedioxy, and ethylenedioxy. For example, in compound A38 in Table 1, below, there are two substituents, chlorine and fluorine.

While it may be possible for the compounds of formula Ib to be administered as the raw chemical, it is preferable to present them as a pharmaceutical composition. According to a further aspect, the present invention provides a pharmaceutical composition comprising a compound of formula Ib, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula Ib or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder (including micronized and nanoparticulate powders) or granules; as a solution or a suspension in an aqueous liquid or a non-aqueous liquid; or as an oil-in-water liquid emulsion or a waterin-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation.

The dose range for adult humans is generally from 0.1 µg to 10 g/day orally. Tablets or other forms of presentation provided in discrete units may conveniently contain an amount of compound of the invention which is effective at such dosage or as a multiple of the same, for instance, units containing 5 mg to 500 mg, usually around 10 mg to 200 mg. The precise amount of compound administered to a patient will be the responsibility of the attendant physician. However, the dose employed will depend on a number of factors, including the age and sex of the patient, the precise disorder being treated, and its severity. The frequency of administration will depend on the pharmacodynamics of the individual compound and the formulation of the dosage form, which may be optimized by methods well known in the art (e.g. controlled or extended release tablets, enteric coating etc.)

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be.

Compounds representative of the invention have been synthesized. Their structures are shown in Table 1 below. All of the examples in table I have been synthesized, characterized and tested for EP3 receptor binding.

TABLE 1

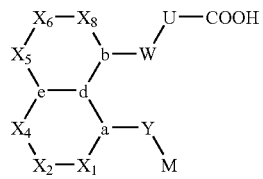

Compounds in Table 1, have 'd' = [C] except for compound A23, for which 'd' = N and compound A49, for which 'd' = CH

| Cmpd. No. A(x) | X1 | X2 | X4 | X5 | X6 | X8 | Y | W-U | M | a | b | e |
|---|---|---|---|---|---|---|---|---|---|---|---|---|
| A02 | CH | — | CH | N | — | CH | CH2 | CH=CH | 2-Naphth | N | C | N |
| A04 | C(=O) | — | O | CH | CH | CH | CH2 | OCH2 | 2-Naphth | N | C | C |
| A05 | C(=O) | — | O | CH | CH | CH | CH2 | OCH2 | [3,4-OCH2O]Ph | N | C | C |
| A06 | C(=O) | — | O | CH | CH | CH | CH2 | OCH2 | [3,4-Cl2]Ph | N | C | C |
| A07 | C(=O) | — | O | CH | CH | CH | CH2 | OCH2 | [2,4-Cl2]Ph | N | C | C |
| A08 | C(=O) | — | O | CH | CH | CH | CH2 | OCH2 | [2,5-(CH3)2]Ph | N | C | C |
| A09 | CH | — | C(CH3) | CH | CH | CH | CH2 | CH=CH | [2,4-Cl2]Ph | N | C | C |
| A10 | CH | — | C(CH2OH) CH | CH | CH | CH2 | CH=CH | [2,4-Cl2]Ph | N | C | C | |
| A11 | CH | — | C(CHO) | CH | CH | CH | CH2 | CH=CH | [2,4-Cl2]Ph | N | C | C |
| A12 | CH | — | C(CH2OCH3) | CH | CH | CH | CH2 | CH=CH | [2,4-Cl2]Ph | N | C | C |
| A13 | CH | — | C[C(CH3)=O] | CH | CH | CH | CH2 | CH=CH | [2,4-Cl2]Ph | N | C | C |
| A14 | CH | — | C[CH(CH3)2] | CH | CH | CH | CH2 | CH2—CH2 | [2,4-Cl2]Ph | N | C | C |
| A15 | C(=O) | — | C(OH)CF3 | CH | CH | CH | CH2 | CH=CH | 2-Naphth | N | C | C |
| A16 | C(=O) | — | C(OCH2CH2O) | CH | CH | CH | CH2 | CH=CH | [2,4-Cl2]Ph | N | C | C |
| A17 | C(=O) | — | C(=O) | CH | CH | CH | CH2 | CH=CH | [2,4-Cl2]Ph | N | C | C |
| A19 | C(=O) | — | C(CH3)2 | CH | CH | CH | CH2 | CH=CH | [2,4-Cl2]Ph | N | C | C |
| A20 | C(=O) | — | CF2 | CH | CH | CH | CH2 | CH=CH | [2,4-Cl2]Ph | N | C | C |
| A21 | CH | — | N | CH | CH | CH | CH2 | OCH2 | [2,4-Cl2]Ph | N | C | C |
| A22 | CH | — | N | CH | CH | CH | CH2 | OCH2 | 2-Naphth | N | C | C |
| A23 | CH | — | N | S | — | CH | CH=CH | CH2—CH2 | 2-Naphth | C | C | C |
| A24 | C(=O) | — | CH2 | CH2 | CH2 | CH2 | CH2 | CH=CH | 2-Naphth | N | C | C(CH3) |
| A25 | CH | CH | CH | NCH3 | — | N | O | NHCH2 | 2-Naphth | C | C | C |
| A26 | N | — | N(CH3) | CH | CH | CH | NHC(=O) | CH=CH | 2-Naphth | C | C | C |
| A27 | C(=O) | — | CH2 | CH2 | CH2 | CH2 | CH2 | CH=CH | [3-F]Ph | N | C | C(CH3) |
| A28 | C(=O) | — | CH2 | CH2 | CH2 | CH2 | CH2 | CH=CH | [4-F]Ph | N | C | C(CH3) |

TABLE 1-continued

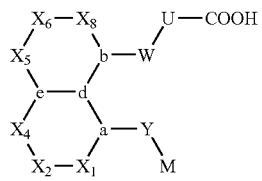

Compounds in Table 1, have 'd' = [C] except for compound A23, for which 'd' = N and compound A49, for which 'd' = CH

| Cmpd. No. A(x) | X1 | X2 | X4 | X5 | X6 | X8 | Y | W-U | M | a | b | e |
|---|---|---|---|---|---|---|---|---|---|---|---|---|
| A29 | C(=O) | — | CH2 | CH2 | CH2 | CH2 | CH2 | CH=CH | [3-MeO]Ph | N | C | C(CH3) |
| A30 | C(=O) | — | CH2 | CH2 | CH2 | CH2 | CH2 | CH=CH | [3,4-diF2]Ph | N | C | C(CH3) |
| A31 | CH | — | C(CH3) | CH | CF | CH | CH2 | CH=CH | [2,4-diCl2]Ph | N | C | C |
| A32 | C(=O) | — | CH2 | CH2 | CH2 | CH2 | CH2 | CH=CH | [2,4-diCl2]Ph | N | C | C(CH3) |
| A33 | C(=O) | — | N(CH3) | CH | CH | CH | C(=O)NH | CH=CH | [2,4-diCl2]Ph | C | C | C |
| A34 | C(=O) | — | CH2 | CH2 | CH2 | CH2 | CH2 | CH=CH | [3,4-diCl2]Ph | N | C | C(CH3) |
| A35 | C(=O) | — | CH2 | CH2 | CH2 | CH2 | CH2 | CH=CH | [3-Cl]Ph | N | C | C(CH3) |
| A36 | C(=O) | — | CH2 | CH2 | CH2 | CH2 | CH2 | CH=CH | [2,3-diCl2]Ph | N | C | C(CH3) |
| A37 | CH | CH | CH | N(CH3) | — | CH | O | CH=CH | [2,4-diF2]Ph | C | C | C |
| A38 | CH | CH | CH | N(CH3) | — | CH | O | CH=CH | [3-Cl-4-F]Ph | C | C | C |
| A39 | CH | CH | CH | N(CH3) | — | CH | O | CH=CH | [3,4-diCl2]Ph | C | C | C |
| A40 | CH | CH | CH | N(CH3) | — | CH | O | CH=CH | [2,4-diCl2]Ph | C | C | C |
| A41 | CH | CH | CH | N(CH3) | — | CH | O | CH=CH | [4-Cl]Ph | C | C | C |
| A42 | CH | CH | CH | N(CH3) | — | CH | O | CH=CH | [3,4-diF2]Ph | C | C | C |
| A43 | CH | CH | CH | N(CH3) | — | CH | O | CH=CH | [4-Cl-3-F]Ph | C | C | C |
| A44 | CH | CH | CH | N(CH3) | — | CH | O | CH=CH | 2-Naphth | C | C | C |
| A45 | CH | CH | CH | N(CH3) | — | CH | O | CH=CH | [4-Cl-2-F]Ph | C | C | C |
| A46 | CH | CH | CH | N(CH3) | — | CH | O | CH=CH | [2-Cl-4-F]Ph | C | C | C |
| A47 | C(=O) | — | CH2 | CH2 | CH2 | CH2 | CH2 | CH=CH | [2,4-diCl2]Ph | N | C | C(CO2Et) |
| A49 | C(=O) | — | CH2 | CH2 | CH2 | CH2 | CH2 | CH2CH2 | [3,4-diF2]Ph | N | CH | C(CH3) |
| A50 | C(=O) | — | CH2 | CH2 | CH2 | CH2 | CH2 | CH2CH2 | [3,4-diF2]Ph | N | C | C(CH3) |
| A51 | C(=O) | CH2 | O | CH | CH | CH | CH2 | NHC(=O) | 2-Naphth | N | C | C |
| A53 | CH | — | CH | CH | CH | CH | CH2 | CH=CH | 2-Naphth | N | C | C |
| A55 | CH | — | CCH2N(CH3)2 | CH | CH | CH | CH2 | CH=CH | 2-Naphth | N | C | C |
| A56 | C(=O) | — | C(=O) | CH | CH | CH | CH2 | CH=CH | 2-Naphth | N | C | C |
| A57 | CH | — | C(CH3) | CH | CF | CH | CH2 | CH=CH | 2-imidazo[1,2-a]pyridine | N | C | C |
| A58 | CH | — | CH | CH | CH | CH | CH2 | CH2CH2 | 2-Naphth | N | C | C |
| A60 | C(=O) | — | C(=O) | CH | CH | CH | CH2 | CH=CH | [3,4-diF2]Ph | N | C | C |
| A62 | C(=O) | — | C(CH2OH)2 | CH | CH | CH | CH2 | CH=CH | [2,4-diCl2]Ph | N | C | C |
| A63 | C(CH3) | — | CH | C(=O) | N(CH3) | C(=O) | CH2 | CH2CH2 | [2,4-diCl2]Ph | N | N | C |
| A64 | | | | | | | | | | | | |

The compounds of the invention were assayed for their binding on prostanoid EP3 receptors according to the method of Abramovitz et al. [*Bioch. Biophys. Acta,* 1473, 285-293 (2000)]. Chart 1 shows the activity in column 2. Compounds with $IC_{50}$<1 μM are shown as +++; compounds with $IC_{50}$ 1-10 μM are shown as ++; and compounds with $IC_{50}$>10 μM are shown as +.

Processes for obtaining the compounds of the invention are presented below. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Generally compounds of the Formula I may be prepared from appropriately functionalized substituted bicyclo cores as shown in schemes 1 to 14. In particular when node "a" is a nitrogen atom, one may either first functionalize the carbon atom, node "b", of bicycle core G1 (which in Scheme 1 is a halogen atom) via palladium mediated Heck coupling to provide carbon linked ester (G2). Otherwise the linkage at 'node b=C', may be functionalized thru a heteroatom (G5) as shown in Scheme 2. The intermediates G2 and G5 then may be functionalized at the node "a" (a nitrogen atom of a bicycle core) to provide peri-substituted esters G3 and G6, respectively. The hydrolysis of the ester provides the carboxylic acid (G4 or G7), which are encompassed by the Formula I.

Compounds representative of the invention have been synthesized. Their structures are shown in Table 1 below. All of the examples in table 1 have been synthesized, characterized and tested for EP3 receptor binding.

The compounds of the invention were assayed for their binding on prostanoid EP3 receptors according to the method of Abramovitz et al. [*Bioch. Biophys. Acta.* 1473, 285-293 (2000)]. Chart 1 shows the activity in column 2. Compounds with $IC_{50}$<1 μM are shown as +++; compounds with $IC_{50}$ 1-10 μM are shown as ++; and compounds with $IC_{50}$>10 μM are shown as +.

| Cmpd. No. A(x) | Activity |
|---|---|
| A02 | ++ |
| A04 | ++ |
| A05 | ++ |
| A06 | ++ |
| A07 | ++ |
| A08 | ++ |
| A09 | +++ |
| A10 | ++ |
| A11 | +++ |
| A12 | +++ |
| A13 | ++ |
| A14 | ++ |
| A15 | ++ |
| A16 | +++ |
| A17 | ++ |
| A19 | ++ |
| A20 | ++ |
| A21 | +++ |
| A22 | + |
| A23 | ++ |
| A24 | ++ |
| A25 | +++ |
| A26 | ++ |
| A27 | +++ |
| A28 | +++ |
| A29 | +++ |
| A30 | ++ |
| A31 | +++ |
| A32 | +++ |
| A33 | ++ |
| A34 | +++ |
| A35 | ++ |
| A36 | ++ |
| A37 | +++ |
| A38 | ++ |
| A39 | ++ |
| A40 | +++ |
| A41 | ++ |
| A42 | ++ |
| A43 | +++ |
| A44 | +++ |
| A45 | +++ |
| A46 | ++ |
| A47 | +++ |
| A49 | ++ |
| A50 | ++ |
| A51 | + |
| A53 | +++ |
| A55 | ++ |
| A56 | +++ |
| A57 | ++ |
| A58 | +++ |
| A60 | ++ |
| A62 | +++ |
| A63 | ++ |
| A64 | ++ |

Processes for obtaining the compounds of the invention are presented below. In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here.

Generally compounds of the Formula I may be prepared from appropriately functionalized substituted bicyclo cores as shown in schemes 1 to 14. In particular when node "a" is a nitrogen atom, one may either first functionalize the carbon atom, node "b", of bicycle core G1 (which in Scheme 1 is a halogen atom) via palladium mediated Heck coupling to provide carbon linked ester (G2). Otherwise the linkage at 'node b=C', may be functionalized thru a heteroatom (G5) as shown in Scheme 2. The intermediates G2 and G5 then may be functionalized at the node "a" (a nitrogen atom of a bicycle core) to provide peri-substituted esters G3 and G6, respectively. The hydrolysis of the ester provides the carboxylic acid (G4 or G7), which are encompassed by the Formula I.

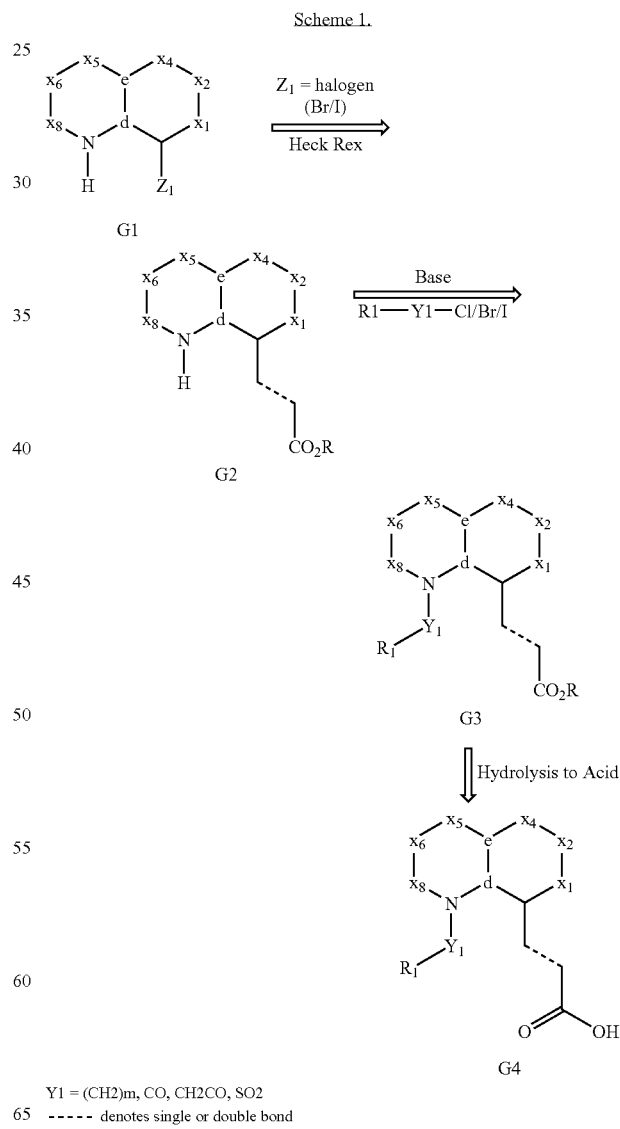

Scheme 1.

$Y_1$ = $(CH_2)_m$, CO, $CH_2CO$, $SO_2$
----- denotes single or double bond

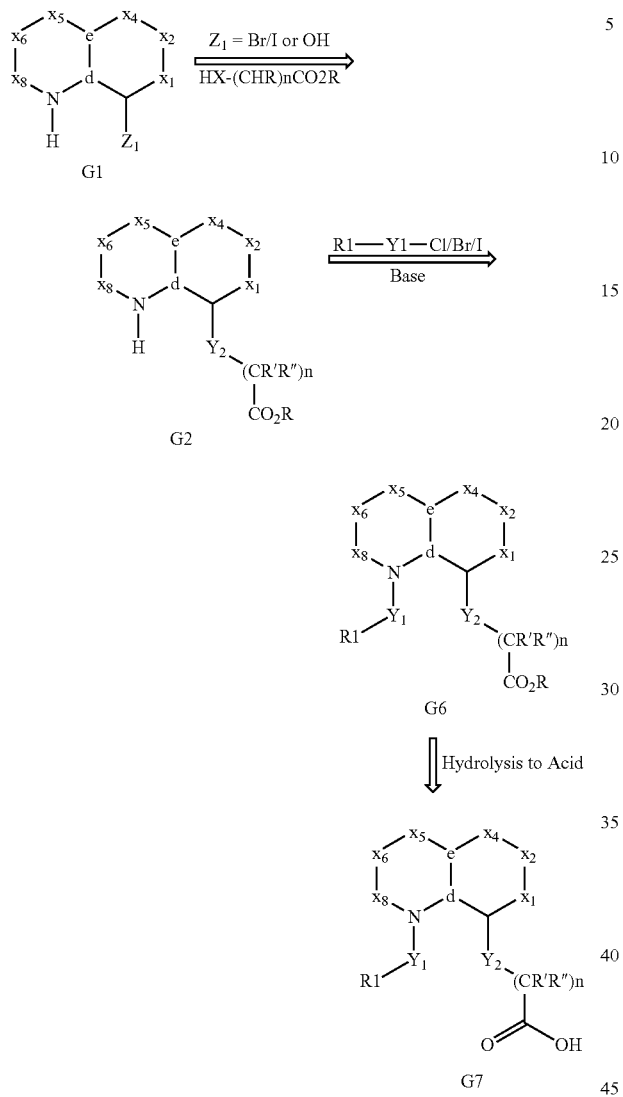

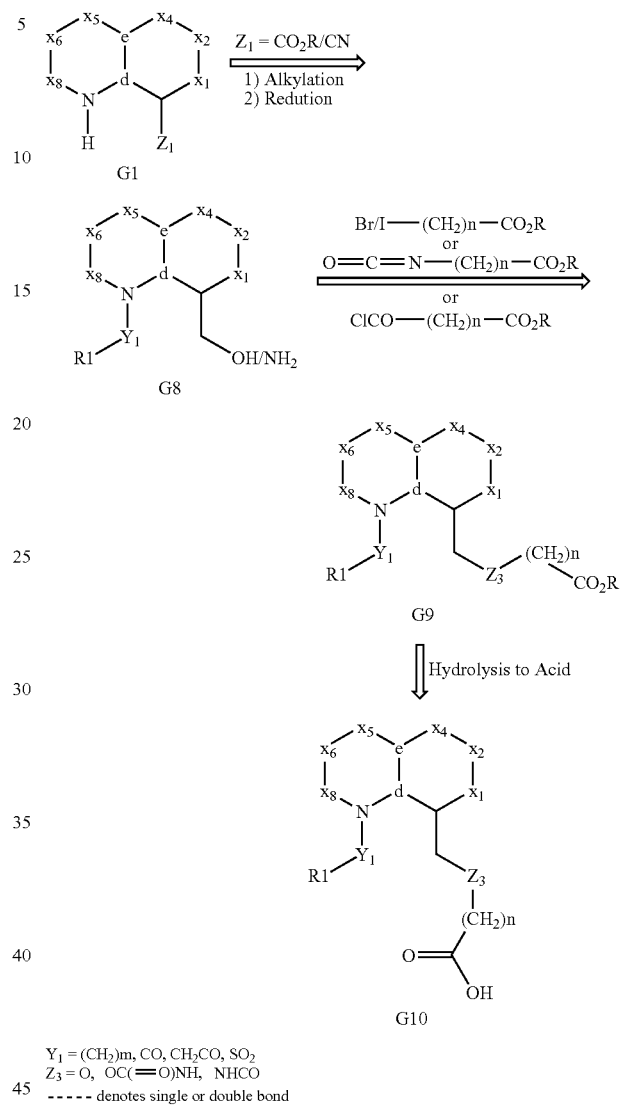

When the node "b" as carbon bears an ester or a nitrile functional group, reduction provides the corresponding alcohol or amine, G8, as in Scheme 3 and 4. The alcohol or amine may be subsequently alkylated, acylated or reacted with an isocyanate to provide peri-substituted bicyclic intermediate G9, which in turn can be converted to compounds of formula I, where the linker contain diverse tethers, as depicted in G10. Alternatively, amine G8 may be reacted with cyclic (saturated or aryl/heteroaryl) isocyanates bearing a carboxylate ester to provide a more rigid cyclic linker separating the bicyclic core and the acyl sulphonamide functionality as in G11 (Scheme 4). In similar fashion, the derivatives wherein the carbon of the bicylic core G1 directly bears a nitrogen (e.g. nitro/amine, G13/G14) provide corresponding amides or ureas as spacer for the carboxylic acid G16, as shown in Scheme 5.

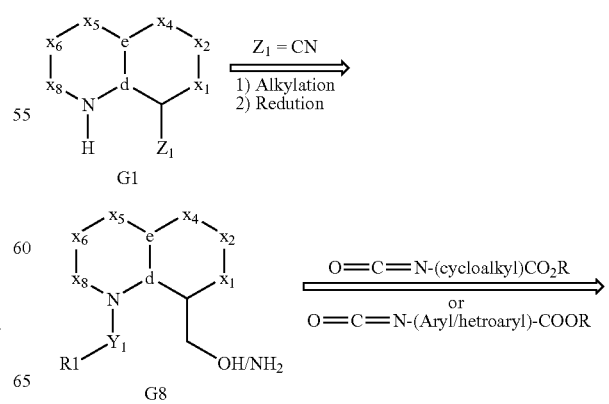

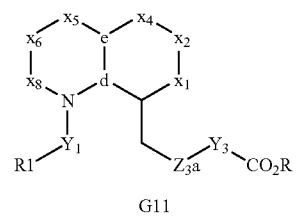

G11

⇓ Hydrolysis to Acid

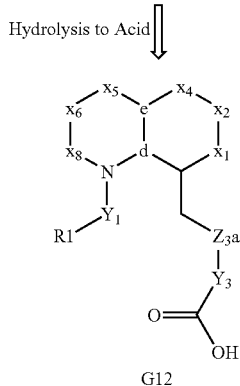

G12

Y1 = (CH2)m, CO, CH2CO, SO2
Z3a = O(CO)NH, NHCONH
Y3 = cylcoalkyl, aryl hetroaryl

Scheme 5.

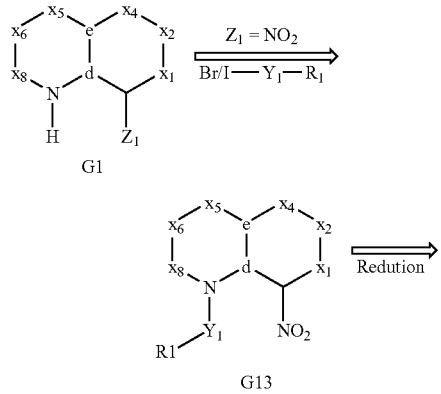

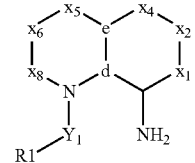

G14

⇓ Br/I—CR″R″)(CH2)nCOOR
or
O=C=N—(CH2)n—CO2R
or
ClCO—(CH2)n—CO2R

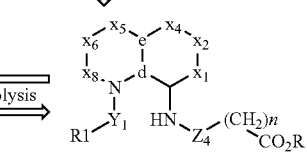

G16  ⇌ Hydrolysis ⇌  G15

Z4 = CR′R″, CO, CONH
Y1 = (CH2)m, CO, CH2CO, SO2

Bicyclic cores wherein both the nodes "a" and "b" are carbons, can be obtained from starting materials such as G17. The fuctionalization of the halogen bearing carbon through a palladium-mediated ether or amine formation via Buchwald chemistry, followed by introduction of an acyl or formyl group via electrophilic reaction provides the key peri-functionalized intermediate G18. The latter reaction is particularly applicable where the ring (b) of the bicyclic core is electron rich. Reaction of the ketone or aldehyde by a Wittig reagent yields the desired olefin linked ester, which may be reduced to provide corresponding saturated linker, if desired. Alternatively, the ketones or aldehydes may be reacted with appropriate enolate (or even homo-enolate) to provide additional functional groups (Y4=OH, e.g.) in the linker portion, to provide G20. The functional group Y4 may be further derivatized, or eliminated to provide the olefin linkage. In addition, the benzylic alcohol of G19 may be converted to a halide (e.g. Br) and the benzylic halide may thus be converted via Heck coupling or alternatively reacted with ICH2CH2COOR [Higuchi K. et. Al. Org. Letters 2003 3704-3704] to provide product G22. The aldehyde/ketone G18 upon reaction with a homo-enolate provides the ester G20. Subsequent hydrolysis of G20 or G22 leads to the acids G21 and G23, respectively.

Scheme 6.

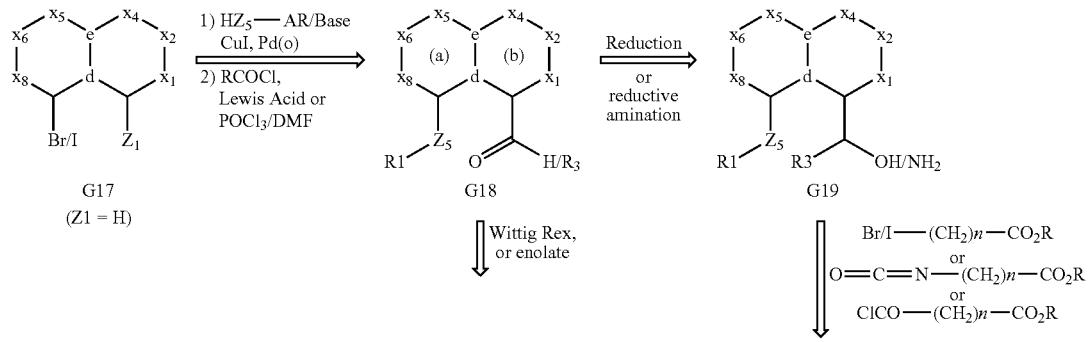

-continued

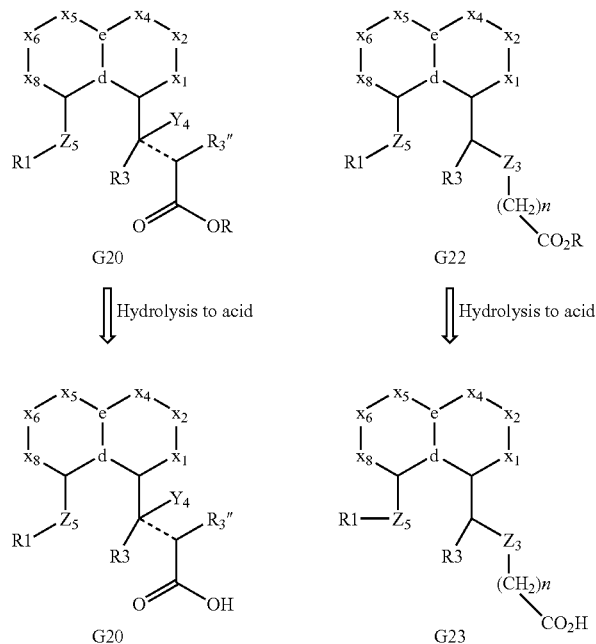

$Z_3$ = O, OC(=O)NH, NHCO
$Z_5$ = O, $NR_3$

- - - - - denotes single or double bond

Additional examples of highly reactive/electrophilic bicyclic cores, in which introduction of heteroatom-linked functionalities provides access to both carbon-linked peri-functionalities, are shown in scheme 7 and 8. These synthetic routes provide means to introduce the acyl portion of the fragment containing diverse linkers. These chemistries provide for introduction of sulphur linked aryl and heteroaryl groups and allow for adjustment of sulphur oxidation state, as well, thus providing access to analogs represented by G28 and G33. Alternatively, by use of ketones G34, one may prepare compounds related to G28/G33, which provide access to cores such as benzofuran and benzothiophene, G37

Scheme 7.

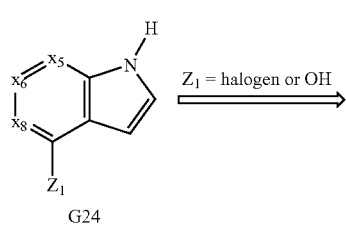

-continued

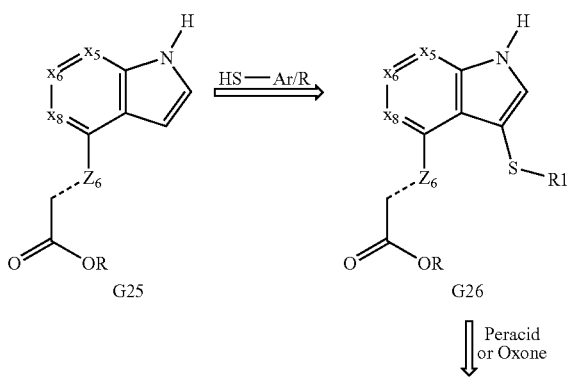

$Z_6$ = O, $O(CH_2)m$, CH

- - - - - denotes single or double bond

Scheme 8.

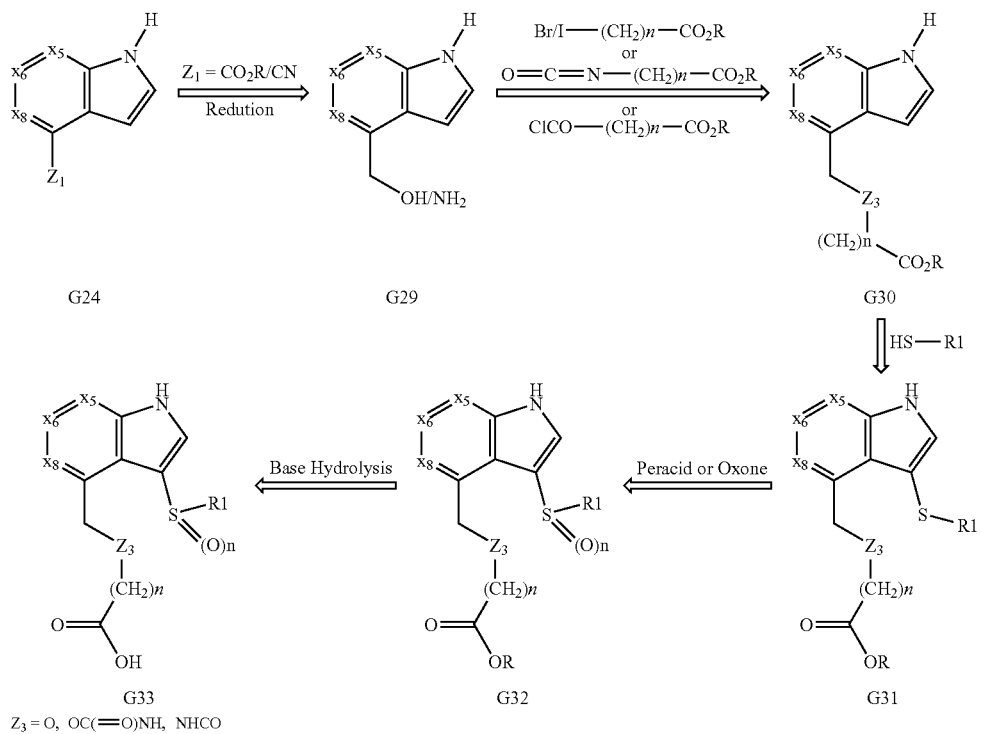

G33
$Z_3 = O, OC(=O)NH, NHCO$

Scheme 9.

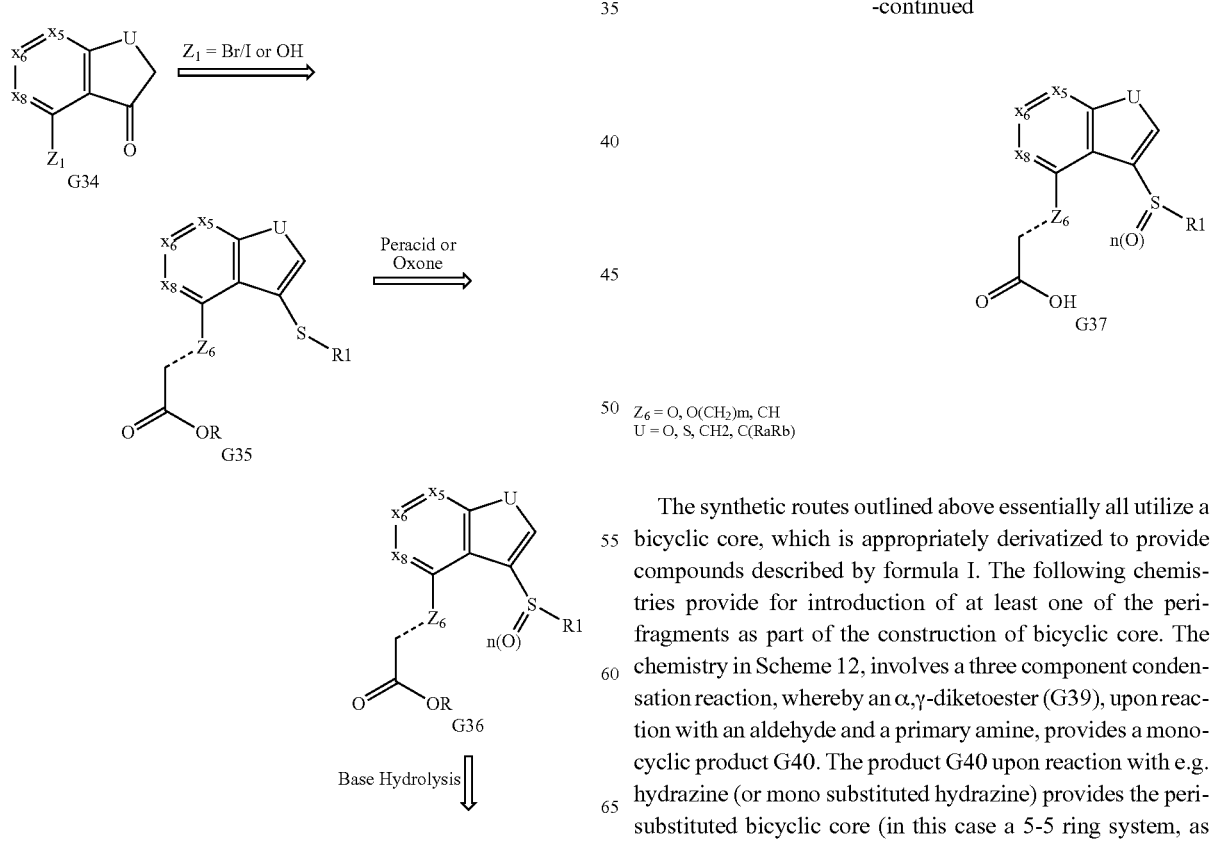

$Z_6 = O, O(CH_2)m, CH$
$U = O, S, CH2, C(RaRb)$

The synthetic routes outlined above essentially all utilize a bicyclic core, which is appropriately derivatized to provide compounds described by formula I. The following chemistries provide for introduction of at least one of the peri-fragments as part of the construction of bicyclic core. The chemistry in Scheme 12, involves a three component condensation reaction, whereby an α,γ-diketoester (G39), upon reaction with an aldehyde and a primary amine, provides a monocyclic product G40. The product G40 upon reaction with e.g. hydrazine (or mono substituted hydrazine) provides the peri-substituted bicyclic core (in this case a 5-5 ring system, as shown by G41), which then leads to the analog G42.

Scheme 10.

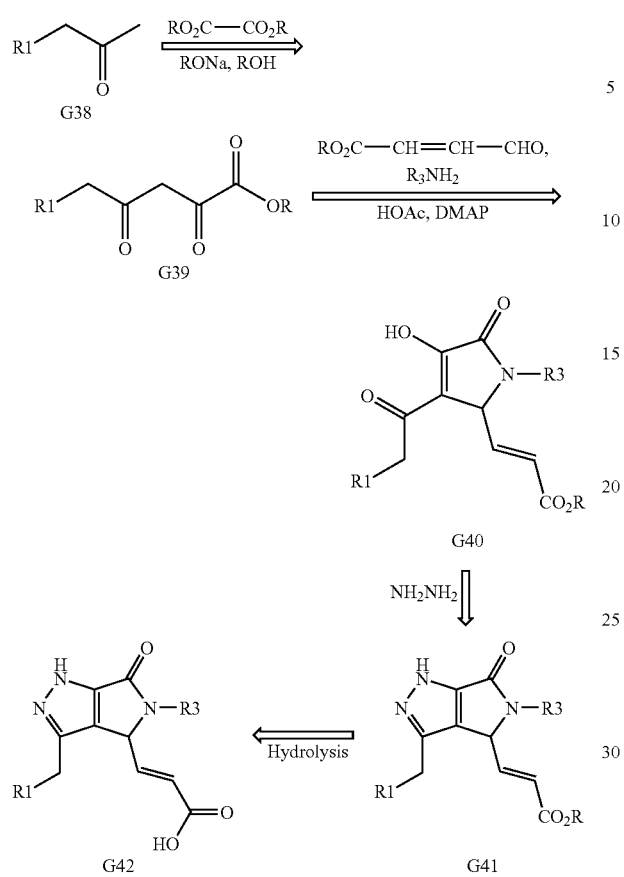

Scheme 11.

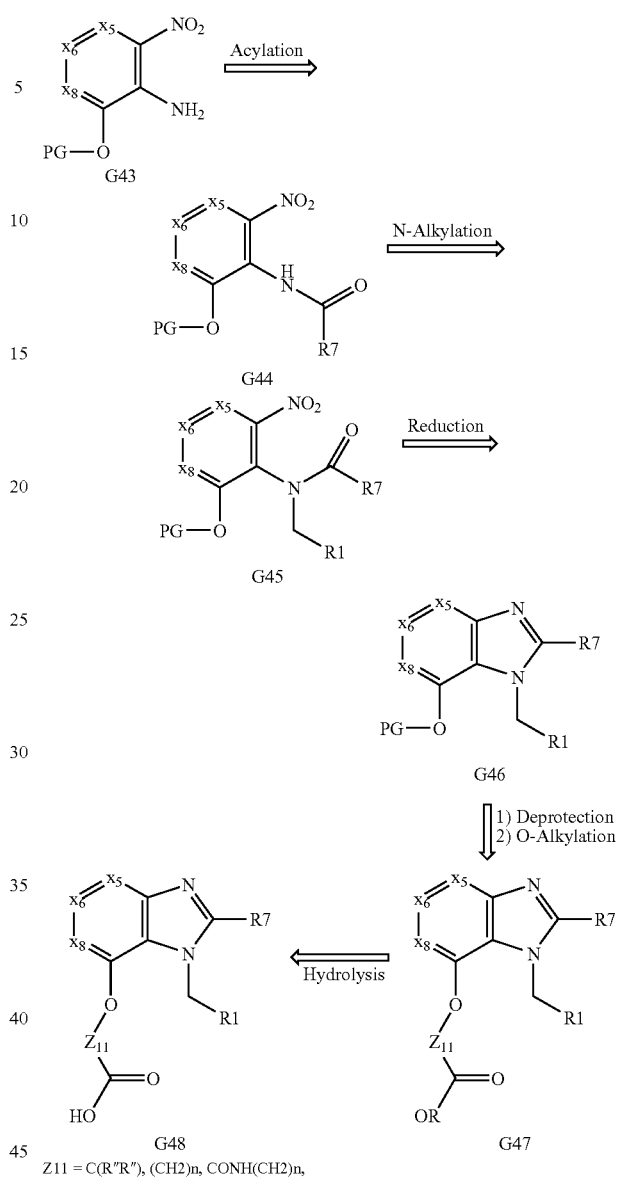

Other examples of chemistries that involve formation of bicyclic cores are outlined in Schemes 11 and 12, which present syntheses of benzimidazole-based cores. In order to prepare a peri-substituted system, the R1 group is introduced regiospecifically at step G44-G45, which, upon subsequent ring closure, provides the desired peri-substituted derivative G46. In Scheme 12, the desired regiospecific introduction of the R1 group is accomplished by O->N acyl migration followed by reduction of amide to secondary amine. In this case, ring closure also provides the desired peri-substituents, as by G54.

Scheme 12.

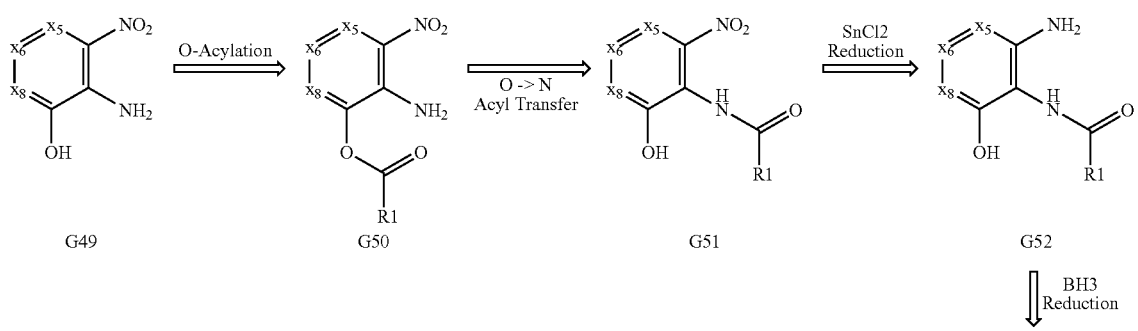

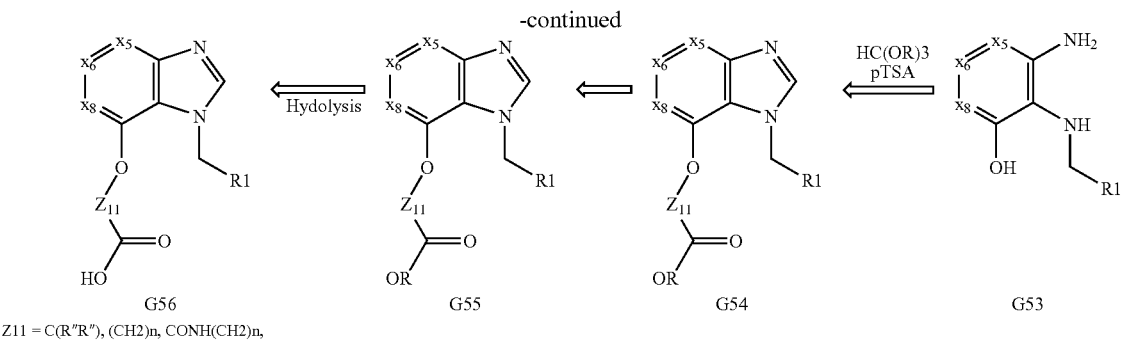

Z11 = C(R''R''), (CH2)n, CONH(CH2)n,

Another example of the chemistries involved in formation of bicyclic cores with desired peri-functionalization is depicted in Scheme 13. Here, a thermal cyclization of an amine with a cyclic disposed γ-keto acid G59 provides the required bicyclic intermediate G60. Bromination followed by e.g. Heck reaction provides the desired peri-bicyclic derivative G62 that upon ester deprotection provides the acid G63. This chemistry allows synthesis of essentially non aromatic ring systems and also provides for formation of bicyclic ring systems wherein the ring (a) is 5-membered. Ring (a) is produced during the cyclization reaction, whereas the size of the ring (b) is controlled by the use of the cyclic ketone at the initial step of the synthesis and thus allow for formation of "5-N" bicyclic system. In addition to the size, the substituent and presence of heteroatoms in the cyclic ketone also allows flexibility. The nature of the tertiary group may also be varied and this may be introduced at the cyclic ketone stage, which allows significant control over its regiochemistry. The positions X5/X6 may be heteroatoms and/or contain additional substituents as well.

Scheme 13.

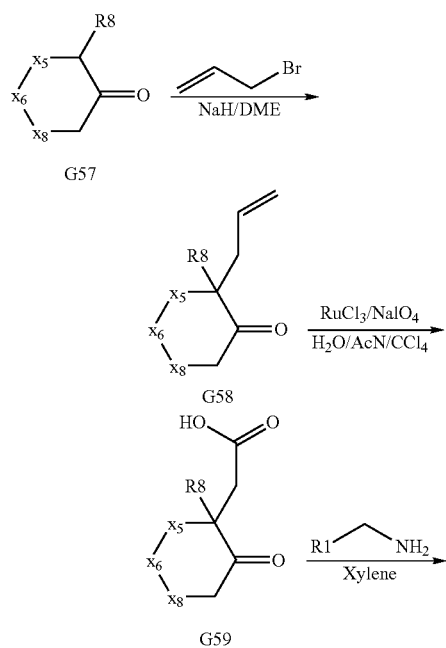

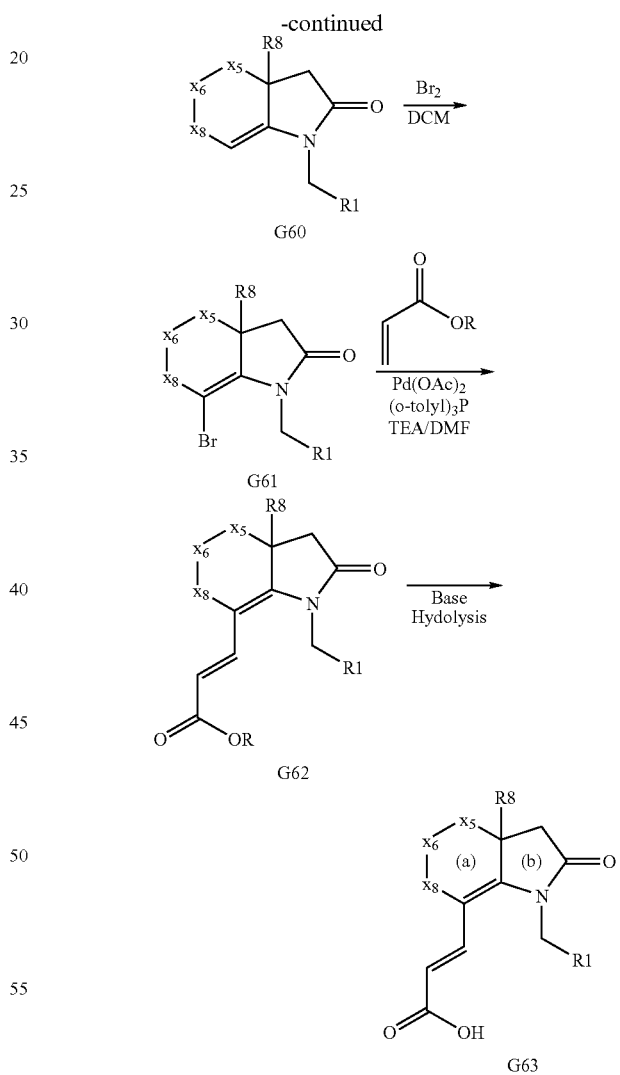

An example which allows the introduction of an acyl fragment (bearing R2) via electrophilic reaction is shown in Scheme 14. This leads to preparation of analogs represented by G66 and G67. The benzylic carbonyl group present in G90 and G91 may be further derivatized, e.g. by reduction to alcohol or $CH_2$, formation of oxime, imines or hydrzides, ketals, etc. The late stage reduction also allows one tom introduce radiolabled carbon ($^{14}$C) or tritium ($^{3}$H) to provide analogs for various in-vitro and or in-vivo studies

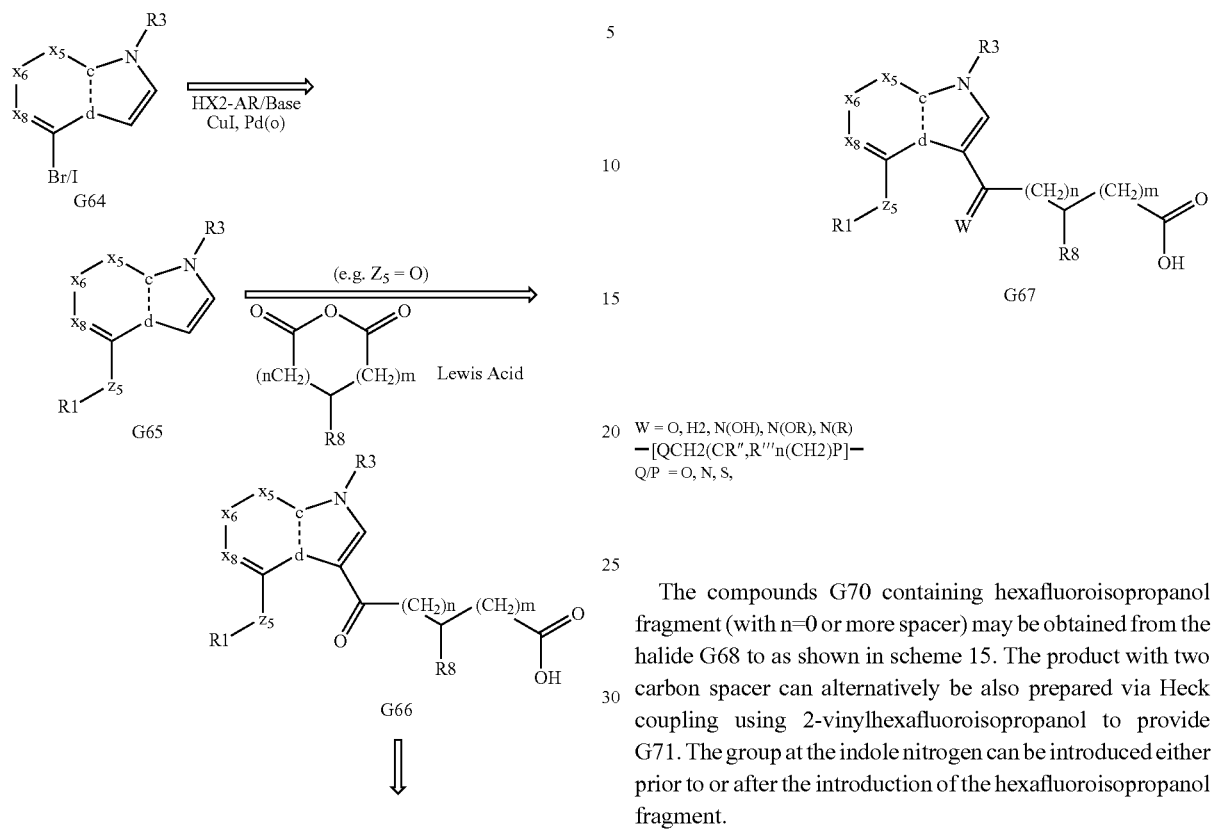

-continued

The compounds G70 containing hexafluoroisopropanol fragment (with n=0 or more spacer) may be obtained from the halide G68 to as shown in scheme 15. The product with two carbon spacer can alternatively be also prepared via Heck coupling using 2-vinylhexafluoroisopropanol to provide G71. The group at the indole nitrogen can be introduced either prior to or after the introduction of the hexafluoroisopropanol fragment.

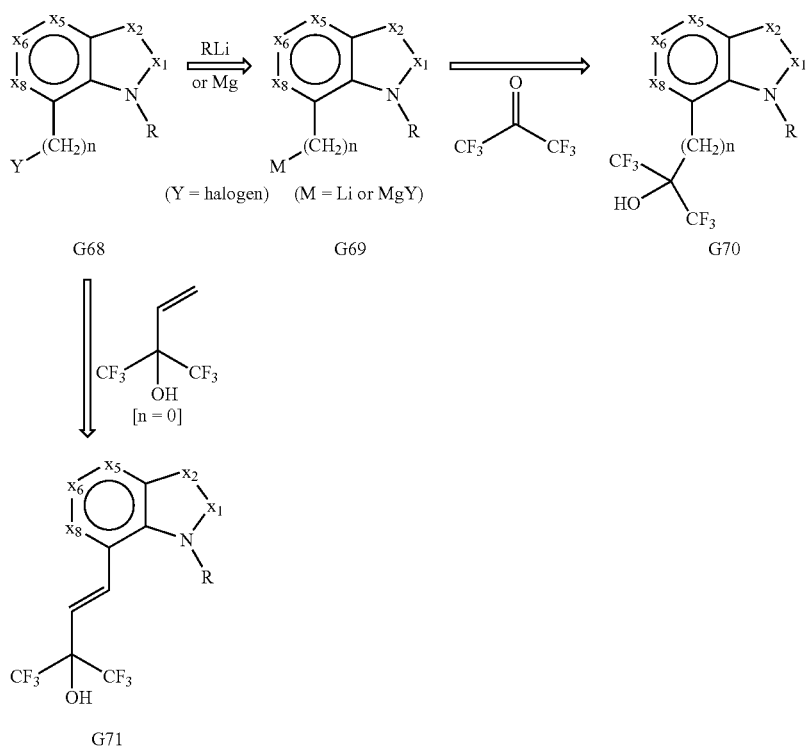

Finally, several appropriately functionalized bicylic cores are either commercially available or their syntheses are described in the published literature or could be inferred by one skill in the art. Examples of several of these are described as part of the Specific Examples and some of these are summarized below.

For bicyclic systems wherein one of the nodes is nitrogen, indole derivatives serve as a readily accessible and useful core. The 4-bromo and 4-hydroxy indoles are commercially available. The 7 substituted indoles, e.g. 7-$CO_2$R, 7-alkoxy, 7-benzyloxy, etc. can be prepared by Batcho-Leimgruber chemistry from appropriately substituted 2-nitrotoluene, (Org Synthesis Co, Vol. 7). This approach also provides access to 7-Me, 7-CHO, 7-CN, and 7-OH indoles by functional group manipulations. Alternatively, the 7-halo indoles are accessible from 2-halo anilines via Bartoli chemistry (Bartoli, G. et.al. Tett. Letters, 1989, 30, 2129-2132). Diverse 7-substituted indoles may also be prepared via selective fuctionalization of indole via directed ortho metalation according to the procedure of Snieckus, [Snieckus V. et.al. Org Letters 2003, 1899-1902]. These various approaches also provide access to other substituted indole derivatives. The 8-hydroxytetrahydroquinolines, a [6:6]-based core, can be obtained from commercially available 8-hydroxy quinoline by reduction. 8-OH-1H-Quinolin-2-one. 2,6-dihydroxy anilines or related heterocycles may be transformed to 5-hydroxy-4H-benzo[1,4]oxazin-3-one, 5-hydroxy-4H-benzo[1,4]oxazin-2,3-dione, 4-hydroxy-3H-benzooxazol-2-one, bicyclic derivatives. Various anilines may be converted to isatin analogs using the literature procedures, and examples of these are described in the specific example section below. Synthesis of a series of [5:5] bicyclo cores (e.g. imidazothiazole and pyrrolopyarzolone) are described in the specific examples. A diverse group of [6:5] bicyclo cores can also be obtained analogous to literature syntheses of cores such as imidazopyridine and imidazopyrimidine [Katritzky A. R. et.al. JOC 2003, 68, 4935-37], pyrrolopyrimides [Norman M. et.al. JMC 2000, 43, 4288-4312]. These diverse bicyclo cores may then be derivatized to provide analogs of formula.

Overall, the range of chemistries shown above allows for preparation of potent prostenoid antagonists/agonists. The chemistry allows manipulation of the core structure and introduction of optimal functional groups to provide a desired balance of hydrophobicity-hydrophilicity; it allows introduction of hydrogen bond donor and acceptors with desired topology; it allows adjustment of desired physical characteristics suitable for achieving desired pharmaceutical and ADME properties (e.g. membrane permeability, low plasma protein binding, desired metabolic profile etc.). The ability to adjust physical characteristics permits suitable formulation for oral bioavailability, which in turn allows for control over the size and frequency of dose administered to mammals to achieve desired pharmacological response. The ability to adjust metabolic profile allows for minimizing potential for drug-drug interactions. Thus the scope of this invention not only provides for preparation of potent prostenoid antagonists with proper isozyme selectivity to be useful tools for research, it also provides compounds are of value in therapy.

The following specific non-limiting examples are illustrative of the invention:

EXAMPLE 1

Preparation of A25

2-Fluoro-6-(naphthalen-2-yloxy)-benzonitrile (K-1). To a 20 mL vial containing a magnetic stir bar was added sodium hydride (103.7 mg, 4.32 mmol, 60% in mineral oil) followed by anhydrous DMF (2 mL) resulting in gas evolution. To this stirring reaction mixture was added 2-naphthol (623 mg, 4.32 mmol) as a solid in small portions over 5 min. The mixture was stirred at room temperature for 3 min and then 2,6-difluorobenzonitrile (601 mg, 4.32 mmol) in anhydrous DMF (4 mL) was added in one portion. The reaction mixture was heated in an oil bath at 100° C. for a total of 2 h and allowed to cool to room temperature. The reaction mixture was diluted with water (15 mL) and the resulting mixture was extracted with EtOAc (2×20 mL). The combined organic extracts were washed with water (3×20 mL), dried ($Na_2SO_4$), filtered and concentrated to give K-1 as brown solid (1.216 g) of sufficient purity (contained 2-naphthol) to be used in the subsequent step. 1H NMR.

1-Methyl-4-(naphthalen-2-yloxy)-1H-indazol-3-ylamine (K-2). To a 20 mL vial containing K-1 (966 mg, 3.67 mmol) and a magnetic stir bar was added anhydrous N,N-dimethylacetamide (4 mL) and the mixture was stirred until solution was achieved. Methyl hydrazine (390 µL, 7.34 mmol) was added and the vial was capped and the reaction mixture was placed in an oil bath at 120° C. and stirred at that temperature overnight. The reaction mixture was heated at 130° C. for an additional 3 h. The cooled reaction mixture was diluted with water (20 mL) and extracted with EtOAc (2×30 mL). The combined organics were washed with water (3×15 mL), dried ($Na_2SO_4$), filtered and concentrated to give 1.03 g of a tan solid. This residue was purified via flash chromatography on silica gel (120 g) utilizing $CH_2Cl_2$ and then 9:1 $CH_2Cl_2$/EtOAc as eluent to give 770 mg of K-2 as an off-white solid. This material was deemed of sufficient purity to be utilized in subsequent reactions. 1H NMR, MS.

1-Methyl-4-(naphthalen-2-yloxy)-1H-indazol-3-ylamino]-acetic acid methyl ester (K-3). To a 5 mL vial containing a magnetic stir bar was added K-2 (147 mg, 0.508 mmol), acetone (1 mL), methyl bromoacetate (0.053 mL, 0.559 mmol) and potassium carbonate (84 mg, 0.61 mmol). The reaction mixture was stirred overnight at room temperature and then heated in an oil bath at 60° C. for an additional 24 h. The solvent was evaporated and the residue was suspended in 9:1 $CH_2Cl_2$/acetone and subjected to flash chromatography purification on flash silica gel (10 g) utilizing 9:1 $CH_2Cl_2$/acetone as eluent. The fractions containing the desired compound were combined and concentrated to give 96 mg of K-3 of acceptable purity to be taken on to the next step. 1H NMR.

[1-Methyl-4-(naphthalen-2-yloxy)-1H-indazol-3-ylamino]-acetic acid (A25) To a 50 mL round-bottomed, one-necked flask containing K-3 (90 mg, 0.25 mmol) was added 1:1 EtOH/$H_2O$ (2 mL). To this stirring suspension was added 15% aqueous NaOH (0.133 mL, 0.5 mmol) and the reaction mixture was allowed to stir at room temperature overnight. The reaction mixture was concentrated on the vacuum line and the resulting solid was suspended in $H_2O$ (2 mL) and 1N HCl was added until a pH of 1-2 (litmus paper) was reached. The mixture was stirred at room temperature for 30 min and then filtered. The resulting solid was dried to afford 65 mg (75%) of A25 as an off-white solid. 1H NMR (400 MHz, DMSO-d6) 3.77 (s, 3H), 3.93 (s, 2H), 5.63 (br s, 1H), 6.18 (d, J=7.6 Hz, 1H), 7.07 (d, J=8.0 Hz, 1H), 7.18 (dd, J=8.0, 8.0 Hz, 1H), 7.41 (dd, J=8.8, 1.2 Hz, 1H), 7.51 (m, 2H), 7.63 (d, J=2.4 Hz, 1H), 7.89 (d, J=8.0 Hz, 1H), 7.96 (d, J=7.6

Hz, 1H), 8.02 (d, J=8.8 Hz, 1H), 12.45 (br s, 1H), LC/MS (86%) (ESI+) Calcd. for 347.4; Found: 348.7 (M+1).

EXAMPLE 2

Preparation of A26

4-Iodo-1-methyl-1H-indazol-3-ylamine (K-4). To a 50 mL pressure vessel was added 2-fluoro-6-iodobenzonitrile (500 mg, 2.02 mmol) and N,N-dimethylacetamide (5 mL). To this stirring solution was added methyl hydrazine (139 μL, 2.63 mmol) and the sealed vessel was heated to 80° C. for 2 h followed by heating at 120° C. for 16 h. The cooled reaction mixture was diluted with water and extracted with EtOAc (3×). The combined organic extracts were washed with water, dried ($Na_2SO_4$), filtered and concentrated. The resulting semisolid was triturated with hexanes/EtOAc (1:1) and the resulting solid was filtered, washed with EtOAc and dried. This operation afforded 149 mg of a light brown solid. The aqueous washes from above were extracted with EtOAc to afford an additional 327 mg of product. Total yield was 476 mg (85%) of K-4. 1H NMR, MS.

Naphthalene-2-carboxylic acid (4-iodo-1-methyl-1H-indazol-3-yl)-amide (K-5). To an oven-dried 25 mL, three-necked, round-bottomed flask was added K-4 (470 mg, 1.71 mmol), anhydrous THF (7 mL) and $Et_3N$ (0.477 mL, 3.42 mmol). The solution was cooled to 0° C. under a $N_2$ atmosphere and 2-naphthoyl chloride (326 mg, 1.71 mmol) was added in one portion. The reaction mixture was allowed to warm to room temperature and stir overnight. The reaction mixture was filtered and the resulting solid washed with THF and $CH_2Cl_2$ to give a white solid (700 mg). The solid was stirred with EtOH (15 mL), filtered and the solid was rinsed with EtOH to give 476 mg of K-5 as a white solid. 1H NMR.

(E)-3-{1-Methyl-3-[(naphthalene-2-carbonyl)-amino]-1H-indazol-4-yl}-acrylic acid methyl ester (K-6). To a 50 mL pressure vessel was added K-5 (200 mg, 0.468 mmol), palladium acetate (10.5 mg, 0.047 mmol), tri-o-tolylphosphine (43 mg, 0.14 mmol) and $Et_3N$ (10 mL). The reaction mixture was degassed by bubbling $N_2$ gas through it (30 min). Methyl acrylate (1 mL, 36 mmol) was added and the degassing was continued for an additional 5 min. The vessel was sealed, heated at 75° C. for 30 min and then heated at 100° C. for 6 h. The reaction mixture was allowed to cool to room temperature overnight. The reaction mixture was degassed and additional palladium acetate (est. 0.1 eq) was added along with anhydrous DMF (20 mL). This solution was further degassed, the vessel was sealed and the reaction mixture was heated to 100° C. for 6 h and then allowed to cool to room temperature overnight. The reaction mixture was diluted with EtOAc and washed with water. The water wash was extracted once with EtOAc and the combined EtOAc extracts were diluted further with EtOAc, washed with water (3×), brine and dried ($Na_2SO_4$). The mixture was filtered and concentrated to give a quantitative yield of K-6 which was deemed pure enough to be carried on to the next reaction in the sequence. 1H NMR.

(E)-3-{1-Methyl-3-[(naphthalene-2-carbonyl)-amino]-1H-indazol-4-yl}-acrylic acid (A26). To a 25 mL round-bottomed, one-necked flask equipped with a magnetic stir bar was added K-6 (210 mg, 0.545 mmol) and a mixture of THF and methanol (10 mL, 1:1). To this stirring slurry was added 2M aqueous NaOH (0.85 mL, 1.7 mmol) in one portion and the reaction was stirred at room temperature. After 4 h at room temperature an additional amount of 2M NaOH (0.54 mL, 1.09 mmol) was added and the reaction mixture was placed in an oil bath at 40° C. and stirred overnight. The cooled reaction mixture was quenched through the addition of 1N HCl and the mixture was extracted with EtOAc (3×). The combined organic extracts were washed with brine, dried ($Na_2SO_4$), filtered and concentrated to give a yellow solid. This material was purified via flash chromatography utilizing first $CH_2Cl_2$/THF/hexanes (2:2:1) and then $CH_2Cl_2$/THF/MeOH (6:6:1) as eluent to give 95 mg of A26. 1H NMR (400 MHz, DMSO-d6) 4.07 (s, 3H), 6.54 (d, J=16.0 Hz, 1H), 7.48 (dd, J=8.0, 7.6 Hz, 1H), 7.60-7.70 (m, 3H), 7.75 (d, J=8.4 Hz, 1H), 8.00-8.05 (m, 3H), 8.11 (d, J=6.8 Hz, 1H), 8.25 (d, J=16.0 Hz, 1H), 8.65 (s, 1H), 10.77 (s, 1H), 12.23 (br s, 1H), MS (ESI+) Calcd for 371.40; Found 372.5 (M+1).

EXAMPLE 3

Preparation of A02

Synthesis of 5-Amino-1-(2,2-diethoxy-ethyl)-1H-pyrazole-4-carboxylic acid ethyl ester, K-7. To a solution of hydrazine hydrate (17.5 mL, 0.355 moles) in 60 mL absolute ethanol stirred at reflux temperature was added bromoacetaldehyde diethylacetal (20 g, 0.101 moles) dropwise and the resulting mixture was heated at refluxed overnight. The cooled reaction mixture was concentrated in vacuo and aqueous 35% NaOH containing 3 g NaCl (25 mL) was added and this solution was extracted with ether (2×100 mL). Combined organics were dried over $MgSO_4$ and concentrated in vacuo to afford 12.3 g of an oil . To a solution of this crude (2,2-diethoxy-ethyl)-hydrazine (12.3 g, 0.0831 moles) in 25 mL absolute ethanol was added a solution of ethyl ethoxymethylene cyanoacetate (14 g, 0.0831 moles) in 75 mL absolute ethanol. The mixture was stirred at room temperature for 3 days. Solvent was removed and oily crude residue K-7 was used without further purification. 1H NMR.

Synthesis of 1H-Imidazo[1,2-b]pyrazole-7-carboxylic acid ethyl ester, K-8. To a solution of crude K-7 (2 g) in absolute ethanol (10 mL) was added aqueous 20% sulfuric acid solution (12 mL) and the resulting mixture was refluxed for 1 h. The cooled reaction mixture was concentrated to remove the solvent and the mixture was poured to ice and adjusted to pH 8 with sodium bicarbonate. The insoluble material was filtered off and filtrate was extracted with methylene chloride (2×60 mL). The combined organic extracts were dried ($MgSO_4$), filtered and concentrated to give 1.2 g of a dark brown residue. This residue was purified by column chromatography using $CH_2Cl_2$ to 2% MeOH/$CH_2Cl_2$ to afford 280 mg of product K-8. 1H NMR.

Synthesis of 1-Naphthalen-2-ylmethyl-1H-imidazo[1,2-b]pyrazole-7-carboxylic acid ethyl ester, K-9. To a suspension of NaH (60% in mineral oil, 65 mg, 1.6 mmol) in DMF (5 mL), at 0° C. was added compound K-8 (240 mg, 1.34 mmol). The reaction mixture was stirred at 0° C. for 0.5 h, then at room temperature for 2 h. The reaction mixture was cooled to 0° C. and the 2-bromomethylnaphthalene was added. The mixture was stirred at room temperature overnight. The reaction was quenched through the addition of saturated $NH_4Cl$ (10 mL) and extracted with $CH_2Cl_2$ (2×50 mL). The combined organic extracts were washed with brine and dried ($MgSO_4$), filtered and concentrated to give 300 mg of a residue. This residue was purified by column chromatography using 5%-20% ethyl acetate/hexane to afford 208 mg of compound K-9. 1H NMR.

Synthesis of (1-Naphthalen-2-ylmethyl-1H-imidazo[1,2-b]pyrazol-7-yl)-methanol, K-10. To a stirred solution of compound K-9 (100 mg, 0.313 mmol) in 5 mL anhydrous methylene chloride, cooled to –70° C., was added DIBAL (1M solution in $CH_2Cl_2$, 0.94 mL, 3 eq.) dropwise. The reaction mixture was stirred at this temperature for 4 hours. The reaction mixture was quenched with MeOH, then a 50% saturated solution of sodium potassium tartrate was added and the mixture was allowed to warm to room temperature. The mixture was extracted with $CH_2Cl_2$ (2×20 mL). The combined organic extracts were washed with brine, dried ($MgSO_4$) filtered and concentrated to give 70 mg crude alcohol K-10. This material was used without further purification.

Synthesis of 1-Naphthalen-2-ylmethyl-1H-imidazo[1,2-b]pyrazole-7-carbaldehyde, K-11. Activated $MnO_2$ (110 mg, 1.26 mmol) was added to a suspension of alcohol (70 mg, 0.25 mmol) in anhydrous methylene chloride (10 mL). The reaction mixture was stirred at room temperature for two days. The reaction mixture was purified by column chromatography using $CH_2Cl_2$ to 5% $MeOH/CH_2Cl_2$ to afford 70 mg of compound K-11.

Synthesis of (E)-3-(1-Naphthalen-2-ylmethyl-1H-imidazo[1,2-b]pyrazol-7-yl)-acrylic acid ethyl ester, K-12. To a suspension of NaH (60% in mineral oil, 21 mg, 0.525 mmol) in anhydrous THF (3 mL), at 0° C. was added triethylphosphonoacetate (92 μl, 0.462 mmol). The reaction mixture was warmed up to room temperature and stirred for 1 h. The mixture was recooled to 0° C. and a solution of compound K-11 (60 mg, 0.21 mmol) in anhydrous THF (2 mL) was added. The mixture was allowed to warm up to room temperature and stirred for 1 h, then heated up 70° C. and stirred at this temperature overnight. The cooled reaction mixture was concentrated, $CH_2Cl_2$ (10 mL) was added and mixture was quenched with saturated aqueous $NH_4Cl$ (1 mL). The organic layer was washed with brine and dried ($MgSO_4$). The mixture was filtered and concentrated to afford 70 mg of compound K-12. This was used without further purification. 1H NMR.

Synthesis of (E)-3-(1-Naphthalen-2-ylmethyl-1H-imidazo[1,2-b]pyrazol-7-yl)-acrylic acid, A02. To a solution of compound K-12 (70 mg, 0.2 mmol) in MeOH/THF (2:1, 3 mL) was added aqueous 1N NaOH (1 mL). The reaction mixture was stirred at rt for 3 days. The reaction mixture was concentrated, aqueous 10% HCl (1 mL) was added to the residue and mixture was extracted with ethyl acetate (3×10 mL). The combined organic extracts were washed with brine, dried ($MgSO_4$), filtered and concentrated to give a residue (50 mg). This residue was purified via silica gel chromatography to give compound A02 (25 mg). $^1$H NMR (500 MHz, $CDCl_3$) 5.42 (s, 2H), 5.98 (d, J=15.5 Hz, 1H), 6.79 (s, 1H), 7.32 (dd, J=8, 2 Hz, 1H), 7.36 (d, J=2 Hz, 1H), 7.49-7.51 (m, 2H), 7.73 (bs, 1H), 7.76 (d, J=15.5 Hz, 1H), 7.83-7.87 (m, 2H), 7.94 (s, 1H).

LC-MS (90%): ESI+ Calcd. 317 m/z Found: 318.

EXAMPLE 4

Preparation of A23

Synthesis of 5-Bromo-4-oxo-pentanoic acid ethyl ester, K-13. Bromine (22 g, 7.2 mL, 138.8 mmol) was added to a solution of ethyllevulinate (20 g, 138.8 mmol) in 250 mL EtOH at room temperature under a flow of $N_2$ for a period of 0.5 h. After the addition was complete, the reaction mixture was stirred at room temperature for another 0.5 h, and then refluxed for 1.5 h. The reaction mixture was cooled to room temperature and concentrated in vacuo. The residue was taken into ether, washed with saturated aqueous $NaHCO_3$ (3×50 mL), water, brine, dried ($MgSO_4$) and concentrated to give 20.3 g of K-13 as a dark brown oil. This was used without purification for next step. 1H NMR.

Synthesis of Ethyl 2-amino-4-thiazolyl-3-propionate, K-14. A solution of crude bromide K-13 (8 g, 35.8 mmol) in ethanol (50 mL) was added to a solution of thiourea (2.85 g, 37.59 mmol) in ethanol (20 mL). The reaction mixture was stirred at room temperature for 1 h, and then refluxed for 4 h. The reaction mixture was concentrated and the residue was dissolved in ethyl acetate (100 mL), washed with water, saturated aqueous $NaHCO_3$, brine, dried ($MgSO_4$), filtered and concentrated to give the oily residue. This residue was purified by column chromatography using methylene chloride to 5% MeOH/methylene chloride to afford 3.75 g of product K-14. 1H NMR, MS.

Synthesis of 3-Imidazo[2,1-b]thiazol-3-yl-propionic acid ethyl ester, K-15. Bromoacetaldehyde diethylacetal (8 g, 40.31 mmol) in aqueous 3N HCl (60 mL) was heated to reflux for 1 h. The solution was cooled to room temperature and extracted with ether (3×30 mL). The combined organic extracts were dried ($MgSO_4$), filtered and then added dropwise to a refluxing solution of 3.75 g ethyl 2-amino-4 thiazolyl-3-propionate, K-14, in EtOH (100 mL). The distilling ether was collected. After ether collection was finished, the reaction mixture was refluxed for 8 h. The solvent was removed and the residue was diluted with saturated aqueous $NaHCO_3$. The mixture was extracted with methylene chloride (3×50 mL). The combined organic extracts were washed with water, brine, dried ($MgSO_4$), filtered and concentrated to afford 3 g of a residue. This residue was purified via column chromatography on silica gel using 20% to 50% ethyl acetate/hexanes as eluent to give 1 g of K-15. 1H NMR.

3-(5-Formyl-imidazo[2,1-b]thiazol-3-yl)-propionic acid ethyl ester, K-16. The Vilsmeier reagent was prepared at 0° C.-5° C. by dropping $POCl_3$ (0.085 mL, 0.892 mmol) into a stirred solution of DMF (0.1 mL). The resulting mixture was stirred at 0° C. for 0.5 h, then imidazothiazole (100 mg, 0.446 mmol) in $CHCl_3$ (2 mL) was added dropwise. The reaction mixture was warmed to room temperature, stirred for 2 h, then heated to reflux for 24 h. The mixture was cooled to room temperature, quenched with water, stirred for 0.5 h, and then extracted with methylene chloride. The organic layer was dried ($MgSO_4$), filtered and concentrated to afford 30 mg of K-16. 1H NMR.

3-[5-((E)-2-Naphthalen-2-yl-vinyl)-imidazo[2,1-b]thiazol-3-yl]-propionic acid ethyl ester, K-17. To a suspension of NaH, (60% dispersion in mineral oil, 10 mg, 0.25 mmol) in anhydrous THF (3 mL), was added (2-naphthyl)methyl triphenylphosphonium bromide (80 mg, 0.158 mmol). The mixture was heated to 60° C. for 1 h, then aldehyde K-16 (40 mg, 0.158 mmol) in 2 mL THF was added. The reaction mixture was stirred at 60° C. overnight. The mixture was cooled to room temperature, quenched with saturated aqueous $NH_4Cl$ and extracted with methylene chloride. The organic layer was dried ($MgSO_4$), filtered and concentrated to give a residue that was purified by column chromatography with 20% to 50% ethyl acetate/hexanes to afford 30 mg of K-17. 1H NMR.

3-[5-((E)-2-Naphthalen-2-yl-vinyl)-imidazo[2,1-b]thiazol-3-yl]-propionic acid, A22. To a solution of ethyl ester, K-17 (30 mg, 0.079 mmol) in a mixture of THF: MeOH (3:1, 2 mL) was added aqueous 1N LiOH (0.16 mL). The mixture was stirred and heated at 40° C. for 2 h. The reaction mixture was concentrated in vacuo and to the resulting residue was added aqueous 10% HCl until a pH of 5-6 was reached. The mixture was extracted with methylene chloride (2×5 mL). The combined organic extracts were washed with brine, dried (MgSO4), and concentrated to give 20 mg of A23. $^1$H NMR (500 MHz, CDOD) 2.764-2.793 (t, J=7.5 Hz, 2H), 3.243-3.273 (t, J=7.5 Hz, 2H), 6.8 (s, 1H), 6.86 (d, J=12 Hz, 1H), 6.94 (d, J=12 Hz, 1H), 7.38-7.41 (dd, J=8.5, 1.5 Hz, 1H), 7.42-7.46 (m, 2H), 7.695 (d, J=9 Hz, 1H), 7.72-7.74 (m, 1H), 7.77 (s, 1H), 7.8-7.86 (m, 2H). LC-MS (90%, combined mixture of cis and trans): ESI– Calcd. 348 m/z Found: 347.

EXAMPLE 5

Prepatation of A47

1-Allyl-2-oxo-cyclohexane carboxylic acid ethyl ester, K-18: To a 1 L round-bottom flask equipped with a condenser, magnetic stir bar and under a nitrogen atmosphere was added 2-oxo-cyclohexane carboxylic acid ethyl ester (19.0 g, 112 mmol), allyl bromide (14.2 g, 117 mmol), THF (223 mL) and potassium tert-butoxide (13.2 g, 117 mmol). The mixture was brought to reflux in an oil bath (67° C.) and heated for 18 h. The solvent was removed from the cooled reaction mixture via rotary evaporation and 1M HCl was added until the mixture turned from a paste to a cloudy solution. The mixture was extracted with methylene chloride (3×250 mL). The combined organic extracts were washed with water (2×250 mL), brine (250 mL), dried (MgSO$_4$), filtered and concentrated under reduced pressure to produce 21.8 g (93%) of K-18 as a pale yellow oil. $^1$H NMR analysis indicated the material was pure enough to carry on to the next step. $^1$H NMR.

1-Carboxymethyl-2-oxo-cyclohexane carboxylic acid ethyl ester, K-19: To a 2 L, three-neck round-bottom flask equipped with an overhead stirrer and two loose caps was placed compound K-18 (21.8g, 104 mmol). In a 1 L Erlenmeyer flask equipped with a stir bar was added sodium periodate (182 g, 850 mmol), potassium permanganate (3.28 g, 20.7 mmol), potassium carbonate (10.9 g, 78.8 mmol) and water (430 mL) at room temperature. The oxidizing mixture was stirred for 5 minutes and then added to the flask containing K-18 in one portion. The mixture was allowed to stir at room temperature for a period of 24 h. After this reaction period, additional potassium permanganate (0.820 g, 5.19 mmol) was added to the reaction mixture. The contents of the flask were stirred for an additional 2.5 h. The reaction was quenched by the slow addition of aqueous sodium hydrogen sulfite, upon which an extreme exotherm was observed, until the mixture turned from a dark brown mixture to clear yellow solution. The aqueous mixture was extracted with methylene chloride (3×250 mL). The combined extracts were washed with water (2×250 mL) and brine (250 mL), dried (MgSO$_4$), filtered and concentrated under reduced pressure to produce 18.6 g (79%) of K-19 as a pale yellow oil. $^1$H NMR analysis indicated the material was pure enough to carry on to the next step. $^1$H NMR.

1-(2,4-Dichloro-benzyl)-2-oxo-1,2,3,4,5,6-hexahydro-indole-3a-carboxylic acid ethyl ester, K-20: To a 250 mL round-bottom flask equipped with a condenser and stir bar was placed compound K-19 (5.00 g, 21.9 mmol), m-xylene (45 mL) and 2,4-dichlorobenzylamine (2.95 mL, 21.9 mmol). The mixture was brought to reflux in an oil bath (138° C.) and heated for 6 hours. The reaction was then cooled to room temperature and reacted for an additional 18 h. The solvent was removed by evaporation to yield 7.92 g (98%) of compound K-20 as reddish-orange oil. $^1$H NMR analysis indicated the material was pure enough to carry on to the next step. $^1$H NMR 7-Bromo-1-(2,4-dichloro-benzyl)-2-oxo-1,2,3,4,5,6-hexahydro-indole-3a-carboxylic acid ethyl ester, K-21: To a 40 mL vial equipped with a stir bar and cap was placed compound K-20 (600 mg, 1.63 mmol) which was dissolved in methylene chloride (16 mL). The solution was cooled to 0° C. in an ice bath and bromine (416 µL, 8.15 mmol) was added. The mixture was stirred for 2 h while gradually warming to room temperature and then triethylamine (750 µL, 5.38 mmol) was added. The mixture was allowed to stir an additional 45 minutes and then the reaction was quenched with water (15 mL). After stirring for 30 minutes, the organic portion was extracted and then dried with MgSO$_4$. The mixture was filtered and the solvent was removed by evaporation to yield a brown oil which was purified by silica gel column chromatography utilizing 20 % EtOAc/hexanes as eluent. After purification, 431 mg of compound K-21 was isolated as a tan solid (59%). $^1$H NMR analysis indicated the material was pure enough to carry on to the next step. $^1$H NMR.

7-((E)-2-Carboxy-vinyl)-1-(2,4-dichloro-benzyl)-2-oxo-1,2,3,4,5,6-hexahydro-indole-3a-carboxylic acid ethyl ester, A47. To an 18 mL vial equipped with a stir bar and cap was placed compound K-21 (431 mg, 0.964 mmol), anhydrous DMF (4.8 mL) and triethylamine (1.34 mL, 9.64 mmol). The mixture was stirred while being degassed with nitrogen for 10 minutes. After degassing, tert-butyl acrylate (423 µL, 2.89 mmol), palladium acetate (21.6 mg, 0.0964 mmol) and tri-(o-tolyl)phosphine (88.0 mg, 0.289 mmol) were added. After these additions, the mixture was degassed with nitrogen for an additional 3 minutes and then the vial was sealed with a cap. The vial was heated in an oil bath to 100° C. for a period of 22 h. The reaction was then cooled and filtered through celite. The mixture was diluted with methylene chloride (75 mL) and then washed with water (2×75 mL) and brine (75 mL). The organic portion was dried (MgSO$_4$), filtered and concentrated under reduced pressure to produce the t-butyl ester product as a brown oil. The crude material was dissolved in methylene chloride (4.4 mL) and cooled to 0° C. To this solution was added trifluoroacetic acid (440 µL, 5.9 eq) and the mixture was allowed to stir at room temperature for 4.5 h. Additional trifluoroacetic acid (440 µL, 5.9 eq) was introduced and the mixture was stirred for 20 min. The solvent was removed by a stream of nitrogen and the material was dissolved in ether and washed with saturated aqueous NaHCO$_3$ (4×30 mL). During the second washing with NaHCO$_3$, a small portion of 3M NaOH (20 mL) was added in order to better separate the layers. The aqueous layers were combined and acidified to pH 1 with aqueous 3M HCl. The aqueous layer was extracted with methylene chloride (3×100 mL). The organic extracts were combined, dried (MgSO$_4$), filtered and concentrated via rotary evaporation to yield 182 mg of A47 as a pale yellow solid (43% yield from K-21 to A47). $^1$H NMR (400 MHz, CDCl$_3$) 1.28 (t, J=7.2 Hz, 3H), 1.56-1.70 (m, 2H), 1.90-1.98 (m, 1H), 2.24-2.39 (m, 2H), 2.55-2.58 (m, 1H), 2.79 (AB q, J=17.2, 16.8 Hz, 2H), 4.21 (q, J=7.2 Hz, 2H), 5.01 (AB q, J=17.6, 11.6 Hz, 2H), 5.68 (d, J=15.2 Hz, 1H), 7.13 (d, J=8.0 Hz, 1H), 7.21 (dd, J=2.0, 8.4 Hz, 1H), 7.38 (d, J=15.6 Hz, 1H), 7.44 (d, J=2.0 Hz, 1H). LC/MS (86%), MS (ESI-) Calcd.: 437.3 m/z, Found: 436.4 m/z

EXAMPLE 6

Preparation of A17

Synthesis of 7-Bromo-1H-indole-2,3-dione, K-22. To a 500 mL round-bottomed flask which contained a stirring solution chloral hydrate (12 g, 66 mmol) in water (150 mL) was added Na$_2$SO$_4$ (14 g, 100 mmol) and a suspension of 2-bromoaniline (9 g, 50 mmol) in 2N aqueous HCl (60 mL) at room temperature. The resulting reaction mixture was heated to reflux for 30 min. then cooled to room temperature. The solid which formed was filtered, washed with water (3×100 mL) and dried over vacuum at 50° C. to provide crude N-(2-bromo-phenyl)-2-hydroxyimino-acetamide (9 g) which was directly used for next step without further purification. To a 500 mL round-bottomed flask which contained a pre-heated (to 50° C.) stirring solution of concentrated H$_2$SO$_4$ (80 mL) was added the intermediate N-(2-bromo-phenyl)-2-hydroxy-imino-acetamide portionwise at 50° C. The resulting reaction mixture was heated to 80° C. and stirred at 80° C. for 30 min., then cooled to room temperature and poured into 600 mL of stirring ice-water. The solid which formed was filtered, washed with water (3×100 mL) and dried under vacuum at 50° C. to yield the desired K-22 (5.2 g, 44% for two steps) MS (ESI$^+$): 227 (M+1). $^1$H-NMR.

Synthesis of K-23. To a 500 mL round-bottomed flask which contained a solution of 7-bromo-indole-2,3-dione K-22 (5 g, 22 mmol) and p-toluenesulphonic acid monohydrate (500 mg, 10 mol. %) in dry benzene (200 mL) was added ethyleneglycol (5 g, 82 mmol, 3.8 eq.). The resulting reaction mixture was heated to reflux for 23 h using a Dean-Stark trap to remove the generated water. The reaction mixture was allowed to cool to room temperature, washed with 10% aqueous NaHCO$_3$ (100 mL) and then water (100 mL). Concentration of the organic layer afforded 6 g of a residue which was purified by recrystallization with CH$_2$Cl$_2$/ethyl acetate/hexanes to afford K-23 (5.4 g, 90% yield) as an off-white solid. MS (ESI$^+$): 270 (M+1). $^1$H-NMR.

Synthesis of K-24. To a tube containing a solution of K-23 (5.4 g, 20 mmol), tri-o-tolylphosphine (2.2, 7 mmol, 0.3 eq.) and palladium acetate (500 mg, 2 mmol, 0.1 eq.) in triethylamine (20 mL) was added methyl acrylate (5 g, 70 mmol, 3.5 eq) at room temperature. The tube was sealed and the reaction mixture was heated and stirred at 100° C. for 6 h, then cooled to room temperature, poured into 600 mL stirring ice-water solution and extracted with CH$_2$Cl$_2$ (3×100 mL). The combined organic extracts were washed with water (2×100 mL), brine (100 mL) and dried (Na$_2$SO$_4$). After filtration and removal of the solvent, 6 g of a residue was obtained which was purified by the combination of recrystallization with CH$_2$Cl$_2$/ethyl acetate/hexanes and flash chromatography (silica gel, CH$_2$Cl$_2$; CH$_2$Cl$_2$/EtOAc/hexane, v/v/v=1:10:20-1:20:10; EtOAc) to yield K-24 (total 4.5 g, 81%) as an off-white solid. MS (APCI$^-$): 274 (M−1). $^1$H-NMR.

Synthesis of K-25. To a 250 mL round-bottomed flask containing a stirring suspension of K-24 (3 g, 11 mmol) and K$_2$CO$_3$ (10 g, 55 mmol, 5 eq) in DMF (40 mL) was added 2,4-dichlorobenzyl chloride (2.4 g, 12 mmol, 1.05 eq). The resulting reaction mixture was heated to 50° C. for 3 h and then stirred at room temperature overnight. The mixture was poured into 600 mL of stirring ice-water. The resulting solid that formed solid was filtered, washed with water (3=100 mL) and dried over vacuum at 50° C. to provide the K-25 (2.8 g) as off-white solid. An additional quantity of K-25 (1 g) was obtained from the filtrate after extraction with ethyl acetate (2×100 mL) and subsequent purification of the resulting residue by flash chromatography (silica gel, CH$_2$Cl$_2$; CH$_2$Cl$_2$/EtOAc/hexane, v/v/v=1:10:20-1:20:10; EtOAc). Total amount of K-25 produced was 3.8 g, (80%). MS (APCI$^+$): 434.3 (M), 436.3 (M+2). $^1$H-NMR.

Synthesis of (E)-3-[1-(2,4-Dichloro-benzyl)-2,3-dioxo-2,3-dihydro-1H-indol-7-yl]-acrylic acid methyl ester, K-26. To a stirring suspension of K-25 (2.1 g, 5 mmol) in MeOH (50 mL) was added concentrated HCl (50 mL) at room temperature. The resulting reaction mixture was heated to 90° C. for 3 h, cooled to room temperature and poured into 200 mL of stirring ice-water. The solid formed was filtered, washed with water (3×100 mL) and dried under vacuum at 50° C. to provide 1.7 g (83%) of K-26 as an orange color solid. MS (APCI$^+$): 390.3 (M), 392.2 (M+2). $^1$H-NMR.

Synthesis of (E)-3-[1-(2,4-Dichloro-benzyl)-2,3-dioxo-2,3-dihydro-1H-indol-7-yl]-acrylic acid, A17. To a 500 mL round bottom flask containing a solution of NaOH (1 g, 25 mmol) in MeOH (50 mL) and H$_2$O (50 mL) was added K-26 (1.6 g, 15 mmol) at 5° C. The resulting reaction mixture was allowed to warm to room temperature and stir for 10 min, then heated to 50° C. for 4 h. The reaction mixture was cooled to 5° C. and was acidified through the addition of 10% aqueous HCl until a pH of 1 was reached and then the mixture was diluted with water (250 mL). The resulting solid was filtered, washed with water (3×100 mL) and dried under vacuum at 50° C. to provide A17 (1.34 g, 85%) as orange color solid. 1H NMR (500 MHz, DMSO-d6) 5.17 (s, 2H), 6.27 (d, J=15.5 Hz, 1H), c 7.33 (dd, J=8.5 Hz, J=1.5 Hz, 1H), 7.45 (d, J=16.0 Hz, 1H), 7.55-7.57 (m, 1H), 7.71 (dd, J=7.5 Hz, J=1.5 Hz, 1H), 7.82 ((d, J=8.5 Hz, 1H)).

LC/MS (90%) ESI− Calcd: 376.2; Found: 374.1 (M−2).

EXAMPLE 7

Preparation of A21

Synthesis of 2,4-Dichloro-benzoic acid 2-amino-3-nitrophenyl ester, K-27. To a 500 mL, round-bottomed, one-necked flask equipped with a magnetic stir bar and a septum was added 2-amino-3-nitrophenol (4.25 g, 27.6 mmol), anhydrous CH$_2$Cl$_2$ (140 mL), 4-(dimethylamino)pyridine (3.37 g, 27.6 mmol) and 2,4-dichlorobenzoyl chloride (5.78 g, 3.87 mL, 27.6 mmol). The reaction mixture was allowed to stir at room temperature overnight. The reaction mixture was diluted with CH$_2$Cl$_2$ (300 mL) and the mixture was washed with H$_2$O (2×200 mL), dried (Na2SO$_4$), and concentrated to give 8.91 g (98.7%) of a yellow-orange solid. $^1$H NMR analysis indicated the material K-27 was pure enough to carry on to the next step. $^1$H NMR Synthesis of 2,4-Dichloro-N-(2-hydroxy-6-nitro-phenyl)-benzamide, K-28. To a 500 mL, round-bottomed, one-necked flask containing K-27 (8.91 g, 27.2 mmol) was added a magnetic stir bar and anhydrous THF (300 mL) and the reaction vessel was placed under a N$_2$ atmosphere. Sodium hydride (1.08 g, 44.9 mmol, 60% in oil dispersion) was added in portions cautiously to the stirring reaction mixture over a period of 2 min. After an additional 2 min, H$_2$ gas evolution occurs (fairly rapidly) and a slight exotherm was observed. The mixture was stirred at room temperature for 1 h. The mixture was allowed to stir at room temperature overnight. The mixture was cautiously quenched through the slow addition of water (50 mL) dropwise and then in small portions. The mixture was poured into EtOAc (1 L) and water (200 mL). The aqueous layer was acidified to a pH ~1 with 1N HCl and extracted. The layers were separated and the aqueous layer extracted with EtOAc (100 mL). The combined organic extracts were dried (Na$_2$SO$_4$), filtered and concentrated to give K-28, (9.36 g) as a tan solid. 1H NMR Synthesis of N-(2-Amino-6-hydroxy-phenyl)-2,4-dichloro-benzamide K-29. To a 250 mL hydrogenation vessel was added an aqueous slurry of Raney nickel (700 mg) and it was cautiously diluted with EtOH (60 mL). Compound K-28 (700 mg, 2.14 mmol) was added as a solid. The sides of the vessel were rinsed with EtOH (10 mL) and the mixture was subjected to hydrogenation in a Parr shaker at 50 psi of H$_2$ gas at room temperature overnight. The reaction mixture was filtered through a pad of Celite and the pad was rinsed with EtOH (400 mL). The filtrate was concentrated to give a quantitative yield of a dark brown solid, K-29. 1H NMR.

Synthesis of 3-Amino-2-(2,4-dichloro-benzylamino)-phenol, K-30. To a 250 mL round bottomed, one-necked flask equipped with a magnetic stir bar, a reflux condenser and placed under a N$_2$ atmosphere was added compound K-29 (635 mg, 2.14 mmol). Anhydrous THF (31 mL) was added followed by drop wise addition of 1M BH$_3$ in THF (8.6 mL, 8.6 mmol). The reaction mixture was heated at reflux overnight. The cooled reaction mixture was cautiously quenched through the drop wise addition of methanol (50 mL). The resulting mixture was concentrated on a rotary evaporator. The residue was again dissolved in methanol (50 mL) and reconcentrated. This redissolution of the residue in methanol and reconcentration was repeated two more times to give a quantitative yield of a brown oil, K-30. 1H NMR.

Synthesis of 3-(2,4-Dichloro-benzyl)-3H-benzoimidazol-4-ol, K-31. To a 20 mL vial containing a magnetic stir bar was added compound K-30 (980 mg, 3.46 mmol) and absolute EtOH (8 mL). To this stirring suspension was added triethyl orthoformate (0.634 mL, 3.81 mmol) and p-toluenesulfonic acid monohydrate (33 mg, 0.173 mmol). The vial was capped and placed in an oil bath at 75° C. for 1 h. At this time the cap was removed from the vial and the oil bath temperature was increased to 95-100° C., boiling off the solvent. The last traces of solvent were removed under high vacuum. The residue was triturated twice with 1:1 hexanes/acetone (6 mL each time) and resulting dark brown solid was filtered and dried to give K-31, 570 mg (56%). 1H NMR.

Synthesis of [3-(2,4-Dichloro-benzyl)-3H-benzoimidazol-4-yloxy]-acetic acid methyl ester, K-32. To a 5 mL vial containing a magnetic stir bar and compound K-31 (60 mg, 0.204 mmol) was added anhydrous DMF (0.8 mL), anhydrous potassium carbonate (34 mg, 0.246 mmol) and methyl bromoacetate (24 μL, 0.246 mmol). The reaction mixture was stirred at room temperature overnight. The reaction mixture was concentrated to give a residue which was dissolved in 1:1 hexanes/acetone (1 mL) and was purified by column chromatography on flash silica gel (6 g) utilizing 4:1 hexanes/acetone followed by 7:3 hexanes/acetone as eluent to give K-32, 40 mg (54%) of a semisolid. 1H NMR.

Synthesis of [3-(2,4-Dichloro-benzyl)-3H-benzoimidazol-4-yloxy]-acetic acid, A21. To a 50 mL round bottomed, one-necked flask containing compound K-32 (32 mg, 0.088 mmol) was added absolute ethanol (0.5 mL), water (0.5 mL) and 15% aqueous sodium hydroxide (0.025 mL, 0.093 mmol). The reaction mixture was allowed to stir at room temperature overnight. The mixture was concentrated to give a solid. The solid was dissolved in water (3 mL) and made acidic through the addition of aqueous 1 N HCl (0.25 mL). pH of the solution was 2-3 by litmus paper. The resulting precipitate was filtered and dried. The aqueous filtrate was extracted with EtOAc (3×1 mL) and the organic extracts were concentrated to give a solid. This solid was combined with the isolated precipitate to give 28 mg (91%) of A21 as an off-white solid. 1H NMR (500 MHz, DMSO-d6) 4.69 (s, 2H), 5.80 (s, 2H), 6.70 (d, J=8.0 Hz, 1H), 6.77 (d, J=8.0 Hz, 1H), 7.14 (dd, J=8.0, 8.0 Hz, 1H), 7.31 apparent d, J=8.0 Hz, 2H) 7.66 (d, J=2.0 Hz, 1H), 8.32 (s, 1H), 12.98 (br, s 1H). LC/MS (96%), (ESI/−) Calcd. for 350.02; Found: 349.2 (M−1).

EXAMPLE 8

Preparation of A22

Synthesis of Naphthalene-2-carboxylic acid 2-amino-3-nitro-phenyl ester, K-33. Compound K-33 was synthesized from 2-amino-3-nitrophenol (99%) in a manner analogous to that of the synthesis of compound K-27. $^1$H NMR Synthesis of Naphthalene-2-carboxylic acid (2-hydroxy-6-nitro-phenyl)-amide, K-34. Compound K-34 was synthesized from compound K-33 (quantitative yield) in a manner analogous to that of the synthesis of compound K-28 from compound K-27. $^1$H NMR.

Synthesis of Naphthalene-2-carboxylic acid (2-amino-6-hydroxy-phenyl)-amide, K-35. To a 50 mL round-bottomed, one-necked flask equipped with a magnetic stir bar, a condenser and a N$_2$ inlet/outlet adapter was added compound K-34 (100.7 mg, 0.327 mmol) and absolute ethanol (5 mL). The reaction mixture was placed in an oil bath at 70° C. and under a N$_2$ atmosphere. Tin(II) chloride dihydrate (738 mg, 3.27 mmol) was added followed by the dropwise addition of 6 N HCl (2.18 mL, 13.1 mmol). After heating at 70° C. for 1 h the reaction mixture was cooled to room temperature, diluted with water and EtOAc (50 mL each) and made basic (pH ~8) through the cautious addition of saturated aqueous NaHCO$_3$. The solution was filtered to remove the precipitated tin salts and the organic layer was separated, dried (Na$_2$SO$_4$), filtered and concentrated to give K-35, 81 mg (89%). 1H NMR, MS; AP-277.0.

Synthesis of 3-Amino-2-[(naphthalen-2-ylmethyl)-amino]-phenol, K-36. Compound K-36 was synthesized from compound K-35 (quantitative yield) in a manner analogous to that of the synthesis of compound K-30 from compound K-29. $^1$H NMR.

Synthesis of 3-Naphthalen-2-ylmethyl-3H-benzoimidazol-4-ol, K-37. Compound K-37 was synthesized from compound K-36 (35%) in a manner analogous to that of the synthesis of compound K-31 from compound K-30. $^1$H NMR.

Synthesis of (3-Naphthalen-2-ylmethyl-3H-benzoimidazol-4-yloxy)-acetic acid methyl ester, K-38. Compound K-38 was synthesized from compound K-37 (55%) in a manner analogous to that of the synthesis of compound K-32 from compound K-31. $^1$H NMR.

Synthesis of (3-Naphthalen-2-ylmethyl-3H-benzoimidazol-4-yloxy)-acetic acid, A22. Compound A22 was synthesized from compound K-38 (55%) in a manner analogous to that of the synthesis of compound A21 from compound K-32. 1H NMR (500 MHz, DMSO=d6) 4.91 (s, 2H), 5.96 (s, 2H), 6.96 (d, J=8.0 Hz, 1H), 7.31 (dd, J=8.0, 8.0 Hz, 1H), 7.36 (d, J=8.0 Hz, 1H), 7.51 (m, 3H), 7.58 (dd, J=8.0, 2.0 Hz, 1H), 7.85-7.90 (m, 3H), 7.99 (s, 1H), 9.20 (s, 1H), 13.21 (br s, 1H). LC/MS (95.7%) (ESI/−) Calcd. for 332.12; Found: 331.1 (M−1).

EXAMPLE 9

Preparation of A24

General synthesis of hexahydro oxyindole derivatives. Synthesis of 2-Methyl-2-allylcyclohexanone, K-39: To a solution of sodium hydride (1 eq.; 60% dispersion in mineral oil) in dimethoxyethylene glycol at 5° C. under nitrogen atmosphere, was added 2-methylcyclohexanone (1 eq.) dropwise. The solution was allowed to warm to room temperature, after which it was heated to 80° C. for 1.5 h. The solution was then cooled to room temperature, and then to 5° C. Allyl bromide (1 eq.) was added drop wise, after which, the reaction mixture was heated to 80° C. for 1.5 h. The reaction was cooled to room temperature and water (~14 eq.) was added dropwise. The aqueous layer was extracted twice with ethyl ether, and dried over sodium sulfate. After concentration, the crude product was purified via silica gel chromatography using 2.5% ethyl ether in hexanes to obtain compound K-39 in 35% yield. $^1$H NMR Synthesis of (1-Methyl-2-oxo-cyclohexyl)-acetic acid, K-40. To biphasic solution of 1-methyl-1-allylcyclohexanone, K-39, in H$_2$O/CH$_3$CN/CCl$_4$ under nitrogen atmosphere was added NaIO4 (20 eq), followed by RuCl$_3$.H$_2$O. The reaction was stirred at room temperature overnight.

2-Propanol (~88 eq) was added dropwise, causing the reaction mixture to blacken. The mixture was diluted with water and ethyl ether, filtered through a Celite pad, and the pad was washed with ethyl ether. The aqueous layer was extracted with dichloromethane and ethyl acetate. The combined organics extracts were dried over sodium sulfate, and concentrated in vacuo to give compound K-40 in quantitative yield. $^1$H NMR.

General procedure (P-1) for preparation of hexahydro-indol-2-ones, K-41x: A solution of (1-Methyl-2-oxo-cyclohexyl)-acetic acid, K-40 (1 eq), and the appropriate benzyl amine (1 eq) in m-xylene was heated under reflux at 145° C. for 3 h. The reaction was concentrated in vacuo, and the residue either taken through crude, or purified via silica gel chromatography, using hexanes in dichloromethane (10-20%) as eluent to obtain the desired product, K-41x. Product structure was verified by $^1$H NMR.

General procedure (P-2) for bromination of hexahydro-indol-2-ones, K-42x: To a solution of the appropriate hexahydro-indol-2-one, K-41x in dichloromethane at 0° C. was added bromine (1 eq) dropwise. The reaction mixture was stirred until bromine color disappeared, and then for an additional 5 minutes. Triethylamine (3 eq) was added in one portion and the reaction mixture was stirred at room temperature for 10 minutes. The reaction was washed with water (3×), and dried over magnesium sulfate. The dichloromethane solution was filtered and concentrated in vacuo. The residue was either taken through to the next step crude, or purified via silica gel chromatography, using dichloromethane as the eluent, to obtain the appropriate allylic bromide, K-42x. Product structure was verified by $^1$H NMR.

General procedure (P-3) for Heck couplings of K-42x to provide acrylate ester K-43x: In a round bottom flask equipped with a reflux condenser, and nitrogen inlet/outlet, was placed a solution of the appropriate 7-bromo-hexahydro-indol-2-one and triethylamine (10 eq) in DMF. To the solution was added, in order, methyl acrylate (1.1 eq), palladium(II) acetate (0.1 eq), and tri-o-tolyl phosphine (0.3 eq). The reaction was heated at 100° C. for 16 h, and then allowed to cool to room temperature. The reaction mixture was filtered through Celite, and washed with dichloromethane, and then diluted with dichloromethane and water, and the layers separated. The organic extracts were washed with water (2×), brine, and dried over magnesium sulfate. The organic extracts were then filtered and concentrated in vacuo. The residue was either taken through crude, or purified via silica gel chromatography, using 15% hexanes in dichloromethane as eluent, to obtain acrylate ester K-43x. Product structure was verified by $^1$H NMR.

General procedure (P-4) for hydrolysis of methyl esters to provide the desired acrylic acid product. To a solution of the appropriate methyl ester, K-43x in THF/MeOH (2:1), was added aqueous NaOH (3 eq), and the reaction stirred for 24-72 h at room temperature. The mixture was washed with 2 portions of diethyl ether, diluted with ethyl acetate, and the pH adjusted to 2-3 with 1 N HCl. The organic layer was separated, washed with brine, dried over magnesium sulfate, and concentrated to obtain corresponding acids. Product structure was verified by $^1$H NMR.

Synthesis of 3a-Methyl-1-naphthalen-2-ylmethyl-1,3,3a,4,5,6-hexahydro-indol-2-one, K-41A: Following the general procedure P-1, (1-Methyl-2-oxo-cyclohexyl)-acetic acid (K-40) was converted to K-41A. Consistent with 1H-NMR.

Synthesis of 7-Bromo-3a-methyl-1-naphthalen-2-ylmethyl-1,3,3a,4,5,6-hexahydro-indol-2-one, K-42A: Following the general procedure P-2, 3a-Methyl-1-naphthalen-2-ylmethyl-1,3,3a,4,5,6-hexahydro-indol-2-one, K-41A was converted to K-42A. Consistent with 1H-NMR.

Synthesis of (E)-3-(3a-Methyl-1-naphthalen-2-ylmethyl-2-oxo-2,3,3a,4,5,6-hexahydro-1H-indol-7-yl)-acrylic acid methyl ester, K-43A: Following the general procedure P-3, 7-Bromo-3a-methyl-1-naphthalen-2-ylmethyl-1,3,3a,4,5,6-hexahydro-indol-2-one, K-42A was converted to K-43A. Consistent with 1H-NMR.

Synthesis of (E)-3-(3a-Methyl-1-naphthalen-2-ylmethyl-2-oxo-2,3,3a,4,5,6-hexahydro-1H-indol-7-yl)-acrylic acid, A24: Following the general procedure P-4, (E)-3-(3a-Methyl-1-naphthalen-2-ylmethyl-2-oxo-2,3,3a,4,5,6-hexahydro-1H-indol-7-yl)-acrylic acid methyl ester, K-43A was converted to A24.

1H-NMR (500 MHz, CDCl$_3$) 1.23 (s, 3H), 1.63 (ddd, 1H, J=14.8, 11.6,2.8 Hz), 1.74 (m, 1H), 1.83-1.89 (m, 2H), 2.24 (m, 1H), 2.38 (dd, 1H, J=7.2 Hz), 2.49 (s, 2H), 4.90 (d, 1H, J=16.0 Hz), 5.58 (d, 1H, J=16.0 Hz), 5.60 (d, 1H, J=15.2 Hz), 7.35 (dd, 1H, J=8.4, 1.6 Hz), 7.42-7.44 (m, 2H), 7.75-7.82 (m, 4H), 8.06 (d, 1H, J=15.2 Hz)

LC/MS (98%) ESI+ Calcd: 361.4; Found: 362.6 (M+1)

EXAMPLE 10

Preparation of A27

Synthesis of 1-(3-Fluoro-benzyl)-3a-methyl-1,3,3a,4,5,6-hexahydro-indol-2-one, K-41B: Following the general procedure P-1, (1-Methyl-2-oxo-cyclohexyl)-acetic acid (K-40), was converted to K-41B. Consistent with 1H-NMR.

Synthesis of 7-Bromo-1-(3-Fluoro-benzyl)-3a-methyl-1,3,3a,4,5,6-hexahydro-indol-2-one, K-42B: Following the general procedure P-2, 1-(3-Fluoro-benzyl)-3a-methyl-1,3,3a,4,5,6-hexahydro-indol-2-one, K-41B was converted to K-42B. Consistent with 1H-NMR.

Synthesis of (E)-3-[1-(3-Fluoro-benzyl)-3a-methyl-2-oxo-2,3,3a,4,5,6-hexahydro-1H-indol-7-yl]-acrylic acid methyl ester, K-43B: Following the general procedure P-3, 7-Bromo-1-(3-Fluoro-benzyl)-3a-methyl-1,3,3a,4,5,6-hexahydro-indol-2-one, K-42B was converted to K-43B. Consistent with 1H-NMR.

Synthesis of (E)-3-[1-(3-Fluoro-benzyl)-3a-methyl-2-oxo-2,3,3a,4,5,6-hexahydro-1H-indol-7-yl]-acrylic acid, A27: Following the general procedure P-4, (E)-3-[1-(3-Fluoro-benzyl)-3a-methyl-2-oxo-2,3,3a,4,5,6-hexahydro-1H-indol-7-yl]-acrylic acid methyl ester, K-43B was converted to A27. 1H-NMR (500 MHz, CDCl$_3$) 1.23 (s, 3H), 1.61 (ddd, 1H, J=16.4, 11.6, 4.8 Hz), 1.78 (m, 1H), 1.84-1.90 (m, 2H), 2.24-2.30 (m, 2H), 2.46 (s, 2H), 4.86 (d, 1H, J=16.4 Hz), 5.22 (d, 1H, J=16.4 Hz), 5.63 (d, 1H, J=15.2 Hz), 6.94-6.97 (m, 2H), 7.29 (ddd, 1H, J=6.0, 2.8, 1.6 Hz), 7.81 (d, 1H, J=15.2 Hz)

LC/MS (98%) ESI+ Calcd: 329.4; Found: 330.6 (M+1)

EXAMPLE 11

Preparation of A28

Synthesis of 1-(4-Fluoro-benzyl)-3a-methyl-1,3,3a,4,5,6-hexahydro-indol-2-one, K-41C: Following the general procedure P-1, (1-Methyl-2-oxo-cyclohexyl)-acetic acid (K-40) was converted to K-41C. Consistent with 1H-NMR.

Synthesis of 7-Bromo-1-(4-Fluoro-benzyl)-3a-methyl-1,3,3a,4,5,6-hexahydro-indol-2-one, K-42C: Following the general procedure P-2, 1-(4-Fluoro-benzyl)-3a-methyl-1,3,3a,4,5,6-hexahydro-indol-2-one, K-41C was converted to K-42C. Consistent with 1H-NMR.

Synthesis of (E)-3-[1-(4-Fluoro-benzyl)-3a-methyl-2-oxo-2,3,3a,4,5,6-hexahydro-1H-indol-7-yl]-acrylic acid methyl ester, K-43C: Following the general procedure P-3, 7-Bromo-1-(4-Fluoro-benzyl)-3a-methyl-1,3,3a,4,5,6-hexahydro-indol-2-one, K-42C was converted to K-43C. Consistent with 1H-NMR.

Synthesis of (E)-3-[1-(4-Fluoro-benzyl)-3a-methyl-2-oxo-2,3,3a,4,5,6-hexahydro-1H-indol-7-yl]-acrylic acid, A28: Following the general procedure P-4, (E)-3-[1-(4-Fluoro-benzyl)-3a-methyl-2-oxo-2,3,3a,4,5,6-hexahydro-1H-indol-7-yl]-acrylic acid methyl ester, K-43C was converted to A28. 1H-NMR (500 MHz, CDCl$_3$) 1.18 (s, 3H), 1.60 (ddd, 1H, J=13.2, 13.6, 8.4 Hz), 1.78 (m, 1H), 1.84-1.89 (m, 2H), 2.26-2.30 (m, 2H), 2.44 (s, 2H), 4.80 (d, 1H, J=16.0 Hz), 5.25 (d, 1H, J=16.0 Hz), 5.64 (d, 1H, J=15.6 Hz), 7.00 (ddd, 2H, J=8.4, 6.4, 2.0 Hz), 7.23 (ddd, 2H, J=8.4, 5.2, 2.0 Hz), 7.86 (d, 1H, J=15.2 Hz)

LC/MS (99%) ESI+ Calcd: 329.4: Found: 330.5 (M+1)

EXAMPLE 12

Preparation of A30

Synthesis of 1-(3,4-Difluoro-benzyl)-3a-methyl-1,3,3a,4,5,6-hexahydro-indol-2-one, K-41D: Following the general procedure P-1, (1-Methyl-2-oxo-cyclohexyl)-acetic acid (K-40) was converted to K-41D. Consistent with 1H-NMR.

Synthesis of 7-Bromo-1-(3,4-Difluoro-benzyl)-3a-methyl-1,3,3a,4,5,6-hexahydro-indol-2-one, K-42D: Following the general procedure P-2, 1-(3,4-Difluoro-benzyl)-3a-methyl-1,3,3a,4,5,6-hexahydro-indol-2-one, K-41D was converted to K-42D. Consistent with 1H-NMR.

Synthesis of (E)-3-[1-(3,4-Difluoro-benzyl)-3a-methyl-2-oxo-2,3,3a,4,5,6-hexahydro-1H-indol-7-yl]-acrylic acid methyl ester, K-43D: Following the general procedure P-3, 7-Bromo-1-(3,4-Difluoro-benzyl)-3a-methyl-1,3,3a,4,5,6-hexahydro-indol-2-one, K-42D was converted to K-43D. Consistent with 1H-NMR.

Synthesis of (E)-3-[1-(3,4-Difluoro-benzyl)-3a-methyl-2-oxo-2,3,3a,4,5,6-hexahydro-1H-indol-7-yl]-acrylic acid, A30: Following the general procedure P-4, (E)-3-[1-(3,4-Difluoro-benzyl)-3a-methyl-2-oxo-2,3,3a,4,5,6-hexahydro-1H-indol-7-yl]-acrylic acid methyl ester, K-43D was converted to A30. 1H-NMR (500 MHz, CDCl$_3$) 1.21 (s, 3H), 1.61 (m, 1H), 1.80 (m, 1H), 1.88 (ddd, 2H, J=16.0, 9.2,4.0 Hz), 2.29 (m, 2H), 2.45 (s, 2H), 4.83 (d, 1H, J=16.0 Hz), 5.15 (d, 1H, J=16.4 Hz), 5.65 (d, 1H, J=15.2 Hz), 7.011 (m, 1H), 7.06-7.15 (m, 2H), 7.78 (d, 1H, J=15.6 Hz)

LC/MS (100%) ESI+ Calcd: 347.4; Found: 348.5 (M+1)

EXAMPLE 13

Preparation of A32

Synthesis of 1-(2,4-Dichloro-benzyl)-3a-methyl-1,3,3a,4,5,6-hexahydro-indol-2-one, K-41E: Following the general procedure P-1, (1-Methyl-2-oxo-cyclohexyl)-acetic acid (K-40) was converted to K-41E. Consistent with 1H-NMR.

Synthesis of 7-Bromo-1-(2,4-Dichloro-benzyl)-3a-methyl-1,3,3a,4,5,6-hexahydro-indol-2-one, K-42E: Following the general procedure P-2, 1-(2,4-Dichloro-benzyl)-3a-methyl-1,3,3a,4,5,6-hexahydro-indol-2-one, K-41E was converted to K-42E. Consistent with 1H-NMR.

Synthesis of (E)-3-[1-(2,4-Dichloro-benzyl)-3a-methyl-2-oxo-2,3,3a,4,5,6-hexahydro-1H-indol-7-yl]-acrylic acid methyl ester, K-43E: Following the general procedure P-3, 7-Bromo-1-(2,4-Dichloro-benzyl)-3a-methyl-1,3,3a,4,5,6-hexahydro-indol-2-one, K-42E was converted to K-43E. Consistent with 1H-NMR.

Synthesis of (E)-3-[1-(2,4-Dichloro-benzyl)-3a-methyl-2-oxo-2,3,3a,4,5,6-hexahydro-1H-indol-7-yl]-acrylic acid, A32: Following the general procedure P-4, (E)-3-[1-(2,4-Dichloro-benzyl)-3a-methyl-2-oxo-2,3,3a,4,5,6-hexahydro-1H-indol-7-yl]-acrylic acid methyl ester, K-43E was converted to A32. 1H-NMR (500 MHz, CDCl$_3$) 1.29 (s, 3H), 1.63 (ddd, 1H, J=19.0, 14.0, 5.5 Hz), 1.82 (m, 1H), 1.88-1.91 (m, 2H), 2.23 (m, 1H), 2.34 (dd, 1H, J=17.0, 7.5 Hz), 2.46 (dd, 2H, J=24.0, 16.0 Hz), 4.96 (d, 1H, J=17.0 Hz), 5.04 (d, 1H, J=17.5 Hz), 5.61 (d, 1H, J=15.5 Hz), 6.94 (d, 1H, J=8.5 Hz), 7.18 (dd, 1H, J=8.0, 1.5 Hz), 7.38 (s, 1H), 7.42 (d, 1H, J=9.5 Hz), 7.42 (d, 1H, J=2.0 Hz)

LC/MS (99%) ESI+ Calcd: 380.3; Found: 380.3

EXAMPLE 14

Preparation of A35

Synthesis of 1-(3-Chloro-benzyl)-3a-methyl-1,3,3a,4,5,6-hexahydro-indol-2-one, K-41F: Following the general procedure P-1, (1-Methyl-2-oxo-cyclohexyl)-acetic acid, (K-40) was converted to K-41F. Consistent with 1H-NMR.

Synthesis of 7-Bromo-1-(3-Chloro-benzyl)-3a-methyl-1,3,3a,4,5,6-hexahydro-indol-2-one, K-42F: Following the general procedure P-2, 1-(3-Chloro-benzyl)-3a-methyl-1,3,3a,4,5,6-hexahydro-indol-2-one, K-41F was converted to K-42F. Consistent with 1H-NMR.

Synthesis of (E)-3-[1-(3-Chloro-benzyl)-3a-methyl-2-oxo-2,3,3a,4,5,6-hexahydro-1H-indol-7-yl]-acrylic acid methyl ester, K-43F: Following the general procedure P-3, 7-Bromo-1-(3-Chloro-benzyl)-3a-methyl-1,3,3a,4,5,6-hexahydro-indol-2-one, K-42F was converted to K-43F. Consistent with 1H-NMR.

Synthesis of (E)-3-[1-(3-Chloro-benzyl)-3a-methyl-2-oxo-2,3,3a,4,5,6-hexahydro-1H-indol-7-yl]-acrylic acid, A35: Following the general procedure P-4, (E)-3-[1-(3-Chloro-benzyl)-3a-methyl-2-oxo-2,3,3a,4,5,6-hexahydro-1H-indol-7-yl]-acrylic acid methyl ester, K-43F was converted to A35. 1H NMR (400 MHz, DMSO-d6) 1.16 (s, 3H), 1.60 (m, 1H), 1.68-1.82 (m, 3H), 2.10-2.30 (m, 2H), 2.33 (d, J=16.0 Hz, 1H), 2.61 (d, J=16.0 Hz, 1H), 4.78 (d, J=16.8 Hz, 1H), 5.04 (d, J=16.8 Hz, 1H), 5.53 (d, J=15.2 Hz, 1H), 7.13 (m, 1H), 7.29 (m, 1H), 7.32 (m, 2H), 7.54 (d, J=15.2 Hz, 1H), 11.91 (br s, 1H).

LCMS(97.1%) (ESI+) Calcd for 345.8; Found: 346.2 (M+1).

EXAMPLE 15

Preparation of A36

Synthesis of 1-(2,3-Dichloro-benzyl)-3a-methyl-1,3,3a,4,5,6-hexahydro-indol-2-one, K-41G: Following the general procedure P-1, (1-Methyl-2-oxo-cyclohexyl)-acetic acid (K-40) was converted to K-41G. Consistent with 1H-NMR.

Synthesis of 7-Bromo-1-(2,3-Dichloro-benzyl)-3a-methyl-1,3,3a,4,5,6-hexahydro-indol-2-one, K-42G: Following the general procedure P-2, 1-(2,3-Dichloro-benzyl)-3a-methyl-1,3,3a,4,5,6-hexahydro-indol-2-one, K-41G was converted to K-42G. Consistent with 1H-NMR.

Synthesis of (E)-3-[1-(2,3-Dichloro-benzyl)-3a-methyl-2-oxo-2,3,3a,4,5,6-hexahydro-1H-indol-7-yl]-acrylic acid methyl ester, K-43G: Following the general procedure P-3, 7-Bromo-1-(2,3-Dichloro-benzyl)-3a-methyl-1,3,3a,4,5,6-hexahydro-indol-2-one, K-42G was converted to K-43G. Consistent with 1H-NMR.

Synthesis of (E)-3-[1-(2,3-Dichloro-benzyl)-3a-methyl-2-oxo-2,3,3a,4,5,6-hexahydro-1H-indol-7-yl]-acrylic acid, A36: Following the general procedure P-4, (E)-3-[1-(2,3-Dichloro-benzyl)-3a-methyl-2-oxo-2,3,3a,4,5,6-hexahydro-1H-indol-7-yl]-acrylic acid methyl ester, K-43G was converted to A36. 1H-NMR (500 MHz, CDCl$_3$) 1.30 (s, 3H), 1.64 (m, 1H), 1.83 (m, 1H), 1.87-1.93 (m, 2H), 2.23 (m, 1H), 2.35 (dd, 1H, J=16.0, 6.4 Hz), 2.48 (dd, 2H, J=24.0, 16.0 Hz), 4.96 (d, 1H, J=17.2 Hz), 5.12 (dd, 1H, J=17.2 Hz), 5.59 (d, 1H, J=15.2 Hz), 6.91 (dd, 1H, J=8.0, 1.6 Hz), 7.16 (dd, 1H, J=8.0 Hz), 7.32 (d, 1H, J=15.2 Hz), 7.39 (dd, 1H, J=8.0, 1.6 Hz)

LC/MS (99%) ESI+ Calcd: 380.3; Found: 380.2

EXAMPLE 16

Preparation of A29

Synthesis of 1-(3-Methoxy-benzyl)-3a-methyl-1,3,3a,4,5,6-hexahydro-indol-2-one, K-41H: Following the general procedure P-1, (1-Methyl-2-oxo-cyclohexyl)-acetic acid (K-40) was converted to K-41H. Consistent with 1H-NMR.

Synthesis of 7-Bromo-1-(3-Methoxy-benzyl)-3a-methyl-1,3,3a,4,5,6-hexahydro-indol-2-one, K-42H: Following the general procedure P-2, 1-(3-Methoxy-benzyl)-3a-methyl-1,3,3a,4,5,6-hexahydro-indol-2-one, K-41H was converted to K-42H. Consistent with 1H-NMR.

Synthesis of (E)-3-[1-(3-Methoxy-benzyl)-3a-methyl-2-oxo-2,3,3a,4,5,6-hexahydro-1H-indol-7-yl]-acrylic acid methyl ester, K-43H: Following the general procedure P-3, 7-Bromo-1-(3-Methoxy-benzyl)-3a-methyl-1,3,3a,4,5,6-hexahydro-indol-2-one, K-42H was converted to K-43H. Consistent with 1H-NMR.

Synthesis of (E)-3-[1-(3-Methoxy-benzyl)-3a-methyl-2-oxo-2,3,3a,4,5,6-hexahydro-1H-indol-7-yl]-acrylic acid, A29: Following the general procedure P-4, (E)-3-[1-(3-Methoxy-benzyl)-3a-methyl-2-oxo-2,3,3a,4,5,6-hexahydro-1H-indol-7-yl]-acrylic acid methyl ester, K-43H was converted to A29. 1H NMR (400 MHz, DMSO-d6) 1.23 (s, 3H), 1.6-1.8 (m, 4H), 2.11 (s, 2H), 2.26 (m, 2H), 3.77 (s, 3H), 4.75 (d, J=16.4, 1H), 5.30 (d, J=16.4, 1H), 5.61(d, J=16.2, 1H), 6.80 (m, 3H), 7.21(m, 2H), 7.90 (d, J=15.2, 1H). LC/MS=99.5% purity, MS (ESI+) Calcd. (MW) 341; Found: 342 (M+H).

EXAMPLE 17

Preparation of A13

Indole-7 carboxyldehyde (K-44). Methyl 7-indolecarboxylate was prepared according to literature procedure {Batcho B. and Leimgruber, K., Org. Syn. Vol IIV, page 34-40). To a solution of methyl 7-indolecarboxylate (13 g, 74.2 mmol) in anhydrous THF (250 mL) was added LiAlH$_4$ (10.9 g, 0.288 mol) in portions, and reaction mixture was heated to reflux for 2 h. After cooling to room temperature, the excess hydride was quenched by addition of water (12mL), 15% NaOH (12 mL) and water (26 mL). The solids were removed by filtration through a pad of Celite and filtrate was evaporated in vacuo to yield (1H-indol-7-yl)-methanol (10.7 g, 98%). $^1$HNMR (CDCl$_3$). To a solution of the alcohol, (1H-indol-7-yl)-methanol (8.0 g, 54.3 mmol) in 400 mL of methylene chloride was added activated manganese (IV) oxide (85%, 41.0 g, 0.40 mol), and stirred at ambient temperature for 72 h. After additional of 200 mL of methylene chloride and 400 mL of methanol to the reaction mixture, the whole mixture was filtered through a pad of silica gel to remove solid materials. The filtrate was concentrated to afford a crude product, which was purified by a column chromatography on silica gel to yield 1H-indole-7-carbaldehyde, K-44 (6.55 g, 83%).

$^1$HNMR (CDCl$_3$).

(E)-3-(1H-Indol-7-yl)-acrylic acid ethyl ester (K-45). To a 100 mL round bottom flask which contained a suspension of NaH (60% in mineral oil, 320 mg, 8 mmol) in THF (20 mL) was added triethylphosphonoacetate (1.5 g, 6.6 mmol) at 0° C. The resulting mixture was allowed to warm to room temperature and stir at for 2 h and then cooled to 0° C. To this solution, 1H-indole-7-carboxaldehyde (K-44, 450 mg, 3 mmol) was added at 0° C. The resulting reaction mixture was allowed to warm to room temperature and stir for 2 h, then heated and stirred at 78° C. for 14 h. The reaction mixture was cooled to 5° C. and was quenched with the addition of saturated aqueous NH$_4$Cl (15 mL) followed by extraction of EtOAc (3×30 mL). The combined organic extracts were washed with brine (2×20 mL), dried (Na$_2$SO$_4$), filtered and the solvent was removed under reduced pressure. The residue was purified by flash chromatography (silica gel, EtOAc/hexane=1:20-1:8) to afford desired 3-(1H-indol-7-yl)-acrylic acid ethyl ester K-45 (450 mg, 68%) as a white solid. MS(ESI$^-$) m/z(216.3, 100%). 1HNMR, 13CNMR.

(E)-3-(3-Acetyl-1H-indol-7-yl)-acrylic acid ethyl ester, K-46. To a predried, 100 mL round bottom flask which contained a solution of K-45 (645 m g, 3 mmol) in DMA (5 mL) was added POCl$_3$ (330 uL) at 0-5° C. drop wise. The resulting reaction mixture was allowed to warm to room temperature and stir for 20 min and then heated and stirred at 40° C. for 1 h. The reaction mixture was cooled to 0° C. and poured into an ice-water suspension (50 mL) which was followed by the addition of aqueous NaOH (0.5 g in 10 mL water). The mixture was extracted with EtOAc (3×50 mL), the combined organic layers were washed with water (3×50 mL), dried (Na$_2$SO$_4$) and the solvent was removed under reduced pressure to provide the K-46 (450 mg, 58% yield) as a yellow solid.

MS (ESI$^-$): 256.3 (M−1). 1H-NMR (500 MHz, CDCl$_3$).

(E)-3-[3-Acetyl-1-(2,4-dichloro-benzyl)-1H-indol-7-yl]-acrylic acid ethyl ester, K-47. To a 250 mL round-bottomed flask containing a stirring suspension of K-46 (400 mg, 1.6 mmol), KI (300 mg) and Cs$_2$CO$_3$ (600 mg) in DMF (40 mL) was added 2,4-dichlorobenzyl chloride (350 mg, 1.8 mmol) at room temperature. The resulting reaction mixture was stirred at room temperature for 72 h. The mixture was cooled to 0° C. and saturated aqueous NH$_4$Cl (10 mL) was added which was followed by extraction with ethyl acetate (2×100 mL). The combined organic extracts were washed with water (3×100 mL), dried (Na$_2$SO$_4$), filtered and the solvent was removed under reduced pressure to provide a residue which was purified by flash chromatography (silica gel, CH$_2$Cl$_2$; EtOAc/hexane=1:8-1:2) to yield K-47 (480 mg, 74% yield) as an yellow solid. MS (ESI$^+$): 416.7 (M). 1H-NMR.

(E)-3-[3-Acetyl-1-(2,4-dichloro-benzyl)-1H-indol-7-yl]-acrylic acid, A13. To a 50 mL round bottom flask containing a solution of NaOH (300 mg, 7.5 mmol) in EtOH (20 mL) and H$_2$O (10 mL) was added K-47 (300 mg, 0.7 mmol) at 5° C. The resulting reaction mixture was heated and stirred at 50° C. for 5 h. The reaction mixture was cooled to 0° C. and was acidified through the addition of 10% aqueous HCl until a pH of 1 was reached. The mixture was diluted with water (100 mL) and then extracted with dichloromethane-MeOH (10: 1, 3×20 mL). The combined organic extracts were dried over Na$_2$SO$_4$ and the solvent was removed in vacuo to afford a residue which was purified by recrystallization with acetone/ ethyl acetate/hexanes to afford A13 (260 mg, 90% yield) as an yellow solid. 1H NMR (500 MHz, DMSO-d6) 2,47 (s, 3H), 5.72 (s, 2H), 6.16 (d, J=16.0 Hz, 1H), 6.31 (d, J=8.5 Hz, 1H), 7.27-7.7.30 (m, 2H), 7.41 (d, J=7.5 Hz, 1H), 7.69-7.72 (m, 2H), 8.37 (d, J=7.5 Hz, 1H), 8.53 (s, 1H), LC/MS (90%) ESI− Calcd: 388.2; Found: 386.4 (M−2).

EXAMPLE 18

Preparation of A14

(E)-3-[1-(2,4-Dichloro-benzyl)-3-isopropenyl-1H-indol-7-yl]-acrylic acid ethyl ester, K-48. To a predried, 250 mL round-bottomed flask containing a stirring solution of $Ph_3PCH_3Br$ (1300 mg, 0.6 mmol) in THF (55 mL) was added BuLi (2.0 mL, 1.6 M in ether) at 0° C. The resulting reaction mixture was allowed to warm to room temperature then heated and stir 40° C. for 2 h. The mixture was cooled to 0° C. and K-47 (460 mg, 1.1 mmol) was added at 0° C. The mixture was warmed to room temperature then heated and stir 40° C. for 3 h. After cooling to 0° C., the reaction was quenched with saturated aqueous $NH_4Cl$ (5 mL) which was followed by extraction with EtOAc (2×100 mL). The combined organic extracts were washed with water (3×100 mL), dried ($Na_2SO_4$), filtered and the solvent was removed under reduced pressure to provide a residue which was purified by flash chromatography (silica gel, EtOAc/hexane=1:8-1:4) to yield the K-48 (380 mg, 85% yield)) as a light yellow solid. MS (ESI+): 414.8 (M). 1H-NMR.

3-[1-(2,4-Dichloro-benzyl)-3-isopropyl-1H-indol-7-yl]-2-methyl-propionic acid ethyl ester, K-49. To a 50 mL round-bottomed flask containing a solution of K-48 (260 mg, 0.6 mmol) in EtOH (55 mL) was added Pd/C (30 mg) at room temperature. The flask was evacuated and charged with $H_2$ 3 times and the resulting reaction mixture was stirred at room temperature for 16 h. The catalyst was filtered out and washed with EtOAc (3×50 mL). The filtrate was washed with water (3×50 mL), dried ($Na_2SO_4$), filtered and the solvent was removed in vacuo to afford K-49 (240 mg, 95% yield) as an off-white solid. 1H-NMR.

3-[1-(2,4-Dichloro-benzyl)-3-isopropyl-1H-indol-7-yl]-2-methyl-propionic acid ethyl ester, A14. To a 50 mL round-bottomed flask containing a solution of NaOH (200 mg, 5 mmol) in EtOH (30 mL) and $H_2O$ (20 mL) was added K-48 (180 mg, 0.4 mmol) at 5° C. The resulting reaction mixture was heated and stirred at 50° C. for 5 h. The reaction mixture was cooled to 0° C. and was acidified through the addition of 10% aqueous HCl until a pH of 1 was reached. The mixture was diluted with water (100 mL) and then extracted with dichloromethane-MeOH (10:1, 3×20 mL). The combined organic extracts were dried ($Na_2SO_4$), filtered and the solvent was removed in vacuo to afford a residue which was purified by recrystallization with acetone/ethyl acetate/hexanes to afford A14 (150 mg, 90% yield) as a yellow solid. 1H NMR (500 MHz, DMSO-d6) 1.29 (d, J=8.0 Hz, 6H), 2.12 (t, J=5.0 Hz, 2H), 2.77(t, J=5.0 Hz, 2H), 3.13-3.17 (m, 1H), ) 5.63 (s, 2H), 6.99 (d, J=8.5 Hz, 1H), 6.88-6.94 ((m, 2H)), 7.08 (s, 1H), 7.25 (dd, J=8.5 Hz, J=1.5 Hz, 1H), 7.40 (d, J=6.5 Hz, 1H), 7.66 (d, J=1.5 Hz, 1H), 8.32 (s, 1H).

LC/MS (>85%) ESI− Calcd: 390.3; Found: 390.5 (M), 388.3 (M−2).

EXAMPLE 19

Preparation of A11

(E)-3-(3-Formyl-1H-indol-7-yl)-acrylic acid ethyl ester, K-50 To a predried 100 mL round bottom flask containing a solution of ester K-45 (2.6 g, 13 mmol) in DMF (5.2 mL) was added $POCl_3$ (1250 uL) at 0-5° C. dropwise. The resulting reaction mixture was allowed to warm to room temperature and stir for 20 min and then heated and stirred at 40° C. for 1 h. The reaction mixture was cooled to 0° C. and was poured into ice-water (50 mL) which was followed by the addition of aqueous NaOH (1.5 g in 20 mL water). The mixture was extracted with EtOAc (3×100 mL), the combined organic extracts were washed with water (3×100 mL), dried ($Na_2SO_4$), filtered and the solvent was removed under reduced pressure to provide K-50 (2.0 g, 75%) as an yellow solid. MS (ESI−): 242.2 (M−1). 1H-NMR (500 MHz, $CDCl_3$).

E)-3-[1-(2,4-Dichloro-benzyl)-3-formyl-1H-indol-7-yl]-acrylic acid ethyl ester, K-51. To a 250 mL round-bottomed flask containing a stirring suspension of K-50 (480 mg, 2 mmol), KI (500 mg) and $Cs_2CO_3$ (1 g) in DMF (40 mL) was added 2,4-dichlorobenzyl chloride (440 mg, 2.4 mmol) at room temperature. The resulting reaction mixture was stirred at room temperature for 72 h. The mixture was cooled to 0° C. and saturated aqueous $NH_4Cl$ (10 mL) was added and the mixture was extracted with ethyl acetate (2×100 mL). The combined organic extracts were washed with water (3×100 mL), dried (Na2SO4), filtered and the solvent was removed under reduced pressure to provide a residue which was purified by flash chromatography (silica gel, $CH_2Cl_2$; EtOAc/hexane=1:4-1:2) to yield the K-51 (400 mg, 50%) as an yellow solid. MS (ESI+): 402.3 (M+1). 1H-NMR.

(E)-3-[1-(2,4-Dichloro-benzyl)-3-formyl-1H-indol-7-yl]-acrylic acid, A11. To a 50 mL round-bottomed flask containing a solution of NaOH (80 mg, 2 mmol) in EtOH (5 mL) and $H_2O$ (3 mL) was added K-51 (80 mg, 0.2 mmol) at 5° C. The resulting reaction mixture was heated and stirred at 50° C. for 4 h. The reaction mixture was cooled to 0° C. and was acidified through the addition of 10% aqueous HCl until a pH of 1 was reached. The mixture was diluted with water (20 mL) and then extracted with dichloromethane-MeOH (10: 1, 3×20 mL). The combined organic extracts were dried ($Na_2SO_4$), filtered and the solvent was removed in vacuo to afford a residue which was purified by recrystallization with acetone/ethyl acetate/hexanes to afford A11 (60 mg, 80% yield) as a yellow solid. 1H NMR (500 MHz, DMSO-d6) 5.77 (s, 2H), 6.18 (d, J=15.5 Hz, 1H), 6.40 (d, J=3.5 Hz, 1H), 7.30-7.47 (m, 2H), 7.46 (d, J=2.5 Hz, 1H), 7.71-7.77 (m, 2H), 8.28 (d, J=7.5 Hz, 1H), 8.42 (s, 1H), 10.00 (s, 1H), LC/MS (>90%) ESI− Calcd: 374.2; Found: 374.2 (M).

EXAMPLE 20

Preparation of A10

(E)-3-[1-(2,4-Dichloro-benzyl)-3-hydroxymethyl-1H-indol-7-yl]-acrylic acid ethyl ester K-52. To a 100 mL round-bottomed flask containing a stirring suspension of K-51 (100 mg, 0.25 mmol) in EtOH (5 mL) was added $NaBH_4$ (100 mg, excess) at 0° C. The resulting reaction mixture was allowed to warm to room temperature and stir for 4 h. The mixture was cooled to 0° C., saturated aqueous $NH_4Cl$ (5 mL) was added and the mixture was extracted with $CH_2Cl_2$ (2×30 mL). The combined organic extracts were washed with water (3×30 mL), dried ($Na_2SO_4$), filtered and the solvent was removed under reduced pressure to provide a residue which was purified by flash chromatography (silica gel, $CH_2Cl_2$; EtOAc/hexane (1:4 to 1:1 gardient) to yield the K-52 (85 mg, 84% yield) as an off-white solid. MS (APCI+): 406.2 (M+2). 1H-NMR.

(E)-3-[1-(2,4-Dichloro-benzyl)-3-hydroxymethyl-1H-indol-7-yl]-acrylic acid, A10. To a 50 mL round bottom flask containing a solution of K-52 (80 mg, 0.2 mmol) in MeOH (15 mL) was added 2N aqueous NaOH (0.5 mL) at room temperature. The resulting reaction mixture was heated and stirred at 80° C. for 48 h. The reaction mixture was cooled to 0° C. and was acidified through the addition of 10% aqueous HCl until a pH of 1 was reached. The mixture was diluted with water (20 mL) and then extracted with dichloromethane-MeOH (10:1, 3×20 mL). The combined organic extracts were dried ($Na_2SO_4$), filtered and the solvent was removed in vacuo to afford a residue which was purified by flash chromatography (silica gel, $CH_2Cl_2$; EtOAc/hexane=1:4-1:1, EtOAc) to yield the A10 (65 mg, 80% yield) as an off-white solid. 1H NMR (500 MHz, DMSO-d6) 4.68 (d, J=3.0 Hz, 2H), 5.58 (d, J=18.5 Hz, 2H), 7.09 (s, 1H), 7.17 (t, J=8.0 Hz, 1H), 7.26-7.7.31 (m, 2H), 7.38-7.7.39 (m, 2H), 7.43 (s, 1H), 7.45 (s, 1H), 7.82 (d, J=15.5 Hz, 1H). LC/MS (93%) ESI– Calcd: 375.2; Found: 374.3 (M–1).

EXAMPLE 21

Preparation of A12

(E)-3-[1-(2,4-Dichloro-benzyl)-3-methoxymethyl-1H-indol-7-yl]-acrylic acid methyl ester, K-53. To a 25 mL round-bottomed flask containing a stirring suspension of NaH (15 mg, 0.25 mmol) in DMF (5 mL) was added A10 (30 mg, 0.08 mmol) at 0° C. The resulting mixture was allowed to warm to room temperature and stir for 90 min. The mixture was then cooled to 0° C. and MeI (1 mL) was added. This reaction mixture was allowed to warm to room temperature and stir at for 72 h. The mixture was recooled to 0° C., saturated aqueous $NH_4Cl$ (1 mL) was added and the mixture was extracted with EtOAc (2×5 mL). The combined organic extracts were washed with water (2×5 mL), dried ($Na_2SO_4$), filtered and the solvent was removed under reduced pressure to provide a residue which was purified by flash chromatography (silica gel, EtOAc/hexane=1:8) to yield K-52 (17 mg, 50% yield) as an off-white solid. 1H-NMR.

(E)-3-[1-(2,4-Dichloro-benzyl)-3-methoxymethyl-1H-indol-7-yl]-acrylic acid, A12. To a 50 mL round bottom flask containing a solution of NaOH (50 mg, 1.2 mmol) in MeOH (1 mL) and water (2 mL) was added K-53 (17 mg, 0.04 mmol) at room temperature. The resulting reaction mixture which was heated and stirred at 50° C. for 4 h, cooled to 5° C., acidified through the addition of 10% aqueous HCl until a pH of 1 was reached. After diluted with water (10 mL) the mixture was extracted with dichloromethane-MeOH (10:1, 3×5 mL). The combined organic extracts were dried ($Na_2SO_4$), filtered and the solvent was removed in vacuo to afford a residue which was purified by flash chromatography (silica gel, $CH_2Cl_2$; EtOAc/hexane=1:4-1:1, EtOAc) to yield the A12 (15 mg, 90% yield) as an off-white solid. 1H NMR (500 MHz, methanol-d4) 3.40 (s, 3H), 4.69 (s, 2H), 5.61 (s, 2H), 6.15 (d, J=15.5 Hz, 1H), 6.32 (d, J=8.5 Hz, 1H), 7.13-7.16 (m, 2H), 7.31-7.36 (m, 2H), 7.52 (d, J.=1.5 Hz, 1H), 7.50 (d, J=8.5 Hz, 1H), 7.90 (d, J=15.0 Hz, 1H), 8.42 (s, 1H), 10.00 (s, 1H), LC/MS (>70%) ESI– Calcd: 390.2; Found: 388.3(M–2), 390.2 (M).

EXAMPLE 22

Preparation of A31

(E)-3-(5-fluoro-3-methyl-1H-indol-7-yl)-acrylic acid tert-butyl ester, K-54. To a 20 mL vial equipped with a magnetic stir bar and charged with 7-bromo-5-fluoro-3-methyl-1H-indole, [which was prepared according to method of Dobbs A. J. Org,. Chem. 2001, 66, 638-641] (1.005 g, 4.41 mmol) was added anhydrous DMF (8 mL), tert-butyl acrylate (1.94 mL, 13.23 mmol), triethylamine (1.84 mL, 13.23 mmol) and tri-o-tolylphosphine (268 mg, 0.88 mmol). The homogenous solution was degassed by passing a stream of $N_2$ gas through the solution for 20 min. Palladium acetate (49.4 mg, 0.22 mmol) was added, degassing was continued for 10 min, the vial was sealed with a cap and placed in an oil bath at 100° C. overnight. After 10 h the reaction mixture was diluted with EtOAc (100 mL) and water (50 mL), shaken in a separatory funnel and separated. The aqueous layer was extracted with EtOAc (50 mL) and the combined organic extracts were washed with water (3×50 mL), dried ($Na_2SO4$), filtered and concentrated to give a brown oil. The residue was purified by flash chromatography utilizing 9:1 hexane/acetone as eluent to give 1.16 g (96%) of K-54 as a yellow solid. 1H NMR.

(E)-3-[1-(2,4-dichloro-benzyl)-5-fluoro-3-methyl-1H-indol-7-yl]-acrylic acid tert-butyl ester, K-55. To a 250 mL round-bottomed, one-necked flask containing K-54 (300 mg, 1.09 mmol) was added anhydrous DMF (4 mL) and 2,4-dichlorobenzyl chloride (181 μL, 1.31 mmol). To this stirring solution was added potassium tert-butoxide (184 mg, 1.64 mmol) giving a deep red color (from light yellow). After 1.5 h the reaction mixture was diluted with water and EtOAc (20 mL each) and the mixture was transfer to a separatory funnel and shaken. The aqueous layer was extracted with EtOAc (20 mL) and the combined organic extracts were washed with one-third saturated aqueous NaCl (3×20 mL) and dried ($Na_2SO_4$). The solution was filtered and concentrated to give 530 mg of brown oil. The residue was purified by flash chromatography utilizing 99:1 hexane/acetone as eluent to give 323 mg (68%) of K-55 as an off-white solid. 1H NMR.

(E)-3-[1-(2,4-dichloro-benzyl)-5-fluoro-3-methyl-1H-indol-7-yl]-acrylic acid, A31. To a 20 mL vial containing K-55 (321 mg, 0.739 mmol) was added a magnetic stir bar and anhydrous $CH_2Cl_2$ (3 mL). To this stirring solution is added trifluoroacetic acid (285 μL, 3.69 mmol). The vial was capped and the reaction mixture was stirred at room temperature overnight. The reaction mixture was diluted with anhydrous $CH_2Cl_2$ (5 mL) and the sticky yellow solid was suspended and filtered. The solid mass weighed 135 mg. The mother liquor from the filtration was concentrated and triturated with $CH_2Cl_2$ (2 mL) and filtered to give an additional 45 mg of product. Total yield was 180 mg (64%) of (E)-3-[1-(2,4-dichloro-benzyl)-5-fluoro-3-methyl-1H-indol-7-yl]-acrylic acid (A31) as a yellow solid. 1H NMR (DMSO-d6) 2.26 (s, 3H), 5.56 (s, 2H), 6.21 (d, J=8 Hz, 1H), 6.24 (d, J=15 Hz, 1H), 7.21 (dd, J=10 and 2 Hz, 1H), 7.28 (dd, J=8 and 2 Hz, 1H), 7.35 (s, 1H), 7.43 (dd, J=8 and 2 Hz, 1H), 7.65 (d, J=15 Hz, 1H), 7.67 (d, J=2 Hz, 1H), 12.2 (b, 1H). LC/MS (99%) ESI– Calcd. 378.2 m/z Found: 378.2 m/z

EXAMPLE 23

Preparation of A44

Synthesis of 4-Bromo-1-methyl-1H-indole, K-56. To a solution of NaH (60% in oil, 600 mg, 15 mmol) in DMF (20 mL), 4-bromoindole (1.96 g, 10 mmol) was added at –10° C. and stirred at room temperature for 10 min. Iodomethane (6.7 g, 50 mmol) was added at –10° C. The reaction mixture was stirred at room temperature for 3 h and then diluted with methylene chloride (200 mL). The reaction mixture was washed with water (3×200 mL), brine and dried over sodium sulfate. The mixture was filtered and concentrated to give 3 g of K-56 that was used without further purification. 1H-NMR.

General Procedure (P-5): Coupling of 4-bromoindole K-56 with selected phenols, Products K-57x. A mixture of K-56 (420 mg, 2 mmol), CuI (38 mg, 0.2 mmol, 0.1 eq.), N,N-dimethylglycine HCl salt (84 mg, 0.6 mmol, 0.3 eq.), the appropriate phenol (3 mmol, 1.5 eq) and $Cs_2CO_3$ (1.3 g, 4 mmol, 2 e.q.) in dioxane (4 mL) was stirred under Ar at 105° C. for 3 days. The reaction mixture was diluted with ethyl acetate and washed with water, brine and dried over sodium sulfate. After filtration and removal of the solvent, the residue was purified by column chromatography on silica gel with ethyl acetate/hexane as an eluent to give K-57x.

General Procedure (P-6): Conversion of indole to 3-formaldehyde indole to provide products K-58x. To a solution of K-57x (1.6 mmol) in DMF (8 mL), $POCl_3$ (1.8 mmol, 1.1 e.q.) was added drop wise at room temperature. The reaction mixture was stirred at 50° C. for 1 hr and then poured into ice-water. The pH of the resulting mixture was adjusted to 8-9 by addition of 2N aqueous NaOH and then stirred at room temperature for 30 min. The reaction mixture was extracted with ethyl acetate (2×40 mL). The organic phase was washed with water (3×50 mL), brine, and dried over sodium sulfate. After filtration and removal of the solvent, K-58x was obtained as a solid.

General Procedure (P-10): Conversion of 3-formaldehyde indole to 3-acrylic acid ethyl ester indole, K-59x. To a solution of NaH (60% in oil, 100 mg, 2.5 mmol, 2.5 eq.) in THF (20 mL), triethyl phosphonoacetate (493 mg, 2.2 mmol, 2.2 e.q.) was added at −10° C. and stirred at room temperature for 10 min. and then K-58x (1 mmol) dissolved in THF (10 mL) was added at −10° C. The reaction mixture was stirred at 60° C. overnight. The reaction mixture was diluted with ethyl acetate and washed with aqueous $NH_4Cl$, water (2×100 mL), brine and dried over sodium sulfate. After filtration and removal of the solvent, product K-59x was obtained.

General Procedure (P-8). Hydrolysis of 3-acrylic acid ethyl esters to 3-acrylic acids. A mixture of crude K-59x (1 mmol) in THF (10 mL), MeOH (10 mL) and 2N aqueous NaOH (10 mL) was stirred at 50° C. for 3 h. After removal of THF and MeOH, the reaction mixture was diluted with water (~20 mL), the pH was made acidic through the addition of 2N aqueous HCl and the mixture was extracted with ethyl acetate (2×30 mL). The combined organic extracts were washed with water (2×30 mL), brine and dried over sodium sulfate. After filtration and removal of solvent, the residue washed with ether to give the desired carboxylic acid product.

Synthesis of 1-Methyl-4-(naphthalen-2-yloxy)-1H-indole, K-57A. Following the general procedure P-5, K-56 was reacted with naphthalen-2-ol to provide compound K-57A. Consistent with 1H-NMR.

Synthesis of 1-Methyl-4-(naphthalen-2-yloxy)-1H-indole-3-carbaldehyde, K-58A. Following the general procedure P-6, K-57A was converted to formaldehyde K-58A. Consistent with 1H-NMR.

Synthesis of (E)-3-[1-Methyl-4-(naphthalen-2-yloxy)-1H-indol-3-yl]-acrylic acid ethyl ester, K-59A. Following the general procedure P-7, K-58A was converted to acrylic acid ethyl ester K-59A. Consistent with 1H-NMR.

Synthesis of (E)-3-[1-Methyl-4-(naphthalen-2-yloxy)-1H-indol-3-yl]-acrylic acid A44. Following the general procedure P-8, K-59A was hydrolyzed to acrylic acid A44. 1H NMR (DMSO-d6) 3.87 (s, 3H), 6.26 (d, J=16 Hz, 1H), 6.69 (d, J=7 Hz, 1H), 7.21 (dd, J=8 and 8 Hz, 1H), 7.35-7.50 (m, 5H), 7.77 (d, J=8 Hz, 1H), 7.91 (d, J=8 Hz, 1H), 7.96 (d, J=16 Hz, 1H), 7.98 (d, J=8 Hz, 1H), 8.08 (s, 1H), 11.8 (s, 1H).

HPLC (98%)

LC/MS (93%) ESI+ Calcd. 344.3 m/z Found: 344.1 m/z

EXAMPLE 24

Preparation of A39

Synthesis of 4-(3,4-Dichloro-phenoxy)-1-methyl-1H-indole, K-57B. Following the general procedure P-5, K-56, was reacted with 3,4-dichloro-phenol to provide compound K-57B. Consistent with 1H-NMR.

Synthesis of 4-(3,4-Dichloro-phenoxy)-1-methyl-1H-indole-3-carbaldehyde, K-58B: Following the general procedure P-6, K-57B, was converted to formaldehyde K-58B. Consistent with 1H-NMR.

Synthesis of (E)-3-[4-(3,4-Dichloro-phenoxy)-1-methyl-1H-indol-3-yl]-acrylic acid ethyl ester, K-59B: Following the general procedure P-7, K-58B was converted to acrylic acid ethyl ester K-59B. Consistent with 1H-NMR.

Synthesis of (E)-3-[4-(3,4-Dichloro-phenoxy)-1-methyl-1H-indol-3-yl]-acrylic acid, A39: Following the general procedure P-8, K-59B was hydrolyzed to acrylic acid A39. 1H NMR (DMSO-d6) 3.86 (s, 3H), 6.22 (d, J=16 Hz, 1H), 6.77 (d, J=8 Hz, 1H), 6.94 (dd, J=9 and 3 Hz, 1H), 7.24 (m, 2H), 7.41 (d, J=8 Hz, 1H), 7.60 (d, J=9 Hz, 1H), 7.82 (d, J=16 Hz, 1H), 8.08 (s, 1H), 11.8 (s, 1H).

HPLC (90%) LC/MS (89%) APCI+ Calcd. 363.2 m/z Found: 362.2 m/z

EXAMPLE 25

Preparation of A40

Synthesis of 4-(2,4-Dichloro-phenoxy)-1-methyl-1H-indole, K-57C: Following the general procedure P-5, K-56, was reacted with 2,4-dichloro-phenol to provide compound K-57C. Consistent with 1H-NMR.

Synthesis of 4-(2,4-Dichloro-phenoxy)-1-methyl-1H-indole-3-carbaldehyde, K-58C: Following the general procedure P-6, K-57C was converted to formaldehyde K-58C. Consistent with 1H-NMR.

Synthesis of (E)-3-[4-(2,4-Dichloro-phenoxy)-1-methyl-1H-indol-3-yl]-acrylic acid ethyl ester, K-59C: Following the general procedure P-7, K-58C was converted to acrylic acid ethyl ester K-59C. Consistent with 1H-NMR.

Synthesis of (E)-3-[4-(2,4-Dichloro-phenoxy)-1-methyl-1H-indol-3-yl]-acrylic acid, A40: Following the general procedure P-8, K-59C was hydrolyzed to acrylic acid A40. 1H NMR (DMSO-d6) 3.86 (s, 3H), 6.25 (d, J=16 Hz, 1H), 6.51 (d, J=8 Hz, 1H), 7.01 (d, J=9 Hz, 1H), 7.17 (dd, J=8 and 8 Hz, 1H), 7.35 (d, J=8 Hz, 1H), 7.40 (dd, J=9 and 2Hz, 1H), 7.79 (d, J=2 Hz, 1H), 7.92 (d, J=16 Hz, 1H), 8.09 (s, 1H), 11.8 (s, 1H).

HPLC (86%)

LC/MS (92%) APCI+ Calcd. 363.2 m/z Found: 363.2 m/z

EXAMPLE 26

Preparation of A41

Synthesis of 4-(4-Chloro-phenoxy)-1-methyl-1H-indole, K-57D: Following the general procedure P-5, K-56 was reacted with 4-chloro-phenol to provide compound K-57D. Consistent with 1H-NMR.

Synthesis of 4-(4-Chloro-phenoxy)-1-methyl-1H-indole-3-carbaldehyde, K-58D: Following the general procedure P-6, K-57D was converted to formaldehyde K-58D. Consistent with 1H-NMR.

Synthesis of (E)-3-[4-(4-Chloro-phenoxy)-1-methyl-1H-indol-3-yl]-acrylic acid ethyl ester, K-59D: Following the general procedure P-7, K-58D was converted to acrylic acid ethyl ester K-59D. Consistent with 1H-NMR.

Synthesis of (E)-3-[4-(4-Chloro-phenoxy)-1-methyl-1H-indol-3-yl]-acrylic acid, A41: Following the general procedure P-8, K-59D was hydrolyzed to acrylic acid A41. 1H NMR (DMSO-d6) 3.85 (s, 3H), 6.24 (d, J=16 Hz, 1H), 6.66 (d, J=8 Hz, 1H), 7.00 (d, J=9 Hz, 2H), 7.21 (dd, J=8 and 8 Hz, 1H), 7.36 (d, J=8 Hz, 1H), 7.41 (d, J=9 Hz, 2H), 7.87 (d, J=16 Hz, 1H), 8.07 (s, 1H), 11.8 (s, 1H).

HPLC (94%)

LC/MS (100%) APCI+ Calcd. 328.7 m/z Found: 328.3 m/z

EXAMPLE 27

Preparation of A42

Synthesis of 4-(3,4-Difluoro-phenoxy)-1-methyl-1H-indole, K-57E: Following the general procedure P-5, K-56, was reacted with 3,4-difluoro-phenol to provide compound K-57E. Consistent with 1H-NMR.

Synthesis of 4-(3,4-Difluoro-phenoxy)-1-methyl-1H-indole-3-carbaldehyde, K-58E: Following the general procedure P-6, K-57E was converted to formaldehyde K-58E. Consistent with 1H-NMR.

Synthesis of (E)-3-[4-(3,4-Difluoro-phenoxy)-1-methyl-1H-indol-3-yl]-acrylic acid ethyl ester, K-59E: Following the general procedure P-7, K-58E was converted to acrylic acid ethyl ester K-59E. Consistent with 1H-NMR.

Synthesis of (E)-3-[4-(3,4-Difluoro-phenoxy)-1-methyl-1H-indol-3-yl]-acrylic acid, A42: Following the general procedure P-8, K-59E was hydrolyzed to acrylic acid A42. 1H NMR (DMSO-d6) 3.85 (s, 3H), 6.23 (d, J=16 Hz, 1H), 6.66 (d, J=8 Hz, 1H), 6.80 (m, 1H), 7.18 (m, 1H), 7.20 (dd, J=8 and 8 Hz, 1H), 7.36 (d, J=8 Hz, 1H), 7.43 (m, 1), 7.88 (d, J=16 Hz, 1H), 8.07 (s, 1H), 11.8 (s, 1H).

HPLC (90%)

LC/MS (93%) APCI+ Calcd. 330.3 m/z Found: 330.3 m/z

EXAMPLE 28

Preparation of A37

Synthesis of 4-(2,4-Difluoro-phenoxy)-1-methyl-1H-indole, K-57F: Following the general procedure P-5, K-56, was reacted with 2,4-difluoro-phenol to provide compound K-57F. Consistent with 1H-NMR.

Synthesis of 4-(2,4-Difluoro-phenoxy)-1-methyl-1H-indole-3-carbaldehyde, K-58F: Following the general procedure P-6, K-57F was converted to formaldehyde K-58F. Consistent with 1H-NMR.

Synthesis of (E)-3-[4-(2,4-Difluoro-phenoxy)-1-methyl-1H-indol-3-yl]-acrylic acid ethyl ester, K-59F: Following the general procedure P-7, K-58F was converted to acrylic acid ethyl ester K-59F. Consistent with 1H-NMR.

Synthesis of (E)-3-[4-(2,4-Difluoro-phenoxy)-1-methyl-1H-indol-3-yl]-acrylic acid, A37. Following the general procedure P-8, K-59F was hydrolyzed to acrylic acid A37. 1H NMR (DMSO-d6) 3.85 (s, 3H), 6.29 (d, J=16 Hz, 1H), 6.42 (d, J=8 Hz, 1H), 7.13 (dd, J=8 and 8 Hz, 1H), 7.13 (m, 1H), 7.25 (m, 1H), 7.29 (d, J=8 Hz, 1H), 7.51 (m, 1H), 8.03 (d, J=16 Hz, 1H), 8.09 (s, 1H), 11.8 (s, 1H).

LC/MS (97%) ESI+ Calcd. 330.3 m/z Found: 330.5 m/z

EXAMPLE 29

Preparation of A38

Synthesis of 4-(3-Chloro-4-fluoro-phenoxy)-1-methyl-1H-indole, K-56H. Following the general procedure P-5, K-56 was reacted with 3-chloro-4-fluoro-phenol to provide compound K-57G. Consistent with 1H-NMR.

Synthesis of 4-(3-Chloro-4-fluoro-phenoxy)-1-methyl-1H-indole-3-carbaldehyde, K-58G: Following the general procedure P-6, K-57G was converted to formaldehyde K-58G. Consistent with 1H-NMR.

Synthesis of (E)-3-[4-(3-Chloro-4-fluoro-phenoxy)-1-methyl-1H-indol-3-yl]-acrylic acid ethyl ester, K-59G. Following the general procedure P-7, K-58G was converted to acrylic acid ethyl ester K-59G. Consistent with 1H-NMR.

Synthesis of (E)-3-[4-(3-Chloro-4-fluoro-phenoxy)-1-methyl-1H-indol-3-yl]-acrylic acid, A38. Following the general procedure P-8, K-59G was hydrolyzed to acrylic acid A38. 1H NMR (DMSO-d6) 3.85 (s, 3H), 6.24 (d, J=16 Hz, 1H), 6.66 (d, J=8 Hz, 1H), 7.00 (m, 1H), 7.20 (dd, J=8 and 8 Hz, 1H), 7.25 (m, 1H), 7.35 (d, J=8 Hz, 1H), 7.43 (dd, J=9 and 9 Hz, 1H), 7.88 (d, J=16 Hz, 1H), 8.07 (s, 1H), 11.8 (s, 1H).

HPLC (92%)

LC/MS (96%) ESI+ Calcd. 346.8 m/z Found: 346.9 m/z

EXAMPLE 30

Preparation of A43

Synthesis of 4-(4-Chloro-3-fluoro-phenoxy)-1-methyl-1H-indole, K-57H. Following the general procedure P-5, K-56 was reacted with 4-chloro-3-fluoro-phenol to provide compound K-57H. Consistent with 1H-NMR.

Synthesis of 4-(4-Chloro-3-fluoro-phenoxy)-1-methyl-1H-indole-3-carbaldehyde, K-58H: Following the general procedure P-6, K-57H was converted to formaldehyde K-58H. Consistent with 1H-NMR.

Synthesis of (E)-3-[4-(4-Chloro-3-fluoro-phenoxy)-1-methyl-1H-indol-3-yl]-acrylic acid ethyl ester, K-59H. Following the general procedure P-7, K-58H was converted to acrylic acid ethyl ester K-59H. Consistent with 1H-NMR.

Synthesis of (E)-3-[4-(4-Chloro-3-fluoro-phenoxy)-1-methyl-1H-indol-3-yl]-acrylic acid, A43: Following the general procedure P-8, K-59H was hydrolyzed to acrylic acid A43. 1H NMR (DMSO-d6) 3.86 (s, 3H), 6.22 (d, J=16 Hz, 1H), 6.67 (m, 2H), 7.11 (dd, J=10 and 3 Hz, 1H), 7.23 (dd, J=8 and 8 Hz, 1H), 7.41 (d, J=8 Hz, 1H), 7.54 (dd, J=9 and 9 Hz, 1H), 7.81 (d, J=16 Hz, 1H), 8.08 (s, 1H), 11.8 (s, 1H). HPLC (91%)

LC/MS (100%) APCI– Calcd. 344.7 m/z Found: 344.2 m/z

EXAMPLE 31

Preparation of A45

Synthesis of 4-(4-Chloro-2-fluoro-phenoxy)-1-methyl-1H-indole, K-57I: Following the general procedure P-5, K-56 was reacted with 4-chloro-2-fluoro-phenol to provide compound K-57I. Consistent with 1H-NMR.

Synthesis of 4-(4-Chloro-2-fluoro-phenoxy)-1-methyl-1H-indole-3-carbaldehyde, K-58I. Following the general procedure P-6, K-57I was converted to formaldehyde K-58I. Consistent with 1H-NMR.

Synthesis of (E)-3-[4-(4-Chloro-2-fluoro-phenoxy)-1-methyl-1H-indol-3-yl]-acrylic acid ethyl ester, K-59I. Following the general procedure P-7, K-58I was converted to acrylic acid ethyl ester K-59I. Consistent with 1H-NMR.

Synthesis of (E)-3-[4-(4-Chloro-2-fluoro-phenoxy)-1-methyl-1H-indol-3-yl]-acrylic acid, A45. Following the general procedure P-8, K-59I was hydrolyzed to acrylic acid A45. 1H NMR (DMSO-d6) 3.85 (s, 3H), 6.26 (d, J=16 Hz, 1H), 6.54 (d, J=8 Hz, 1H), 7.11 (dd, J=9 and 9 Hz, 1H), 7.16 (dd, J=8 and 8 Hz, 1H), 7.28 (m, 1H), 7.33 (d, J=8 Hz, 1H), 7.66 (dd, J=11 and 2 Hz, 1H), 7.94 (d, J=16 Hz, 1H), 8.08 (s, 1H), 11.8 (s, 1H).

HPLC (90%)

LC/MS (90%) ESI+ Calcd. 346.7 m/z Found: 346.2 m/z

EXAMPLE 32

Preparation of A46

Synthesis of 4-(2-Chloro-4-fluoro-phenoxy)-1-methyl-1H-indole, K-57J: Following the general procedure P-5, K-56 was reacted with 2-chloro-4-fluoro-phenol to provide compound K-57J. Consistent with 1H-NMR.

Synthesis of 4-(2-Chloro-4-fluoro-phenoxy)-1-methyl-1H-indole-3-carbaldehyde, K-58J. Following the general procedure P-6, K-57J was converted to formaldehyde K-58J. Consistent with 1H-NMR.

Synthesis of (E)-3-[4-(2-Chloro-4-fluoro-phenoxy)-1-methyl-1H-indol-3-yl]-acrylic acid ethyl ester, K-59J: Following the general procedure P-7, K-58J was converted to acrylic acid ethyl ester K-59J. Consistent with 1H-NMR.

Synthesis of (E)-3-[4-(2-Chloro-4-fluoro-phenoxy)-1-methyl-1H-indol-3-yl]-acrylic acid, A46: Following the general procedure P-8, K-59J was hydrolyzed to acrylic acid A46. 1H NMR (DMSO-d6) 3.85 (s, 3H), 6.28 (d, J=16 Hz, 1H), 6.36 (d, J=8 Hz, 1H), 7.13 (dd, J=8 and 8 Hz, 1H), 7.20 (m, 1H), 7.26 (m, 1H), 7.29 (d, J=8 Hz, 1H), 7.65 (dd, J=8 and 3 Hz, 1H), 8.01 (d, J=16 Hz, 1H), 8.08 (s, 1H), 11.8 (s, 1H).

HPLC (93%)

LC/MS (92%) ESI+ Calcd. 346.7 m/z Found: 346.2 m/z

EXAMPLE 34

Preparation of A49

Synthesis of: 3-[1-(3,4-Difluoro-benzyl)-3a-methyl-2-oxo-octahydro-indol-7-yl]-propionic acid methyl ester (K-62) and 3-[1-(3,4-Difluoro-benzyl)-3a-methyl-2-oxo-2,3,3a,4,5,6-hexahydro-1H-indol-7-yl]-propionic acid methyl ester (K-63). To a solution of compound K-43D in ethanol was added 10% Pd/C (0.1 g/g compound). The resultant mixture was degassed, and the atmosphere replaced with hydrogen 3 times. The mixture was stirred under hydrogen at ambient pressure for 5 days. The reaction mixture was filtered through celite, the cake washed with ethanol, and the filtrate concentrated. The crude reaction mixture was purified via silica gel chromatography, using dichloromethane as eluent, followed by silica gel chromatography using an ethyl acetate/hexanes gradient as eluent to provide compounds K-62 and K-63.

K-62: 3-[1-(3,4-Difluoro-benzyl)-3a-methyl-2-oxo-octahydro-indol-7-yl]-propionic acid methyl ester, MS ESI+ Calcd. 365.4 m/z Found: 366.0 m/z $^1$H NMR(CDCl$_3$). K-63: 3-[1-(3,4-Difluoro-benzyl)-3a-methyl-2-oxo-2,3,3a,4,5,6-hexahydro-1H-indol-7-yl]-propionic acid methyl ester. MS ESI+ Calcd. 363.4 m/z Found: 364 m/z $^1$H NMR(CDCl$_3$)

Synthesis of 3-[1-(3,4-Difluoro-benzyl)-3a-methyl-2-oxo-octahydro-indol-7-yl]-propionic acid, A49.

Following general procedure (P-4), compound K-62 was converted to A49 in quantitative yield. 1H-NMR (500 MHz, CDCl$_3$) 1.05 (s, 3H), 1.33-1.43 (m, 4H), 1.51-1.64 (m, 4H), 1.78 (m, 1H), 2.13 (d, 1H, J=16.4 Hz), 2.18 (m, 1H), 2.33 (d, 1H, J=16.4 Hz), 2.37 (m, 1H), 3.17 (d, 1H, J=4.4 Hz), 4.04 (d, 1H, J=15.6 Hz), 4.98 (d, 1H, J=15.6 Hz), 6.94 (m, 1H), 7.04 (ddd, 1H, J=10.0. 7.6, 2.0 Hz), 7.11 (ddd, 1H, J=16.4, 10.4, 8.4 Hz)

LC/MS (100%) APCI– Calcd: 351.4 Found: 351.4

EXAMPLE 35

Preparation of A50

Synthesis of 3-[1-(3,4-Difluoro-benzyl)-3a-methyl-2-oxo-2,3,3a,4,5,6-hexahydro-1H-indol-7-yl]-propionic acid, A50

Following general procedure (P-4), compound K-63 was converted to A50 in 61% yield. 1H-NMR (500 MHz, CDCl$_3$) 1.10 (s, 3H), 1.50 (ddd, 1H, J=16.8, 12.4, 4.4 Hz), 1.66-1.82 (m, 3H), 2.05-2.09 (m, 2H), 2.17-2.33 (m, 6H), 4.71 (d, 1H, J=16.4 Hz), 4.95 (d, 1H, J=16.4 Hz), 6.94 (m, 1H), 7.02 (ddd, 1H, J=9.6, 7.6, 2.0 Hz), 7.10 (ddd, 1H, J=16.4, 10.0, 8.4 Hz)

LC/MS (98%) ESI+ Calcd: 349.4; Found: 350.9 (M+1)

EXAMPLE 36

Preparation of A51

Synthesis of 5-Nitro-4H-benzo[1,4]oxazin-3-one, K-64. A mixture of 2-amino-3-nitrophenol (1.54 g, 10 mmol), ethyl bromoacetate (1.67 g, 10 mmol), potassium carbonate (1.54 g, 11 mmol) and DMF (5.0 mL) was stirred at room temperature for 20 h. Reaction mixture was diluted with water (100 mL) and extracted with ethyl acetate (100 mL×3). Combined ethyl acetate layers were washed with water (50 mL×2), dried (brine, sodium sulphate), concentrated and dried on high vacuum to give 5-Nitro-4H-benzo[1,4]oxazin-3-one, K-64 (1.6 g).

Synthesis of 4-Naphthalen-2-ylmethyl-5-nitro-4H-benzo[1,4]oxazin-3-one, K-65. Sodium hydride (94 mg, 3.0 mmol), was added in portions to a solution of 5-Nitro-4H-benzo[1,4]oxazin-3-one, K-64 (388 mg, 2 mmol) in DMF. After 30 minutes, 2-bromomethyl naphthalene (442 mg, 2 mmol) added and stirred at room temperature for 20 h. Reaction mixture was diluted with water (100 mL) and extracted with ethyl acetate (100 mL×3). Combined ethyl acetate layers were washed with water (50 mL×2), dried (brine, sodium sulphate), concentrated and dried on high vacuum to give 4-Naphthalen-2-ylmethyl-5-nitro-4H-benzo[1,4]oxazin-3-one, K-65 (653 mg).

Synthesis of 5-Amino-4-naphthalen-2-ylmethyl-4H-benzo[1,4]oxazin-3-one, K-66. A solution of 4-nphthalen-2-ylmethyl-5-nitro-4H-benzo[1,4]oxazin-3-one, K-65 (0.65 g) in methanol (30 mL) and dioxane (7.0 mL) was hydrogenated in presence of 10% Pd-C at 45 psi for 22 h. Reaction mixture was filtered and the filtrate was concentrated to give 5-Amino-4-naphthalen-2-ylmethyl-4H-benzo[1,4]oxazin-3-one, K-66 (620 mg).

Synthesis of N-(4-Naphthalen-2-ylmethyl-3-oxo-3,4-dihydro-2H-benzo[1,4]oxazin-5-yl)-oxalamic acid methyl ester, K-67. To a solution of 5-Amino-4-naphthalen-2-ylmethyl-4H-benzo[1,4]oxazin-3-one, I-66 (120 mg, 04 mmol) and ethyl glyoxylylchloride (52 mg, 0.4 mmol) in THF (3.0 mL), triethyl amine (0.1 mL, 1.0 mmol) was added drop wise at room temperature and stirred for 18 h. Reaction mixture was concentrated and the residue was purified over silica gel with chloroform: methanol (97:3) as eluent to afford N-(4-Naphthalen-2-ylmethyl-3-oxo-3,4-dihydro-2H-benzo[1,4]oxazin-5-yl)-oxalamic acid methyl ester, K-67 (102 mg).

Synthesis of N-(4-Naphthalen-2-ylmethyl-3-oxo-3,4-dihydro-2H-benzo[1,4]oxazin-5-yl)-oxalamic acid, A51. To a suspension of N-(4-Naphthalen-2-ylmethyl-3-oxo-3,4-dihydro-2H-benzo[1,4]oxazin-5-yl)-oxalamic acid methyl ester, K-67 (95 mg,) in methanol (2.0 mL), 1.0 M NaOH (0.5 mL) was added followed by THF (2.0 mL) resulting in a clear solution. Reaction was stirred at room temperature for 30 minutes and then concentrated to remove the solvents. The residue was taken in water (2.0 mL), acidified with 1.0 M HCl and extracted with ethyl acetate (5.0 mL×4). Combined extracts were washed with water (5.0 mL), dried (brine, $Na_2SO_4$) and concentrated to afford N-(4-Naphthalen-2-ylmethyl-3-oxo-3,4-dihydro-2H-benzo [1,4]oxazin-5-yl)-oxalamic acid, A51 (69 mg). 1H NMR (CDCl3) 4.66 (s, 2H), 5.21 (s, 2H), 7.02 (m, 2H), 7.07 (d, J=8.5 Hz, 1H), 7.14 (br s, 1H), 7.33 (br s, 2H), 7.50 (s, 1H), 7.65 (m, 3H), 8.69 (s, 1H). MS (ESI−) Calcd. for: 376.4; Found: 375.5 (M−H).

EXAMPLE 37

Preparation of A04

Synthesis of 2-Amino-benzene-1,3-diol, K-68. A mixture of 2-nitrobenzene-1,3-diol (3.1 g, 20 mmole) and 1 g of Pd/C (5%) in methanol (100 ml) was hydrogenated at 30 psi of $H_2$ at rt for 2 days. The reaction mixture was filtered with celite and the celite was washed with ethanol, water and methanol. After removal of solvent under vacuum, 2.6 g of compound K-68 was obtained as white solid. $^1$H-NMR (500 MHz, DMSO-$d_6$).

Synthesis of 2-[(Naphthalen-2-ylmethyl)-amino]-benzene-1,3-diol, K-69. A mixture of compound K-68 (250 mg, 2 mmole) and 2-naphthaldehyde (343 mg, 2.2 mmole) in methanol (20 ml) was stirred at rt for 2 hrs and then cooled to −10° C. NaBH$_4$ (304 mg, 8 mmole) was slowly added to reaction mixture at −10 to 0° C. After stirring at 0° C. for 30 min and rt for 2 hrs, the reaction mixture was cooled to 0° C. and quenched with water. The reaction mixture was adjusted to pH ~4 and extracted with ethyl acetate (2×100 ml). Sodium chloride was added to water layer, and extracted with dichloromethane. Solid was formed from water/DCM. Solid was filtered and washed with water and DCM to give 140 mg of compound K-69. $^1$H-NMR (500 MHz, DMSO-$d_6$).

Synthesis of 4-Hydroxy-3-naphthalen-2-ylmethyl-3H-benzooxazol-2-one, K-70. A mixture of compound K-69 (140 mg, 0.46 mmole), triethylamine (46 mg, 0.46 mmole) and 1,1'-carbonyldiimidazole (80 mg, 0.5 mmole) in THF (20 ml) was refluxed over night and then partitioned between ethyl acetate and water. Water layer was extracted with ethyl acetate. The combined organic phase was washed with diluted HCl aq., water, brine and dried over sodium sulfate. After removal of solvent, 140 mg of compound K-70 was obtained as a white solid. $^1$H-NMR (500 MHz, DMSO-$d_6$). $^{13}$C-NMR (125 MHz, DMSO-$d_6$).

Synthesis of (3-Naphthalen-2-ylmethyl-2-oxo-2,3-dihydro-benzooxazol-4-yloxy)-acetic acid tert-butyl ester, K-71. A mixture of compound K-70 (140 mg, 0.48 mmole), tert-butyl bromoacetate (136 mg, 0.7 mmole) and K2CO3 (95 mg, 0.7 mmole) in acetone (10 ml) and DMF (5 ml) was stirred at rt over night and then partitioned between ethyl acetate and water. Water layer was extracted with ethyl acetate. The combined organic phase was washed with water, brine and dried over sodium sulfate. After removal of solvent, 160 mg of compound K-71 was obtained. 1H-NMR (500 MHz, CDCl3).

Synthesis of (3-Naphthalen-2-ylmethyl-2-oxo-2,3-dihydro-benzooxazol-4-yloxy)-acetic acid, A04. To a solution of compound K-71 (150 mg, 0.37 mmole) in dichloromethane (5 ml), TFA (10 ml) was added at rt The reaction mixture was stirred at rt for 2 hrs and solvent was removed under vacuum. The residue was washed with ether to give 130 mg of compound A04. 1H NMR (DMSO-d6) 4.48 (s, 2H), 5.37 (s, 2H), 6.89 (dd, J=8 and 1 Hz, 1H), 7.03 (dd, J=8 and I Hz, 1H), 7.07 (dd, J=8 and 8 Hz, 1H), 7.50 (d, J=10 Hz, 1H), 7.50 (m, 1H), 7.57 (dd, J=8 and 2 Hz, 1H), 7.88 (m, 1H), 7.98 (s, 1H), 13.3 (bs, 1H).

LC/MS (100%) ESI− Calcd. 348.3 m/z Found: 348.2 m/z

EXAMPLE 38

Preparation of A05

Synthesis of 4-Hydroxy-3H-benzooxazol-2-one, K-72. A mixture of 2-amino-benzene-1,3-diol (K-68, 2.03 g, 16.2 mmole) and 1,1'-carbonyldiimidazole (2.63 g, 16.2 mmole) in THF (200 ml) was refluxed over night. After removal of THF under vacuum, residue was dissolved in ethyl acetate and washed with diluted HCl aq., water, brine and dried over sodium sulfate. After removal of solvent, solid was washed with ether to give 1.9 g of compound K-72. $^1$H-NMR (500 MHz, DMSO-$d_6$).

Synthesis of Carbonic acid tert-butyl ester 2-oxo-2,3-dihydro-benzooxazol-4-yl ester, K-73. To a solution of compound K-72 (1 g, 6.6 mmole) in THF (20 ml), water (8 ml) and NaOH aq. (2N, 13 ml), di-tert-butyl dicarbonate (3.16 g, 14.5 mmole) in THF (15 ml) was added at rt. After stirring at rt over night, reaction mixture was diluted with water and ethyl acetate and cooled with ice, and then adjusting pH to about 2-3 by addition of HCl aq. (2N). Water layer was extracted with ethyl acetate (2×100 ml). The combined organic phase was washed with water, brine and dried over sodium sulfate. After removal of solvent, 2.3 g of compound K-73 was obtained. $^1$H-NMR (500 MHz, DMSO-$d_6$).

Synthesis of 3-Benzo[1,3]dioxol-5-ylmethyl-4-hydroxy-3H-benzooxazol-2-one, K-74. A mixture of compound K-73 (251 mg, 1 mmole), 3,4-methylenedioxy benzyl chloride (255 mg, 1.5 mmole), K2CO3 (207 mg, 1.5 mmole) and KI (249 mg, 1.5 mmole) in acetone (10 ml) and water (5 drops) was stirred at rt over night and then partitioned between ethyl acetate and water. Water layer was extracted with ethyl acetate. The combined organic phase was washed with water, brine and dried over sodium sulfate. After removal of solvent, the intermediate O-BOC compound (carbonic acid 3-benzo [1,3]dioxol-5-ylmethyl-2-oxo-2,3-dihydro-benzooxazol-4-yl ester tert-butyl ester) was dissolved in dichloromethane (6 ml), and then TFA (3 ml) was added at rt The reaction mixture was stirred at rt for 15 min and solvent was removed under vacuum. The residue was washed with ether to give 100 mg of compound K-74. $^1$H-NMR (500 MHz, DMSO-$d_6$).

Synthesis of (3-Benzo[1,3]dioxol-5-ylmethyl-2-oxo-2,3-dihydro-benzooxazol-4-yloxy)-acetic acid tert-butyl ester, K-75. A mixture of compound K-74 (100 mg, 0.35 mmole), tert-butyl bromoacetate (136 mg, 0.7 mmole) and K2CO3 (95 mg, 0.7 mmole) in acetone (8 ml) and DMSO (2 ml) was stirred at rt over night and then partitioned between ethyl acetate and water. Water layer was extracted with ethyl acetate. The combined organic phase was washed with water, brine and dried over sodium sulfate. After removal of solvent, 100 mg of compound K-75 was obtained. $^1$H-NMR (500 MHz, CDCl$_3$).

Synthesis of (3-Benzo[1,3]dioxol-5-ylmethyl-2-oxo-2,3-dihydro-benzooxazol-4-yloxy)-acetic acid, A05. To a solution of compound K-75 (100 mg, 0.25 mmole) in dichloromethane (4 ml), TFA (8 ml) was added at rt The reaction mixture was stirred at rt for 3 hrs and solvent was removed under vacuum. The residue was washed with ether to give 80 mg of compound A05. 1H NMR (DMSO-d6) 4.85 (s, 2H), 5.10 (s, 2H), 5.97 (s, 2H), 6.84 (d, J=8 Hz, 1H), 6.89 (d, J=8 Hz, 1H), 6.95 (dd, J=8 and 8 Hz, 1H), 7.00 (d, J=8 Hz, 1H), 7.06(m, 2H), 13.2 (bs, 1H).

LC/MS (90%) ESI– Calcd. 342.2 m/z Found: 342.2 m/z

EXAMPLE 39

Preparation of A06

Synthesis of 3-(3,4-Dichloro-benzyl)-4-hydroxy-3H-benzooxazol-2-one, K-76. A mixture of compound K-73 (251 mg, 1 mmole), 3,4-dichlorobenzyl chloride (292 mg, 1.5 mmole), K2CO3 (207 mg, 1.5 mmole) and KI (249 mg, 1.5 mmole) in acetone (10 ml) and water (5 drops) was stirred at rt over night and then partitioned between ethyl acetate and water. Water layer was extracted with ethyl acetate. The combined organic phase was washed with water, brine and dried over sodium sulfate. After removal of solvent, the O-BOC prodcut (Carbonic acid tert-butyl ester 3-(3,4-dichloro-benzyl)-2-oxo-2,3-dihydro-benzooxazol-4-yl ester) was dissolved in dichloromethane (6 ml), and then TFA (3 ml) was added at rt The reaction mixture was stirred at rt for 15 min and solvent was removed under vacuum. The residue was washed with ether to give 80 mg of compound K-76. $^1$H-NMR (500 MHz, DMSO-d$_6$).

Synthesis of [3-(3,4-Dichloro-benzyl)-2-oxo-2,3-dihydro-benzooxazol-4-yloxy]-acetic acid tert-butyl ester, K-77. A mixture of compound K-76 (80 mg, 0.26 mmole), tert-butyl bromoacetate (136 mg, 0.7 mmole) and K2CO3 (95 mg, 0.7 mmole) in acetone (8 ml) and DMSO (2 ml) was stirred at rt over night and then partitioned between ethyl acetate and water. Water layer was extracted with ethyl acetate. The combined organic phase was washed with water, brine and dried over sodium sulfate. After removal of solvent, 90 mg of compound K-77 was obtained. $^1$H-NMR (500 MHz, CDCl$_3$)

Synthesis of [3-(3,4-Dichloro-benzyl)-2-oxo-2,3-dihydro-benzooxazol-4-yloxy]-acetic acid, A06. To a solution of compound K-77 (90 mg, 0.21 mmole) in dichloromethane (4 ml), TFA (8 ml) was added at rt The reaction mixture was stirred at rt for 3 hrs and solvent was removed under vacuum. The residue was washed with ether to give 70 mg of acid A06. 1H NMR (DMSO-d6) 4.82 (s, 2H), 5.20 (s, 2H), 6.90 (dd, J=8 and 1 Hz, 1H), 7.02 (dd, J=8 and 1 Hz, 1H), 7.07 (dd, J=8, 8 Hz, 1H), 7.40 (dd, J=8,2 Hz, 1H), 7.60 (d, J=8 Hz, 1H), 7.74 (d, J=2 Hz, 1H), 13.2 (bs, 1H).

LC/MS (90%) ESI– Calcd. 367.2 m/z Found: 367.9 m/z

EXAMPLE 40

Preparation of A07

Synthesis of 3-(2,4-Dichloro-benzyl)-4-hydroxy-3H-benzooxazol-2-one, K-78. A mixture of compound K-73 (251 mg, 1 mmole), 2,4-dichlorobenzyl chloride (292 mg, 1.5 mmole), K2CO3 (207 mg, 1.5 mmole) and KI (249 mg, 1.5 mmole) in acetone (10 ml) and water (5 drops) was stirred at rt over night and then partitioned between ethyl acetate and water. Water layer was extracted with ethyl acetate. The combined organic phase was washed with water, brine and dried over sodium sulfate. After removal of solvent, the O-BOC derivative (carbonic acid tert-butyl ester 3-(2,4-dichloro-benzyl)-2-oxo-2,3-dihydro-benzooxazol-4-yl ester), was dissolved in dichloromethane (6 ml), and then TFA (3 ml) was added at rt The reaction mixture was stirred at rt for 15 min and solvent was removed under vacuum. The residue was washed with ether to give 110 mg of compound K-78. $^1$H-NMR (500 MHz, DMSO-d$_6$).

Synthesis of 3-(2,4-Dichloro-benzyl)-2-oxo-2,3-dihydro-benzooxazol-4-yloxy]-acetic acid tert-butyl ester, K-79. A mixture of compound K-78 (80 mg, 0.26 mmole), tert-butyl bromoacetate (136 mg, 0.7 mmole) and K2CO3 (95 mg, 0.7 mmole) in acetone (8 ml) and DMSO (2 ml) was stirred at rt over night and then partitioned between ethyl acetate and water. Water layer was extracted with ethyl acetate. The combined organic phase was washed with water, brine and dried over sodium sulfate. After removal of solvent, 140 mg of compound K-79 was obtained. $^1$H-NMR (500 MHz, CDCl$_3$).

Synthesis of 3-(2,4-Dichloro-benzyl)-2-oxo-2,3-dihydro-benzooxazol-4-yloxy]-acetic acid, A07. To a solution of compound K-79 (90 mg, 0.33 mmole) in dichloromethane (4 ml), TFA (8 ml) was added at rt The reaction mixture was stirred at rt for 3 hrs and solvent was removed under vacuum. The residue was washed with ether to give 105 mg of compound A07. 1H NMR (DMSO-d6) 4.67 (s, 2H), 5.27 (s, 2H), 6.89 (dd, J=8 and 2 Hz, 1H), 7.08 (m, 2H), 7.16 (d, J=8 Hz, 1H), 7.35 (dd, J=8 and 2 Hz, 1H), 7.66 (d, J=2 Hz, 1H), 13.1 (s, 1H). LC/MS (90%) ESI– Calcd. 367.2 m/z Found: 366.2 m/z

EXAMPLE 41

Preparation of A08

Synthesis of 3-(2,5-Dimethyl-benzyl)-4-hydroxy-3H-benzooxazol-2-one, K-80. A mixture of compound K-73 (251 mg, 1 mmole), 2,5-dimethylbenzyl chloride (233 mg, 1.5 mmole), K2CO3 (207 mg, 1.5 mmole) and KI (249 mg, 1.5 mmole) in acetone (10 ml) and water (5 drops) was stirred at rt over night and then partitioned between ethyl acetate and water. Water layer was extracted with ethyl acetate. The combined organic phase was washed with water, brine and dried over sodium sulfate. After removal of solvent, the O-BOC derivative (Carbonic acid tert-butyl ester 3-(2,5-dimethyl-benzyl)-2-oxo-2,3-dihydro-benzooxazol-4-yl ester), was dissolved in dichloromethane (6 ml), and then TFA (3 ml) was added at rt The reaction mixture was stirred at rt for 15 min and solvent was removed under vacuum. The residue was washed with ether to give 110 mg of compound K-80.

Synthesis of 3-(2,5-Dimethyl-benzyl)-2-oxo-2,3-dihydro-benzooxazol-4-yloxy]-acetic acid tert-butyl ester, K-81. A mixture of compound K-80 (110 mg, 0.4 mmole), tert-butyl bromoacetate (136 mg, 0.7 mmole) and K2CO3 (95 mg, 0.7 mmole) in acetone (8 ml) and DMSO (2 ml) was stirred at rt over night and then partitioned between ethyl acetate and water. Water layer was extracted with ethyl acetate. The combined organic phase was washed with water, brine and dried over sodium sulfate. After removal of solvent, 150 mg of compound K-81 was obtained. $^1$H-NMR (500 MHz, CDCl$_3$).

Synthesis of [3-(2,5-Dimethyl-benzyl)-2-oxo-2,3-dihydro-benzooxazol-4-yloxy]-acetic acid, A08. To a solution of compound K-81 (150 mg, 0.39 mmole) in dichloromethane (4 ml), TFA (8 ml) was added at rt The reaction mixture was stirred at rt for 3 hrs and solvent was removed under vacuum. The residue was washed with ether to give 120 mg of compound A08. 1H NMR (DMSO-d6) 2.15 (s, 3H), 2.31 (s, 3H), 4.68 (s, 2H), 5.19 (s, 2H), 6.74 (s, 1H), 6.88 (dd, J=8 and 2 Hz, 1H), 6.95 (d, J=8 Hz, 1H), 7.08 (m, 3H), 13.1 (bs, 1H).

LC/MS (90%) ESI– Calcd. 326.3 m/z Found: 326.4 m/z

EXAMPLE 42

Preparation of A09

Preparation of 7-bromo-3-methyl-1H-indole (K-82). 2-Bromo nitrobenzene was reacted with allyl magnesium bromide according to the literature procedure (Dobbs A. J. Org Chem. 2001, 66, 638-641), to provide 7-bromo-3-methyl-1H-indole (K-82).

Preparation of (E)-3-(3-methyl-1H-indol-7-yl)-acrylic acid methyl ester (K-83). To a mixture of compound K-82 (300 mg, 1.42 mmole) and methyl acrylate (183 mg, 2.13 mmole) in triethylamine (1 ml), palladium(II) acetate (31 mg, 0.14 mmole) and tri-o-tolylphosphine (129 mg, 0.42 mmole) were added under argon at rt The reaction mixture was stirred at 100° C. for 4 hrs in a sealed pressure tube and then cooled to rt. The reaction mixture was diluted with methylene chloride (50 ml), washed with water (3×30 ml), brine, and dried over sodium sulfate. After removal of solvent, the residue was purified by column chromatography on silica gel with ethyl acetate/hexane as an eluent to give 250 mg of compound K-83 as a yellow solid. 1H-NMR (500 MHz, CDCl3) MS(ESI−). 214.5 (M−1).

Synthesis of (E)-3-[1-(2,4-Dichloro-benzyl)-3-methyl-1H-indol-7-yl]-acrylic acid methyl ester, (K-84). To a solution of the methyl ester (K-83) (730 mg, 3.4 mmole) in DMF (15 ml), was added NaH (60% in oil, 272 mg, 6.8 mmole) at 0° C. After stirring at rt for 30 min, 2,4-dichlorobenzyl chloride (1326 mg, 6.8 mmole) was added. The reaction mixture was stirred at rt over night and then diluted with methylene chloride (150 ml). The reaction mixture was washed with dilute aqueous HCl (2×50 ml), water (4×100 ml), brine and dried over sodium sulfate. After filtration and removal of solvent, the residue was purified by column chromatography on silica gel with hexane and ethyl acetate/hexane as an eluent to give 60 mg of the methyl ester, K-84 and 470 mg of the ester K-85 (3-[1-(2,4-Dichloro-benzyl)-3-methyl-1H-indol-7-yl]-acrylic acid 2,4-dichloro-benzyl ester). 1H-NMR (500 MHz, DMSO-d6).

Synthesis of (E)-3-[1-(2,4-Dichloro-benzyl)-3-methyl-1H-indol-7-yl]-acrylic acid, A09. To a solution of ester K-84 (300 mg, 0.8 mmole) in THF (6 ml) and methanol (6 ml), was added aqueous 2N NaOH (3 ml) at rt. The reaction mixture was stirred at rt over night and then the pH was made acidic by adding aqueous 2N HCl. The reaction mixture was extracted with ethyl acetate (2×40 ml). The combined organic phase was washed with water, brine and dried over sodium sulfate. After filtration and removal of the solvent, the residue was washed with ether to give 280 mg of acid A09. 1H NMR (CDCl3) 2.36 (s, 3H), 5.48 (s, 2H), 6.24 (d, J=15 Hz, 1H), 6.35 (d, J=8 Hz, 1H), 6.78 (s, 1H), 7.06 (dd, J=8.2 Hz, 1H), 7.16 (dd, J=8, 8 Hz, 1H), 7.34 (d, J=8 Hz, 1H), 7.49 (d, J=2 Hz, 1H), 7.67 (d, J=8 Hz, 1H), 7.96 (d, J=15 Hz, 1H), 11-12 (b, 1H). LC/MS (100%) ESI− Calcd. 360.2 m/z Found: 360.2 m/z

EXAMPLE 45

Preparation of A53

Synthesis of Indole-7 carboxyldehyde (K-87). Ethyl Indole-7-carboxylate was prepared according to literature procedure {Batcho B. and Leimgruber, K., Org. Syn. Vol IIV, page 34-40). To a solution of methyl 7-indolecarboxylate (13 g, 74.2 mmol) in 250 ml of anhydrous THF was added LiAlH$_4$ (10.9 g, 0.288 mol) in portions, and reaction mixture was heated to reflux for 2 h. After cooling to room temperature, the excess hydride was quenched by addition of water (12 mL), 15% NaOH (12 mL) and water (26 mL). The solids were removed by filtration through a pad of Celite and filtrate was evaporated in vacuo to yield (1H-indol-7-yl)-methanol (10.7 g, 98%). $^1$HNMR (CDCl$_3$). To a solution of the alcohol, (1H-indol-7-yl)-methanol (8.0 g, 54.3 mmol) in 400 mL of methylene chloride was added activated manganese (IV) oxide (85%, 41.0 g, 0.40 mol), and stirred at ambient temperature for 72 h. After additional of 200 mL of methylene chloride and 400 mL of methanol to the reaction mixture, the whole mixture was filtered through a pad of silica gel to remove solid materials. The filtrate was concentrated to afford a crude product, which was purified by a column chromatography on silica gel to yield 1H-indole-7-carbaldehyde, K-87 (6.55 g, 83%). $^1$HNMR (CDCl$_3$).

3-(1H-Indol-7-yl)-acrylic acid ethyl ester (K-88). To a round bottom flask (100 mL) which contained a suspension of NaH (60% in mineral oil, 320 mg, 8 mmol) in THF (20 mL) was added triethylphosphonoacetate (1.5 g, 6.6 mmol) at 0° C. The mixture which resulted was allowed to warm to rt and stir for 2 h and then cooled to 0° C. To this solution, indole-7-carboxaldehyde K-87 (450 mg, 3 mmol) was added at 0° C. The reaction mixture that resulted was allowed to warm to rt and stir for 2 h, then heated to 78° C. and stirred at 78° C. for 14 h. The reaction mixture was cooled to 5° C. and was quenched with the addition of aq NH$_4$Cl (saturated, 15 mL) followed by extraction of EtOAc (3×30 mL). The combined organic layers were washed with brine (2×20 mL), dried (Na$_2$SO$_4$) and the solvent was removed under reduced pressure. The residue was purified by flash chromatography (silica gel, EtOAc/hexane=1:20-1:8) to afford desired 3-(1H-indol-7-yl)-acrylic acid ethyl ester K-88 (450 mg, 68%) as a white solid. MS(ESI−)m/z(216.3, 100%). 1H NMR (CDCl3), 13C NMR (CDCl3).

Synthesis of 3-(1H-Indol-7-yl)-acrylic acid (K-89) To a round bottom flask (500 mL) which contained a solution of NaOH (1.2 g, 30 mmol) in EtOH (100 mL) and H$_2$O (30 mL) was added 3-(1H-Indol-7-yl)-acrylic acid ethyl ester K-88 (3.2 g, 15 mmol) at 5° C. The resulted mixture was allowed to warm to rt and stir for 10 min, then heated to 78° C. and stirred for 4 h. The reaction mixture was cooled to 5° C. and was acidified with addition of aq HCl (10%) until pH=1, which was followed by extraction with CH$_2$Cl$_2$/MeOH (95/5, 3 ×150 mL). The combined organic layers were washed with brine (2×20 mL), dried (Na$_2$SO$_4$) and the solvent was removed under reduced pressure to provide the crude product, which was purified by recrystallization from acetone/EtOAc/hexane to yield desired 3-(1H-indol-7-yl)-acrylic acid K-89 (2.4 g, 86%) as a white solid. MS(APCI−)m/z (186.2, 100%). LCMS(APCI−)>95%.

Synthesis of (E)-3-(1-Naphthalen-2-ylmethyl-1H-indol-7-yl)-acrylic acid, A53. To a suspension of NaH (60% in mineral oil, 360 mg, 9.0 mmol) in DMF (30 mL) was added 3-(1H-Indol-7-yl)-acrylic acid, K-89 (560 mg, 3.0 mmol) at 0° C. The resulting mixture was allowed to warm to rt and stir for 2 h and then recooled to 0° C. To this solution, 2-bromomethylnaphthalene (680 mg, 3.1 mmol) was added at 0° C. and the resulting reaction mixture was allowed to warm to rt and stir for 16 h, The reaction mixture was cooled to 5° C. and was acidified through the addition of aqueous 10% HCl until a pH of 1 was reached. This mixture was extracted with CH2Cl2/MeOH (9/1, 3×50 mL). The combined organic extracts were dried (Na2SO4), filtered and the solvent was removed under reduced pressure to provide the crude product which was purified by flash chromatography (silica gel, CH2Cl2:/EtOAc/hexane,=1:8-1:2) to afford desired acrylic acid, A53 (400 mg, 41%) as a white solid. 1H NMR (500 MHz, DMSO-

EXAMPLE 46

Preparation of A18

Synthesis of (E)-3-[1-(2,4-Dichloro-benzyl)-2-oxo-2,3-dihydro-1H-indol-7-yl]-acrylic acid, A18. To a pressure-resistant flask (350 mL) which contained A17 (430 mg, 1.2 mmol) was added $NH_2NH_2 \cdot H_2O$ (20 mL) at rt. The mixture which resulted was sealed, heated to 130° C. and stirred at 130° C. for 1 h, then was cooled to 0° C. After the addition ice-water (300 mL), the reaction mixture was acidified with addition of aq HCl (10%) until pH=1 and stirred at rt for 30 min. The solid which formed was filtered out, washed with water (3×50 mL) and dried over vacuum at 50° C. to afford desired oxyindole derivative, A18 (300 mg, 73%) as a white solid. 1H NMR (400 MHz, acetone-d6) 3.61 (s, 2H), 5.01 (s, 2H), 6.04 (d, J=15.2 Hz, 1H), 6.96-7.01 (m, 3H), 7.16 (m, 1H), 7.27-7.31 (m, 2H), 7.42 (d, J=15.6 Hz, 1H), 7.42 (s, 1H), LC/MS (>70%) ESI– Calcd: 362.2; Found: 360.1 (M–2).

EXAMPLE 47

Preparation of A19

Synthesis of (E)-3-[1-(2,4-Dichloro-benzyl)-2-oxo-2,3-dihydro-1H-indol-7-yl]-acrylic acid methyl ester, K-90. To a pressure-resistant flask (50 mL) which contained a stirring suspension of A18** (100 mg, 0.3 mmol) in MeOH (15 mL) was added conc. HCl (0.5 mL) at rt. The reaction mixture which resulted was sealed, heated to 85° C, stirred at 85° C. for 5 h, cooled to 0° C., neutralized with the addition of aq $NH_4Cl$ (Sat., 2 mL), diluted with water (30 mL) and extracted with EtOAc (3×20 mL). The combined organic layers were washed with water (2×20 mL), dried ($Na_2SO_4$) and the solvent was removed under reduced pressure to provide K-90 (103 mg, 99%) as a white solid. MS (ESI–): (374.2, M–2). $^1$H-NMR (500 MHz, $CDCl_3$).

Synthesis of (E)-3-[1-(2,4-Dichloro-benzyl)-3,3-dimethyl-2-oxo-2,3-dihydro-1H-indol-7-yl]-acrylic acid methyl ester, K-91. To a RBF (20 mL) which contained a stirring suspension of K-90 (45 mg, 0.12 mmol) and $K_2CO_3$ (45 mg) in DMF (2 mL) was added methyl iodide (0.5 mL, excess) at 0° C. The reaction mixture which resulted was allowed to warm to rt and stir at rt for 3 d. The mixture was poured into 30 mL stirring ice-water solution and extracted with EtOAc (3×20 mL). The combined organic layers were washed with water (2×20 mL), dried ($Na_2SO_4$) and the solvent was removed under reduced pressure to provide the crude 25 which was purified by flash chromatography (silica gel, $CH_2Cl_2$; EtOAc/hexane=1:5) to afford desired product K-91 (35 mg, 75%) as a white solid. MS (APCI–): (404.2, M). $^1$H-NMR (500 MHz, $CDCl_3$).

(E)-3-[1-(2,4-Dichloro-benzyl)-3,3-dimethyl-2-oxo-2,3-dihydro-1H-indol-7-yl]-acrylic acid, A19. To a round bottom flask (50 mL) which contained a solution of NaOH (25 mg, 0.6 mmol) in MeOH (5 mL) and $H_2O$ (5 mL) was added K-91 (25 mg, 0.05 mmol) at 5° C. The reaction mixture which resulted was allowed to warm to rt and stir at rt for 16 h. The reaction mixture was cooled to 0° C. and was acidified with addition of aq HCl (10%) until pH=1, which was followed by addition of water (10 mL) and then extracted with dichloromethane (3×20 mL). The combined organic layers was dried over $Na_2SO_4$ and the solvent was removed under vacuo to afford crude A19 (20 mg, 80% yield) as an off-white solid. 1H NMR (500 MHz, acetone-d6) 1.33 (s, 6H), 5.03 (s, 2H), 6.05 (d, J=15.0 Hz, 1H), 6.89 (d, J=8.5 Hz, 1H), 7.03 (t, J=7.5 Hz, 1H), 7.19 (dd, J=8.5 Hz, 2.0 Hz, 1H), 7.30 (d, J=7.5 Hz, 1H), 7.35 (d, J=7.0 Hz, 1H), 7.42-7.45 (m, 2H).

MS: ESI+ Calcd: 390.26; Found: 390.4 (M).

EXAMPLE 48

Preparation of A20

Synthesis of (E)-3-[1-(2,4-Dichloro-benzyl)-3,3-difluoro-2-oxo-2,3-dihydro-1H-indol-7-yl]-acrylic acid methyl ester, K-92. To a round bottom flask (25 mL) which contained a solution of K-26 (200 mg, 0.5 mmol) in $CH_2Cl_2$ (8 mL) was added diethylaminosulfur trifluoride (DAST, 0.5 mL, excess) at 5° C. The reaction mixture which resulted was allowed to warm to rt and stir for 3 d, then was cooled to 5° C. The reaction was quenched with the addition of MeOH (1 mL) at 0° C. and was stirred at 0° C. for 20 min, then at rt for 10 min. The reaction vessel was cooled to 5° C. and water (10 mL) was added at 5° C. and the mixture which resulted was allowed to warm to rt and stir at rt for 30 min which was followed extracted with dichloromethane (2×30 mL). The combined organic layers was washed with water (2×20 mL), dried over $Na_2SO_4$ and the solvent was removed under vacuo to afford crude K-92 (200 mg, 95%) as a light yellow solid which was directly used for next step. MS (APCI–): (410.3, M–2). $^1$H-NMR (400 MHz, $CDCl_3$).

Synthesis of (E)-3-[1-(2,4-Dichloro-benzyl)-3,3-difluoro-2-oxo-2,3-dihydro-1H-indol-7-yl]-acrylic acid, A20. To a round bottom flask (50 mL) which contained a solution of NaOH (120 mg, 3 mmol) in MeOH (7.5 mL) and $H_2O$ (7.5 mL) was added K-92 (120 mg, 0.3 mmol) at 5° C. The reaction mixture which resulted was allowed to warm to rt and stir at rt for 2 h, then heated to 50° C. and stirred at 50° C. for 2 h. The reaction mixture was cooled to 0° C. and was acidified with addition of aq HCl (10%) until pH=1, which was followed by addition of water (50 mL) and then extracted with dichloromethane-MeOH (10:1, 5×30 mL). The combined organic layers was dried over $Na_2SO_4$ and the solvent was removed under vacuo to afford crude which was purified by recrystallization with acetone/EA/Hex to afford desired acid A20 (90 mg, 75% yield) as off-white solid. 1H NMR (500 MHz, DMSO-d6) 5.07 (s, 2H), 6.21 (d, J=15.0 Hz, 1H), 7.09 (d, J=8.5 Hz, 1H), 7.30-7.33 (m, 2H), 7.39 (dd, J=8.5, 1.5 Hz, 1H), 7.68 (d, J=2.0Hz, 1H), 7.73 (d, J=8.0 Hz, 1H), 7.85 ((d, J=7.5 Hz, 1H)), 12.40 (s, 1H), LC/MS (97%) ESI– Calcd: 398.2; Found: 398.0 (M).

EXAMPLE 49

Preparation of A16

Synthesis of A16. To a round bottom flask (200 mL) which contained a solution of NaOH (500 mg, 12 mmol) in MeOH (40 mL) and $H_2O$ (40 mL) was added K-25 (450 mg, 10.3 mmol) at 5° C. The reaction mixture which resulted was allowed to warm to rt and stir for 10 min, heated and stirred at 50° C. for 2 h and then at 75° C. for 2 h. The reaction mixture was cooled to 0° C. and was acidified with addition of aq HCl (2N) until pH=1, which was followed by addition of water (150 mL). The solid which formed was filtered out, washed with water (3×60 mL) and dried over vacuum at 50° C. to provide the desired A16 (430 mg, 95%) as an off-white solid. 1H NMR (500 MHz, acetone-d6) 5.28-5.31 (m, 2H), 5.39-5.41 (m, 2H), 6.00 (s, 2H), 7.08 (d, J=15.0 Hz, 1H), 7.82 (d, J=8.0 Hz, 1H), 8.11 (t, J=7.5 Hz, 1H), 8.28 (dd, J=8.5, 1.5 Hz, 1H), 8.39 (d, J=15.5 Hz, 1H), 8.42 (dd, J=7.5 Hz, J=1.5 Hz, 1H), 8.45-8.47 (m, 2H). LC/MS (90%) ESI– Calcd: 420.2; Found: 418 (M–2).

EXAMPLE 50

Preparation of A55

Synthesis of 3-(3-Dimethylaminomethyl-1-naphthalen-2-ylmethyl-1H-indol-7-yl)-propionic acid, A55. To a stirring solution of diethylamine (20 mg, 0.3 mmol), acetic acid (glacial, 30 uL) in methanol (5 mL) and water (1 mL) was added paraformaldehyde (Aldrich, 95%, 8 mg, 0.3 mmol) and intermediate A53 (33 mg, 0.1 mmol) at 0° C. The reaction mixture which resulted was allowed to heat to 70° C. and stir at 70° C. for 4 h, then was cooled to 5° C. and was acidified with addition of aq HCl (10%) until pH=1, which was followed by extraction of CH$_2$Cl$_2$/MeOH (9/1, 3×10 mL). The combined organic layers were dried (Na$_2$SO$_4$) and the solvent was removed under reduced pressure to provide the crude product which was purified by recrystallization from acetone/EtOAc/Hexane to afford desired compound A55 (20.3 mg, 53%) as a light yellow solid. 1H NMR (500 MHz, MeOH-d4): 2.92 (s, 6H), 4.58 (s, 2H), 5.81 (s, 2H), 6.19 (d, J=15.5 Hz, 1H), 7.16-7.26 (m, 2H), 7.37-7.46 (m, 4H), 7.5 (s, 1H), 7.66-7.70 (m, 1H), 7.74 (s, 1H), 7.79-7.87 (m, 2H), 8.28 (d, J=15.5 Hz, 1H), LCMS(APCI$^-$): (>75%) Calcd: 384.5; Found: 383.1 (M–1).

EXAMPLE 51

Preparation of A56

Synthesis of K-93. Intermediate K-93 was prepared in a manner similar to K-25. 1H NMR.

Synthesis of (E)-3-(1-Naphthalen-2-ylmethyl-2,3-dioxo-2,3-dihydro-1H-indol-7-yl)-acrylic acid methyl ester, K-94. To a pressure-resistant vial (50 mL) which contained a stirring suspension of K-93 (1.0 g, 2.4 mmol) in MeOH (10 mL) was added conc. HCl (10 mL) at rt. The reaction mixture which resulted was heated to 90° C., stirred at 90° C. for 3 h, cooled to rt and poured into 200 mL stirring ice-water solution. The solid which formed was filtered out, washed with water (3×100 mL) and dried over vacuum at 50° C. to provide the desired K-93 (750 mg, 77%) as orange color solid.

$^1$H-NMR (500 MHz, CDCl$_3$)(E)-3-(1-Naphthalen-2-ylmethyl-2,3-dioxo-2,3-dihydro-1H-indol-7-yl)-acrylic acid, A56. To a round bottom flask (200 mL) which contained a solution of NaOH (2000 mg) in MeOH (37 mL) and H$_2$O (35 mL) was added K-94 (2000 mg, 5.5 mmol) at rt. The reaction mixture which resulted was allowed to stir at rt for 24 h. The reaction mixture was cooled to 0° C. and was acidified with addition of aq HCl (2N) until pH=1, which was followed by addition of water (400 mL). The solid which formed was filtered out, washed with water (3×100 mL) and dried over vacuum at 50° C. to provide the desired A56 (1500 mg, 78%) as off-white solid. 1H-NMR (500 MHz, DMSO-d$_6$) 5.21 (s, 2H), 6.21 (d, J=15.6 Hz, 1H), 7.18 (dd, J=7.6 Hz, 1H), 7.48-7.54 (m, 3H), 7.64-7.71 (m, 2H), 7.76 (d, J=7.2 Hz, 1H), 7.81 (dd, J=6.0, 3.2 Hz, 1H), 7.86-7.90 (m, 2H), 7.92 (s, 1H)

LC/MS (100%) APCI– Calcd: 357.4 Found: 357.4

EXAMPLE 52

Preparation of A15

Synthesis of 3-(3-Hydroxy-1-naphthalen-2-ylmethyl-2-oxo-3-trifluoromethyl-2,3-dihydro-1H-indol-7-yl)-acrylic acid, A15. To a round bottom flask (125 mL) which contained a solution of A56 (120 mg, 0.3 mmol) and (trifluromethyl)trimethylsilane (0.4 mL, excess) in THF (50 mL) was added TBAF (13 mg, cat.) at 0° C. The mixture which resulted was allowed warm to rt and stir at rt for 16 h, then was cooled to 0° C. The reaction was quenched with the addition of aq HCl (10%, 0.5 mL) at rt and stirred at rt for 30 min. After removal of most THF and addition of water (30 mL), the mixture was extracted with CH$_2$Cl$_2$/MeOH (9/1, 3×10 mL). The combined organic layers were dried (Na$_2$SO$_4$) and the solvent was removed under reduced pressure to provide the crude product which was purified by flash chromatography (silica gel, CH$_2$Cl$_2$/EtOAc/hexane=1:1:4, EtOAc) to afford desired target A15 (80 mg, 60% yield) as a white solid. 1H NMR (500 MHz, acetone-d6) 5.29-5.67 (m, 2H), 6.22 (d, J=15.6 Hz, 1H), 7.24 (t, J=8.0 Hz, 1H), 7.43 (dd, J=12.4 Hz, 1.6 Hz, 1H), 7.60 (d, J=8.4 Hz, 1H), 7.67 (d, J=7.6 Hz, 1H), 7.78-7.80 (m, 1H), 7.85 (s, 1H), 7.86-7.91 (m, 2H), 8.20 (d, J=15.6 Hz, 1H), 10.41 (s, 1H), LC/MS (>90%) ESI– Calcd: 427.7; Found: 426.5 (M–1).

EXAMPLE 53

Preparation of A34

Synthesis of 1-(3,4-Dichloro-benzyl)-3a-methyl-1,3,3a,4,5,6-hexahydro-indol-2-one, K-41I: Following the general procedure P-1, (1-Methyl-2-oxo-cyclohexyl)-acetic acid, (K-40) was converted to K-41I. Consistent with 1H-NMR.

Synthesis of 7-Bromo-1-(3,4-Dichloro-benzyl)-3a-methyl-1,3,3a,4,5,6-hexahydro-indol-2-one, K-42I: Following the general procedure P-2, 1-(3,4-Dichloro-benzyl)-3a-methyl-1,3,3a,4,5,6-hexahydro-indol-2-one, K-41I was converted to K-42I. Consistent with 1H-NMR.

Synthesis of (E)-3-[1-(3,4-Dichloro-benzyl)-3a-methyl-2-oxo-2,3,3a,4,5,6-hexahydro-1H-indol-7-yl]-acrylic acid methyl ester, K-43I: Following the general procedure P-3, 7-Bromo-1-(3,4-Dichloro-benzyl)-3a-methyl-1,3,3a,4,5,6-hexahydro-indol-2-one, K-42I was converted to K-43I. Consistent with 1H-NMR.

Synthesis of (E)-3-[1-(3,4-Dichloro-benzyl)-3a-methyl-2-oxo-2,3,3a,4,5,6-hexahydro-1H-indol-7-yl]-acrylic acid, A34: Following the general procedure P-4, (E)-3-[1-(3,4-Dichloro-benzyl)-3a-methyl-2-oxo-2,3,3a,4,5,6-hexahydro-1H-indol-7-yl]-acrylic acid methyl ester, K-43I was converted to A34. 1H NMR (400 MHz, DMSO-d6) 1.16 (s, 3H), 1.60 (m, 1H), 1.70-1.82 (m, 3H), 2.16 (m, 1H), 2.20-2.36 (m, 2H), 2.62 (d, J=16.0 Hz, 1H), 4.83 (d, J=17.2 Hz, 1H), 4.97 (d, J=17.2 Hz, 1H), 5.54 (d, J=15.2 Hz, 1H), 7.15 (dd, J=8.4, 2.0 Hz, 1H), 7.47 (d, J=15.2 Hz, 1H), 7.49 (d, J=2.0 Hz, 1H), 7.58 (d, J=8.4 Hz, 1H), 11.92 (br s, 1H).

LCMS(97.4%) (ESI+) Calcd. for 380.3; Found: 382.1 (M+2).

EXAMPLE 54

Preparation of A57

Synthesis of (E)-3-(5-Fluoro-1H-indol-7-yl)-acrylic acid methyl ester, K-95. To a mixture of 7-Bromo-5-fluoro-1H-indole [which was prepared according to the known method (Dobbs, A., J. Org. Chem., 66, 638-641 (2001)], (400 mg, 1.87 mmol) and methyl acrylate (241 mg, 2.8 mmol) in triethylamine (1.5 ml), palladium(II)acetate (43 mg, 0.19 mmol) and tri-o-tolylphosphine (170 mg, 0.56 mmol) was added under argon at rt The reaction mixture was stirred at 100° C. for 4 hrs in a sealed pressure tube and then cooled to rt The reaction mixture was diluted with CH2Cl2 (50 ml), washed with water (3×30 ml), brine, and dried over sodium sulfate. After removal of solvent, the residue was purified by column chromatography on silica gel with ethyl acetate/hexane as an eluent to give 300 mg of compound K-95 as a yellow solid. 1H-NMR (500 MHz, CDCl3)

Synthesis of (E)-3-(5-Fluoro-1-imidazo[1,2-a]pyridin-2-ylmethyl-3-methyl-1H-indol-7-yl)-acrylic acid methyl ester, K-96. In an 8 mL vial equipped with a stir bar was placed compound K-95 (200 mg, 0.857 mmol) and anhydrous DMF (1.7 mL) at room temperature. The solution was cooled to 0° C. in an ice bath and then NaH (60%) (72.0 mg, 1.80 mmol) was added. The mixture was warmed to room temperature and then re-cooled to 0° C., upon which 2-chloromethyl-imidazo[1,2-a]pyridine (172 mg, 1.03 mmol) was added. The mixture was warmed to room temperature and allowed to react for a period of 26 hours. The reaction was quenched with water (2 mL) and 1M HCl (4 mL). The resulting mixture was transferred to a separatory funnel upon which water (20 mL) and 1M HCl (20 mL) were added. The aqueous portion was extracted with CH2Cl2 (2×40 mL) and EtOAc (2×40 mL). The organic portions were combined, dried (MgSO$_4$) and concentrated via rotary evaporation to yield crude K-96 as a tan solid. The crude product was triturated with ice cold CH2Cl2 (2 mL) and the resulting solid was collected via suction filtration and washed with ice cold CH2Cl2 (5 mL) to yield 80.1 mg of K-96 as a light tan solid (26%). $^1$H NMR (400 MHz, d$_6$-DMSO).

Synthesis of (E)-3-(5-Fluoro-1-imidazo[1,2-a]pyridin-2-ylmethyl-3-methyl-1H-indol-7-yl)-acrylic acid, A57. In an 8 mL vial equipped with a stir bar was placed compound K-96 (80.0 mg, 0.220 mmol), THF (600 µL), MeOH (225 µL) and 1.005 N NaOH (230 µL) at room temperature. The reaction was allowed to proceed at room temperature for a period of 22 hours and then additional 1.005 N NaOH (230 µL) was added. The contents of the vial were allowed to react for 5 hours at room temperature and then the reaction was quenched with water (2 mL) and acidified to pH 1 with 1M HCl. The resulting solid was collected by suction filtration and washed with CH2Cl2 (4 mL) to produce 10.0 mg of A57 as a yellow solid (13%). $^1$H NMR (400 MHz, d$_6$-DMSO) 2.25 (s, 3H), 5.80 (s, 2H), 6.30 (d, J=15.6 Hz, 1H), 7.27 (dd, J=2.4, 10.4 Hz, 1H), 7.39 (s, 2H), 7.44 (dd, J=2.4, 8.8 Hz, 1H), 7.81-7.90 (m, 3H), 8.03 (d, J=15.6 Hz, 1H), 8.72 (d, J=6.4 Hz, 1H). LC/MS (96%), MS (ESI–) Calcd.: 348.4 m/z, Found: 348.6 m/z.

EXAMPLE 56

Preparation of A58

Synthesis of 3-(1-Naphthalen-2-ylmethyl-1H-indol-7-yl)-propionic acid, A58. To a solution of A53 (15 mg, 0.05 mmol) in MeOH (3 mL) was added Pd/C (60% in mineral oil, 5 mg) at rt. The flask containing this mixture was evacuated and then charged with H$_2$ through use of a balloon. The flask was evacuated and recharged with H$_2$ three times and the mixture was allowed to stir at rt under 1 atmosphere of H$_2$ for 16 h. The solid was filtered out and washed with MeOH (10 mL). The combined organic filtrates were dried (Na$_2$SO$_4$) and the solvent was removed under reduced pressure to provide the crude product which was purified by flash chromatography (silica gel, CH$_2$Cl$_2$;/EtOAc/hexane,=1:8-1:2) to afford desired A58 (5 mg, 32%) as a oil.

1H NMR (500 MHz, acetone-d6): 2.56 (t, J=8.5 Hz, 2H), 3.16 (t, J=8.0 Hz, 2H), 5.84 (s, 2H), 6.60 (d, J=3.0 Hz, 1H), 6.92-6.99 (m, 2H), 7.19 (dd, J=8.5 Hz, J=1.5 Hz, 1H), 7.34 (s, 1H), 7.40-7.47 (m, 3H), 7.50 (dd, J=8.0 Hz, J=1.5 Hz, 1H), 7.69 (t, J=5.0 Hz, 1H), 7.83-7.86 (m, 1H).

LCMS (75%) (ESI–) Calcd: 329.4; Found: 328.6 (M–1).

EXAMPLE 58

Preparation of A60

Synthesis of (E)-3-[1-(3,4-Difluoro-benzyl)-2,3-dioxo-2,3-dihydro-1H-indol-7-yl]-acrylic acid, A60. K-24 was converted to A60 in a manner analogous to the conversion of K-24 to A17. 1H NMR (DMSO-d6) 5.04 (s, 2H), 6.20 (d, J=15.6 Hz, 1H), 7.18 (dd, J=7.6, 7.6 Hz, 1H), 7.31 (m, 1H), 7.37 (ddd, J=16.8, 10.8, 8.4 Hz, 1H), 7.52 (d, J=15.6 Hz, 1H), 7.57 (m, 1H), 7.66 (dd, J=7.2, 1.6 Hz, 1H), 7.76 (dd, J=8.0, 0.8 Hz, 1H), 12.43 (s, 1H). LC/MS (93%) ESI– Calcd. 343.3 m/z Found: 342.6 (M–1) m/z

EXAMPLE 58

Preparation of A62

Synthesis of (E)-3-[1-(2,4-Dichloro-benzyl)-3,3-bis-hydroxymethyl-2-oxo-2,3-dihydro-1H-indol-7-yl]-acrylic acid, A62. In an 8 mL vial equipped with a stir bar was placed acid A18** (100 mg, 0.276 mmol), anhydrous 1,4-dioxane (500 µL), Na$_2$CO$_3$ (6.15 mg, 0.0580 mmol) followed by the addition of 37 wt. % CH$_2$O in water (70 µL) at room temperature. The reaction was allowed to proceed at room temperature for a period of 22 hours. The reaction was quenched with water (2 mL) and acidified to pH 1 with 1M HCl. The resulting solid was collected by suction filtration, washed with water (2×2 mL) and dried in a high vacuum oven set at 45° C. for a period of 4 hours. The resulting solid was purified on a SiO$_2$ preparative TLC plate employing 20% MeOH/CH2Cl2 as the eluent. The SiO$_2$ containing the product was removed and washed with 50% MeOH/CH2Cl2 (50 mL) and acetone (50 mL). After removing solvents by rotary evaporation, 44 mg of pure compound A62 was isolated as an off-white solid (37%). $^1$H NMR (400 MHz, d$_6$-DMSO) 3.60 (bs, 2H), 3.77 (dd, J=10, 35.2 Hz, 4H), 5.03 (s, 2H), 6.12 (d, J=15.6 Hz, 1H), 7.08-7.17 (m, 3H), 7.28-7.35 (m, 2H), 7.48 (d, J=6.8 Hz, 1H), 7.66 (s, 1H). LC/MS (70%) MS (ESI–) Calcd.: 421.3 m/z, Found: 421.1 m/z.

EXAMPLE 59

Preparation of A33

Synthesis of 4-Bromoisatin (K-98) and 6-Bromoisatin (K-99). To a solution chloral hydride (50.0 g, 0.247 mol) in water (237 mL) were successively added Na$_2$SO$_4$ (69.0 g, 0.486 mol), 3-bromoaniline (40.0 g, 0.233 mol) in a mixture of 37% HCl (25 ml, 0.302 mol) and water (632 ml) with vigorous stirring. After the addition was completed, the resulting reaction mixture was heated to reflux for 10 min, and allowed to cool to room temperature. The precipitate formed was collected by filtration, washed with water (3×100 ml) and dried in vacuo to yield the crude isonitrosoacetanilide. This product was added portion-wise to rapidly stirred concentrated H$_2$SO$_4$ (790 ml) at a rate to keep the reaction temperature between 50 and 70° C. The reaction mixture was heated to 80° C. for 20 min and allowed to cool to room temperature. The cooled mixture was poured into crushed ice (ca. 3200 g). The mixture was allowed to stand for 1 h. The orange precipitate was collected by a filtration, washed with water and dried to yield a mixture of 4-bromoisatin (K-98) and 6-bromoisatin (K-99) (40 g, 83%). MS (ESI+): 227 (M+1). 1H-NMR (DMSO-d$_6$)

Synthesis of 4-Bromoisatin-3-ethylene acetal, K-100. To a mixture of 4-bromoisatin (K-98) and 6-bromoisatin (K-99) (25.0 g, 0.111 mol) was added ethylene glycol (27.5 g, 0.442 mol) and p-toluenesulfonic acid monohydrate (2.5 g, 11.3 mmol) and benzene (500 ml) and the resulting mixture was heated to reflux with Dean Stock trap to remove the water generated. The reaction mixture was allowed to cool to room temperature, washed with 10% aq NaHCO$_3$ and then water. After concentrated, the crude product (25 g) was obtained and purified by recrystallization in EA/Hex to afford 4-Bromoisotin-3-ethlyene acetal, K-100 (8.2 g, 27% yield) as off-white solid. 1H-NMR (DMSO-d6), MS (ESI+): 270 (M+1).

Synthesis of 1-Methyl 4-Bromoisatin-3-ethylene acetal, K-101. To a suspension of K-100 (2.7 g 10 mmol) in acetone (30 mL) and DMF (5 mL) was added aq. NaOH (2N, 5 mL) and MeI (10 mL) at rt. The reaction mixture was allowed to stir at rt for 16 h and then cooled to 0° C., quenched with aq. NH$_4$Cl (sat., 10 mL). After the addition of 50 mL water, The mixture was extracted with EtOAc. The organic layers were washed with water, brine (30 ml) and dried over Na$_2$SO$_4$. After removal of the solvent, the crude product was purified by recrystallization in EA/Hex to afford K-101 (2 g, 70.4% yield) as off-white solid. $^1$H-NMR (CDCl$_3$), MS (ESI+)

Synthesis of 4-Bromo-1-methyl-1H-indole-2,3-dione, K-102. To a stirring suspension of K-101 (2. g, 7 mmol) in MeOH (50 ml) was added conc. HCl (50 ml) at rt. The resulting reaction mixture was heated to at 100° C. for 4 h, cooled to rt and poured into 200 ml of a stirring ice-water solution. The precipitate formed was collected by a filtration, washed with water and dried to yield K-102 (1.68 g, 98%) as orange color solid. 1H-NMR, MS (ESI+)

Synthesis of 4-Bromo-1-methyl-1,3-dihydro-indol-2-one, K-103. To a pressure-resistant flask (350 mL) which contained K-102 (1200 mg, 5 mmol) was added NH$_2$NH$_2$.H$_2$O (50 mL) at rt. The mixture which resulted was sealed, heated to 130° C. and stirred at 130° C. for 1 h, then was cooled to 0° C. After the addition ice-water (500 mL), the reaction mixture was stirred at 0° C. for 30 min. The solid which formed was filtered out, washed with water (3×50 mL) and dried over vacuum at 50° C. to afford desired target K-103 (720 mg, 80% yield) as a white solid. 1H-NMR, MS (ESI+).

Synthesis of (E)-3-(1-Methyl-2-oxo-2,3-dihydro-1H-indol-4-yl)-acrylic acid methylester, K-104. A mixture of K-103 (500 mg, 2.2 mmol), tri-o-tolylphosphine (240 mg, 0.8 mmol) and palladium acetate (50 mg, 0.2 mmol) in triethylamine (10 mL) and methyl acrylate (600 mg, 7.0 mmol) in a sealed tube was heated to 100° C. and stirred at 100° C. for 4 h, then cooled. The reaction mixture was poured into 100 ml of stirring ice-water solution, extracted with EtOAc. The organic layers were washed with water, brine (50 mL) and dried over Na$_2$SO$_4$. After removal of the solvent, the crude product was purified by a chromatography on silica gel to afford K-104 (300 mg, 61%) as off-white solid. 1H-NMR, MS (ESI+):

Synthesis of (E)-3-[3-(2,4-Dichloro-phenylcarbamoyl)-1-methyl-2-oxo-2,3-dihydro-1H-indol-4-yl]-acrylic acid methyl ester, K-105. To a suspended mixture of K-104 (100 mg, 0.44 mmol) and Cs$_2$CO$_3$ (160 mg) in DMF (5 ml) was added 2,4-Dichloro-1-isocyanato-benzene at rt. The reaction mixture was allowed to stir at rt for 24 h and then cooled to 0° C. The mixture was poured into 30 mL stirring ice-water solution and extracted with EtOAc (3×30 mL). The organic layers were washed with water, brine (30 mL) and dried over Na$_2$SO$_4$. After removal of the solvent, the crude product was purified by a chromatography on silica gel to afford K-105 (110 mg, 61%) as off-white solid. 1H-NMR Synthesis of (E)-3-[3-(2,4-Dichloro-phenylcarbamoyl)-1-methyl-2-oxo-2,3-dihydro-1H-indol-4-yl]-acrylic acid, A33. To a solution of the ester K-105 (100 mg, 0.2 mmol) in MeOH (7 mL) was added a solution of. NaOH (100 mg) in water (8 mL) at rt, The reaction mixture was allowed to stir at room temperature for 72 h. After the methanol was removed, the aqueous residue was cooled to −5° C. and acidified with 10% HCl to pH∼1. The precipitate was collected by a filtration, washed with water and dried to yield the crude which was further purified by recrystallization in acetone/EA/Hex to afford A33 (80 mg, 82%) as off-white solid. 1H NMR (500 MHz, DMSO-d6) 3.18 (s, 3H), 5.18 (s, 1H), 6.55 (d, J=16.0 Hz, 1H), 7.10 (d, J=8.0 Hz, 1H), 7.38-7.43 (m, 2H), 7.50 (d, J=8.0 Hz, 1H), 7.64-7.14 (m, 3H), 10.41 (s, 1H), LC/MS (>85%) (ESI−) Calcd: 405.2; Found: 403.3 (M−2), 404.3 (M−1).

EXAMPLE 60

Preparation of A63

5-Allyl-6-chloro-1H-pyrimidine-2,4-dione was obtained according to I. Ishikawa, V. E. Khachatrian, R. G. Melik-Ohanjanian, N. Kawahara, Y. Mizuno, H. Ogura. Chem. Pharm. Bull 40 (4), 846-850 (1992) (3-(5-Allyl-6-chloro-3-methyl-2,4-dioxo-3,4-dihydro-2H-pyrimidin-1-yl)-propionic acid ethyl ester, K-107. LiH (20 mg, 2.52 mmol, 1.6 equiv.) was added at −78° C. in one portion to a solution of 5-allyl-6-chloro-1H-pyrimidine-2,4-dione (294 mg, 1.58 mmol, 1 equiv.) in DMF (3 mL) and the reaction mixture was warmed up to rt using a water bath. Ethyl-3-bromopropionate (285 mg, 1.58 mmol, 1 equiv.) was added in 1 min and the reaction mixture was heated and stirred at 85° C. for 45 min. The reaction mixture was cooled to −78° C. and LiH (13 mg, 1.58 mmol, 1.0 equiv.) was added in one portion. The reaction mixture was warmed to rt and stirred for 5 min. Methyl iodide (440 mg, 3.1 mmol, 2 equiv.) was added in 1 min and the reaction mixture was heated and stirred at 75° C. for 30 min in a tightly closed vial. The reaction mixture was cooled to rt and quenched with water (4 mL), followed by 10% aqueous HCl (0.5 mL). The mixture was extracted with ether (3×4 mL). The combined organic extracts were washed with water (6 mL), brine (6 mL), dried over MgSO$_4$, filtered, and concentrated to yield K-107 (200 mg, 40%) as an orange oil. R$_f$ 0.65 (EtOAc/hexanes, 1:1). MS: AP+ Calcd. 300 (M) Found: 301.5 (M+1). $^1$H-NMR (400 MHz, CDCl$_3$) confirmed the structure.

Synthesis of (3-[5-Allyl-6-(2,4-dichloro-benzylamino)-3-methyl-2,4-dioxo-3,4-dihydro-2H-pyrimidin-1-yl]-propionic acid ethyl ester, K-108. A solution of K107 (88 mg, 0.293 mmol, 1 equiv.), 2,4-dichlorobenzylamine (62 mg, 0.351 mmol, 1.2 equiv.), triethylamine (45 mg, 0.44 mmol, 1.5 equiv.) in 1-methyl-2-pyrrolidinone (1 mL) was heated and stirred at 125° C. for 15 h. and then at 145° C. for 3 h. The reaction mixture was cooled to rt and diluted with ether (6 mL), washed with brine (6 mL), water (2×6 mL), brine (6 mL), dried over MgSO$_4$, filtered, and concentrated to yield crude product (134 mg) as brown oil. The crude oil was chromatographed on silica gel (Flash, 5 g, wet in EtOAc/hexanes, 1:2), eluted with EtOAc/hexanes, 1:2 to afford K-108 (35 mg, 27%) as a yellow oil. R$_f$ 0.48 (EtOAc/hexanes, 1:1). MS: ESI− Calcd. 439 (M) Found: 438.4 (M−1). $^1$H-NMR (400 MHz, CDCl$_3$) confirmed the structure.

Synthesis of (3-[7-(2,4-Dichloro-benzyl)-3,6-dimethyl-2,4-dioxo-2,3,4,7-tetrahydro-pyrrolo[2,3-d]pyrimidin-1-yl]-propionic acid ethyl ester, K-109. A solution of K-108 (33 mg, 0.075 mmol, 1 equiv.), 1,4-benzoquinone (8 mg, 0.075 mmol, 1.0 equiv.), bis(acetonitrile)dichloro Pd(II) (1.9 mg, 0.0075 mmol, 0.1 equiv.), lithium chloride (32 mg, 0.75 mmol, 10 equiv.) in anhydrous THF (1.9 mL) was stirred at rt for 64 h. The reaction mixture was concentrated, water (1 mL) was added, and the mixture was extracted with EtOAc (2 mL). Organic phase was washed with water (1 mL), brine (1 mL), dried over MgSO$_4$, filtered, and concentrated to afford K-109 (38 mg, quant.) as brown oil. R$_f$ 0.51 (EtOAc/hexanes, 1:1). MS: AP$^+$ Calcd. 437 (M) Found: 438.4 (M+1). $^1$H-NMR (400 MHz, CDCl$_3$) confirmed the structure.

Synthesis of (3-[7-(2,4-Dichloro-benzyl)-3,6-dimethyl-2,4-dioxo-2,3,4,7-tetrahydro-pyrrolo[2,3-d]pyrimidin-1-yl]-propionic acid, A63. A solution of K-109 (31 mg, 0.071 mmol, 1 equiv.), 2 N aqueous NaOH (0.14 mL, 0.28 mmol, 4 equiv.) in THF-MeOH (1:1, 0.3 mL) was stirred at rt for 15 min. The reaction mixture was concentrated and quenched with 10% aqueous HCl (1 mL). The mixture was extracted with EtOAc (2×1 mL). The combined organic extracts were washed with water (2×1 mL), brine (1 mL), dried over MgSO$_4$, filtered, and concentrated to afford A63 (15 mg, 51%) as a brown solid. R$_f$ 0.28 (EA). 1H-NMR (400 MHz, DMSO-d6) 2.11 (d, J=0.8 Hz, 3H), 2.47 (t, J=8.0 Hz, 2H), 3.40 (s, 3H), 4.07 (t, J=8.0 Hz, 2H), 5.45 (s, 2H), 6.32 (d, J=0.8 Hz, 1H), 6.47 (d, J=8.4 Hz, 1H), 7.41 (dd, J=8.4 Hz, J=2.0 Hz, 1H), 7.76 (d, J=2.0 Hz, 1H). LC-MS (100%): AP$^-$ Calcd. 410 (M) Found: 409.4 (M−1).

EXAMPLE 61

Preparation of A64

Synthesis of (E)-4-[1-(2,4-Dichloro-benzyl)-5-fluoro-3-methyl-1H-indol-7-yl]-1,1,1-trifluoro-2-trifluoromethyl-but-3-en-2-ol, A64. To a solution of K-60 (300 mg, 0.775 mmole) in acetonitrile (0.5 mL) were added: triethylamine (0.65 ml, 4.65 mmole), 2-vinylhexafluoroisopropanol (226 mg, 1.16 mmole), Pd(OAc)$_2$ (9 mg, 0.038 mmole) and tri-o-tolylphosphine (36 mg, 0.116 mmole). The reaction mixture was heated at 90° C. for 3 h. The cooled reaction mixture was concentrated and diluted with ether (15 mL). The solution was washed with water, brine, dried over Na$_2$SO$_4$, filtered and concentrated to give 440 mg of a residue. Purification of this residue by silica gel column chromatography using 5% ethyl acetate/hexanes gave 70 mg of A64 and 75 mg of recovered unreacted K-60, 24% yield. 1H-NMR (400 MHz, CDCl$_3$), 2.3 (s, 3H), 3.05 (bs, 1H), 5.38 (s, 2H), 5.99 (d, J=15.6 Hz, 1H), 6.29 (d, J=8.4 Hz, 1H), 6.87 (s, 1H), 6.9 (dd, J=10, 2.8 Hz, 1H), 7.07 (dd, J=8.4 2 Hz, 1H), 7.233-7.275 (m, overlap, 2H), 7.44 (d, J=2, 1H). LC/MS (ESI−) 498: 98%.

What is claimed is:
1. A compound of formula

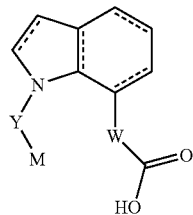

wherein the bonds between the ring members of the ring system may be single or double bonds, said ring system substituted with from zero to four substituents chosen independently from halogen, —OH, loweralkyl, —O-loweralkyl, fluoroloweralkyl, —O-lowerfluoroalkyl, methylenedioxy, ethylenedioxy, alkoxy-loweralkyl, hydroxyloweralkyl, oxo, —CN, nitro, —S—loweralkyl, amino, loweralkylamino, diloweralkylamino, diloweralkylaminoalkyl, carboxy, carboalkoxy, acyl, carboxamido, loweralkylsulfoxide, acylamino, phenyl, benzyl, spirothiazolidinyl, phenoxy and benzyloxy; with the proviso that 3-unsubstituted-2-oxoindoles are excluded;

W is chosen from C$_2$ to C$_8$ linear alkyl in which one or two —CH$_2$— may be replaced independently by either of —CH=CH— and —CF$_2$—;

Y is chosen from C$_1$ to C$_8$ alkyl in which one or two —CH$_2$— may be replaced independently by either of —CO(=O)—, —CH=CH—, and —CF$_2$—;

M is chosen from phenyl, and phenyl substituted with from one to three substituents chosen from halogen, trifluoromethyl, methyl, methoxy, trifluoromethoxy, methanesulfonyl, methylenedioxy, and ethylenedioxy.

2. A compound according to claim 1 wherein
W is —CH=CH—; and
Y is —CH$_2$—.

3. A compound according to claim 1 wherein the ring system is chosen from an indole, a 3-substituted-2-oxoindole, an indoline, and an isatin.

4. A pharmaceutical composition comprising a pharmaceutically acceptable carrier and a compound according to claim 1.

5. A pharmaceutical formulation according to claim 4 comprising an additional therapeutic agent chosen from a platelet aggregation inhibitor, an HMG-CoA reductase inhibitor, an antihyperlipidemic agent and a cyclooxygenase inhibitor.

6. A pharmaceutical formulation according to claim 5 wherein said platelet aggregation inhibitor is chosen from tirofiban, dipyridamole, clopidogrel and ticlopidine.

7. A pharmaceutical formulation according to claim 5 wherein said HMG-CoA reductase inhibitor is chosen from lovastatin, simvastatin, pravastatin, rosuvastatin, mevastatin, atorvastatin, cerivastatin, pitavastatin and fluvastatin.

8. A pharmaceutical formulation according to claim 5 wherein said cyclooxygenase inhibitor is chosen from rofecoxib, meloxicam, celecoxib, etoricoxib, lumiracoxib, valdecoxib, parecoxib, cimicoxib, diclofenac, sulindac, etodolac, ketoralac, ketoprofen, and piroxicam.

9. A compound according to claim 1 of formula

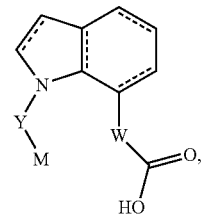

said ring system substituted with from zero to four substituents chosen independently from halogen, —OH, loweralkyl, —O-loweralkyl, fluoroloweralkyl, —O-lowerfluoroalkyl, methylenedioxy, ethylenedioxy, alkoxy-loweralkyl, hydroxyloweralkyl, oxide, —CN, nitro, —S—loweralkyl, amino, loweralkylamino, diloweralkylamino, diloweralkylaminoalkyl, carboxy, carboalkoxy, acyl, carboxamido, loweralkylsulfoxide, acylamino, phenyl, benzyl, spirothiazolidinyl, phenoxy and benzyloxy, said ring system chosen from:
indole,
reduced indole,
2-oxoindole, reduced 2-oxoindole,

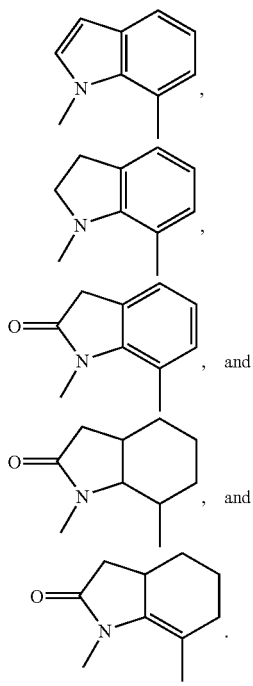

10. A compound according to claim 9 wherein said ring system is indole of formula:

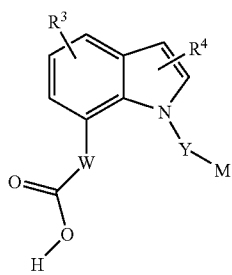

wherein

R³ and R⁴ are substituents in either or both rings, chosen independently from hydrogen, halogen, —OH, loweralkyl, —O-loweralkyl, fluoroloweralkyl, —O-lowerfluoroalkyl, methylenedioxy, ethylenedioxy, alkoxyloweralkyl, hydroxyloweralkyl, —CN, nitro, —S—loweralkyl, amino, loweralkylamino, diloweralkylamino, diloweralkylaminoalkyl, carboxy, carboalkoxy, acyl, carboxamido, loweralkylsulfoxide, acylamino, phenyl, benzyl, spirothiazolidinyl, phenoxy and benzyloxy.

11. A compound according to claim 9 wherein said ring system is 2-oxoindole of formula:

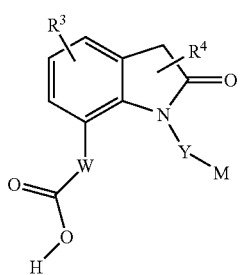

wherein

R³ and R⁴ are substituents in either or both rings, chosen independently from hydrogen, halogen, —OH, loweralkyl, —O-loweralkyl, fluoroloweralkyl, —O-lowerfluoroalkyl, methylenedioxy, ethylenedioxy, alkoxyloweralkyl, hydroxyloweralkyl, oxo, —CN, nitro, —S-loweralkyl, amino, loweralkylamino, diloweralkylamino, diloweralkylaminoalkyl, carboxy, carboalkoxy, acyl, carboxamido, loweralkylsulfoxide, acylamino, phenyl, benzyl, spirothiazolidinyl, phenoxy and benzyloxy.

12. A compound according to claim 9 wherein said ring system is a reduced 2-oxoindole of formula:

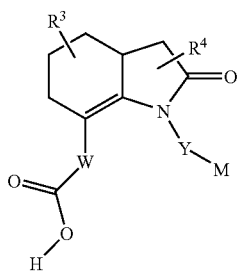

wherein

R³ and R⁴ are substituents in either or both rings, chosen independently from hydrogen, halogen, —OH, loweralkyl, —O-loweralkyl, fluoroloweralkyl, —O-lowerfluoroalkyl, methylenedioxy, ethylenedioxy, alkoxyloweralkyl, hydroxyloweralkyl, oxo, —CN, nitro, —S-loweralkyl, amino, loweralkylamino, diloweralkylamino, diloweralkylaminoalkyl, carboxy, carboalkoxy, acyl, carboxamido, loweralkylsulfoxide, acylamino, phenyl, benzyl, spirothiazolidinyl, phenoxy and benzyloxy.

13. A compound according to claim 9 wherein
W is —CH=CH—; and
Y is —CH₂—.

* * * * *